US008440716B2

(12) United States Patent
Tang et al.

(10) Patent No.: US 8,440,716 B2
(45) Date of Patent: May 14, 2013

(54) DEACETYLASE INHIBITORS AND USES THEREOF

(75) Inventors: Weiping Tang, Middleton, WI (US); James Elliot Bradner, Cambridge, MA (US); Stuart L. Schreiber, Boston, MA (US)

(73) Assignees: President and Fellows of Harvard College, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 235 days.

(21) Appl. No.: 13/055,241

(22) PCT Filed: Jul. 22, 2009

(86) PCT No.: PCT/US2009/004235

§ 371 (c)(1),
(2), (4) Date: Apr. 1, 2011

(87) PCT Pub. No.: WO2010/011296

PCT Pub. Date: Jan. 28, 2010

(65) Prior Publication Data

US 2011/0172303 A1 Jul. 14, 2011

Related U.S. Application Data

(60) Provisional application No. 61/082,899, filed on Jul. 23, 2008.

(51) Int. Cl.

| | |
|---|---|
| ***A61K 31/24*** | (2006.01) |
| ***A61K 31/195*** | (2006.01) |
| ***A61K 31/165*** | (2006.01) |
| ***C07C 229/02*** | (2006.01) |
| ***C07C 251/00*** | (2006.01) |
| ***C07C 233/88*** | (2006.01) |

(52) U.S. Cl.
USPC ........... 514/539; 514/563; 514/615; 564/158; 560/37; 562/440

(58) Field of Classification Search .................. 514/539, 514/563, 615; 564/158; 560/37; 562/440
See application file for complete search history.

(56) References Cited

U.S. PATENT DOCUMENTS

| | | | |
|---|---|---|---|
| 4,631,211 | A | 12/1986 | Houghten |
| 4,639,462 | A | 1/1987 | Kramer et al. |
| 4,683,195 | A | 7/1987 | Mullis et al. |
| 4,683,202 | A | 7/1987 | Mullis |
| 4,820,828 | A | 4/1989 | Demers et al. |
| 4,833,080 | A | 5/1989 | Brent et al. |
| 5,045,538 | A | 9/1991 | Schneider et al. |
| 5,059,698 | A | 10/1991 | Schulthess et al. |
| 5,096,815 | A | 3/1992 | Ladner et al. |
| 5,143,854 | A | 9/1992 | Pirrung et al. |
| 5,176,996 | A | 1/1993 | Hogan et al. |
| 5,198,346 | A | 3/1993 | Ladner et al. |
| 5,223,409 | A | 6/1993 | Ladner et al. |
| 5,225,173 | A | 7/1993 | Wai |
| 5,238,781 | A | 8/1993 | Schadeli |
| 5,256,775 | A | 10/1993 | Froehler |
| 5,264,564 | A | 11/1993 | Matteucci |
| 5,283,317 | A | 2/1994 | Saifer et al. |
| 5,288,514 | A | 2/1994 | Ellman |
| 5,304,121 | A | 4/1994 | Sahatjian |
| 5,328,470 | A | 7/1994 | Nabel et al. |
| 5,359,115 | A | 10/1994 | Campbell et al. |
| 5,362,899 | A | 11/1994 | Campbell |
| 5,393,741 | A | 2/1995 | Pettersen et al. |
| 5,440,016 | A | 8/1995 | Blondelle et al. |
| 5,480,971 | A | 1/1996 | Houghten et al. |
| 5,659,016 | A | 8/1997 | Nakamura et al. |
| 5,700,811 | A | 12/1997 | Breslow et al. |
| 5,763,182 | A | 6/1998 | Nakamura et al. |
| 5,837,313 | A | 11/1998 | Ding et al. |
| 5,886,026 | A | 3/1999 | Hunter et al. |
| 5,891,507 | A | 4/1999 | Jayaraman |
| 6,030,945 | A | 2/2000 | Ashkenazi |
| 6,068,987 | A | 5/2000 | Dulski et al. |
| 6,071,305 | A | 6/2000 | Brown et al. |
| 6,099,562 | A | 8/2000 | Ding et al. |
| 6,153,252 | A | 11/2000 | Hossainy et al. |
| 6,190,619 | B1 | 2/2001 | Kilcoin et al. |
| 6,195,612 | B1 | 2/2001 | Pack-Harris |
| 6,203,551 | B1 | 3/2001 | Wu |
| 6,231,600 | B1 | 5/2001 | Zhong |
| 6,248,127 | B1 | 6/2001 | Shah et al. |

(Continued)

FOREIGN PATENT DOCUMENTS

| | | |
|---|---|---|
| DE | 32 422 252 | 1/1987 |
| EP | 0 259 149 A2 | 3/1988 |

(Continued)

OTHER PUBLICATIONS

Extended European Search Report for EP 07872648.6 mailed Apr. 13, 2011.

Extended European Search Report for EP 07757000.0 mailed May 3, 2011.

Office Communication, mailed Jun. 20, 2011, for U.S. Appl. No. 12/279,440.

Notice of Allowance, mailed Jun. 8, 2011, for U.S. Appl. No. 12/196,878.

Notice of Allowance, mailed Aug. 17, 2011, for U.S. Appl. No. 12/370,390.

(Continued)

*Primary Examiner* — Renee Claytor
*Assistant Examiner* — Sahar Javanmard
(74) *Attorney, Agent, or Firm* — Wolf, Greenfield & Sacks, P.C.; C. Hunter Baker

(57) ABSTRACT

The present invention provides novel compounds of formula (I) and pharmaceutical compositions thereof. The inventive compounds are useful as deacetylase inhibitors (e.g., histone deacetylase inhibitors) and may be useful in the treatment of proliferative diseases such as cancer. In particular, the inventive compounds are HDAC6 inhibitors. The invention also provide synthetic methods for preparing the inventive compounds.

19 Claims, 9 Drawing Sheets

U.S. PATENT DOCUMENTS

| | | | |
|---|---|---|---|
| 6,251,136 | B1 | 6/2001 | Guruwaiya et al. |
| 6,258,121 | B1 | 7/2001 | Yang et al. |
| 6,273,913 | B1 | 8/2001 | Wright et al. |
| 6,428,960 | B1 | 8/2002 | Clark et al. |
| 6,495,719 | B2 | 12/2002 | Lan-Hargest et al. |
| 6,512,123 | B2 | 1/2003 | Grossmann et al. |
| 6,517,889 | B1 | 2/2003 | Jayaraman |
| 6,541,661 | B1 | 4/2003 | Delorme et al. |
| 6,777,217 | B1 | 8/2004 | Schreiber et al. |
| 6,897,220 | B2 | 5/2005 | Delorme et al. |
| 6,960,685 | B2 | 11/2005 | Watkins et al. |
| 7,244,853 | B2 | 7/2007 | Schreiber et al. |
| 7,250,504 | B2 | 7/2007 | Grozinger et al. |
| 7,994,362 | B2 | 8/2011 | Schreiber et al. |
| 2001/0027340 | A1 | 10/2001 | Wright et al. |
| 2003/0004209 | A1 | 1/2003 | Hunter et al. |
| 2003/0129724 | A1 | 7/2003 | Grozinger et al. |
| 2003/0187027 | A1 | 10/2003 | Schreiber et al. |
| 2004/0072849 | A1 | 4/2004 | Schreiber et al. |
| 2004/0087631 | A1 | 5/2004 | Bacopoulos et al. |
| 2004/0092598 | A1 | 5/2004 | Watkins et al. |
| 2004/0127522 | A1 | 7/2004 | Chiao et al. |
| 2004/0138153 | A1 | 7/2004 | Ramesh et al. |
| 2005/0014839 | A1 | 1/2005 | Kozikowski et al. |
| 2005/0267037 | A1 | 12/2005 | Anderson et al. |
| 2005/0287629 | A1 | 12/2005 | Grozinger et al. |
| 2006/0020131 | A1 | 1/2006 | Raeppel et al. |
| 2006/0079528 | A1 | 4/2006 | Finn et al. |
| 2006/0239909 | A1 | 10/2006 | Anderson et al. |
| 2007/0093413 | A1 | 4/2007 | Schreiber et al. |
| 2008/0269245 | A1 | 10/2008 | Schreiber et al. |
| 2008/0300205 | A1 | 12/2008 | Tsai et al. |
| 2009/0036318 | A1 | 2/2009 | Grozinger et al. |
| 2009/0209590 | A1 | 8/2009 | Mazitschek et al. |
| 2009/0221474 | A1 | 9/2009 | Schreiber et al. |
| 2009/0305384 | A1 | 12/2009 | Grozinger et al. |
| 2009/0312363 | A1 | 12/2009 | Bradner et al. |
| 2010/0056588 | A1 | 3/2010 | Bradner et al. |
| 2010/0137196 | A1 | 6/2010 | Schreiber et al. |
| 2011/0218154 | A1 | 9/2011 | Schreiber et al. |

FOREIGN PATENT DOCUMENTS

| | | | |
|---|---|---|---|
| EP | 0 322 335 | A1 | 6/1989 |
| EP | 0 323 590 | A2 | 7/1989 |
| EP | 0 331 524 | A2 | 9/1989 |
| EP | 0 458 131 | A1 | 11/1991 |
| EP | 0 708 112 | A1 | 4/1996 |
| GB | 2 169 599 | A | 7/1986 |
| JP | 8-311321 | A | 11/1996 |
| JP | 9-124918 | A | 5/1997 |
| WO | WO 91/00257 | A1 | 1/1991 |
| WO | WO 91/07087 | A1 | 5/1991 |
| WO | WO 92/09690 | A2 | 6/1992 |
| WO | WO 92/10092 | A1 | 6/1992 |
| WO | WO 92/15694 | A1 | 9/1992 |
| WO | WO 93/05807 | A2 | 4/1993 |
| WO | WO 93/07867 | A1 | 4/1993 |
| WO | WO 93/09668 | A1 | 5/1993 |
| WO | WO 93/19778 | A1 | 10/1993 |
| WO | WO 93/20242 | A1 | 10/1993 |
| WO | WO 94/08051 | A1 | 4/1994 |
| WO | WO 94/10300 | A1 | 5/1994 |
| WO | WO 97/11366 | A1 | 3/1997 |
| WO | WO 97/35990 | A2 | 10/1997 |
| WO | WO 98/16830 | A2 | 4/1998 |
| WO | WO 98/47869 | A1 | 10/1998 |
| WO | WO 98/55449 | A1 | 12/1998 |
| WO | WO 00/20415 | A1 | 4/2000 |
| WO | WO 00/34313 | A1 | 6/2000 |
| WO | WO 00/35911 | A1 | 6/2000 |
| WO | WO 00/36132 | A1 | 6/2000 |
| WO | WO 00/44709 | A2 | 8/2000 |
| WO | WO 02/89782 | A2 | 11/2002 |
| WO | WO 2004/001059 | A2 | 12/2003 |
| WO | WO 2004/046104 | A2 | 6/2004 |
| WO | WO 2004/103369 | A1 | 12/2004 |
| WO | WO 2005/007091 | A2 | 1/2005 |
| WO | WO 2005/012247 | A1 | 2/2005 |
| WO | WO 2005/018578 | A2 | 3/2005 |
| WO | WO 2005/066151 | A2 | 7/2005 |
| WO | WO 2005/080335 | A1 | 9/2005 |
| WO | WO 2006/060676 | A1 | 6/2006 |
| WO | WO 2006/060809 | A2 | 6/2006 |
| WO | WO 2008/040934 | A1 | 4/2008 |
| WO | WO 2009/063054 | A1 | 5/2009 |
| WO | WO 2011/019393 | A2 | 2/2011 |

OTHER PUBLICATIONS

Andrews et al., Anti-malarial effect of histone deacetylation inhibitors and mammalian tumour cytodifferentiating agents. Int J Parasitol. May 2000;30(6):761-8.

Baldwin et al., Total Synthesis of Antitumor Agent At-125-(Aphas, 5S)-Alpha-Amino-3-Chloro-4,5-Isoxazoleacetic Acid. Tetrahedron. 1985;41(22):5241-60.

Breslow et al., Potent cytodifferentiating agents related to hexamethylenebisacetamide. Proc Natl Acad Sci U S A. Jul. 1, 1991;88(13):5542-6.

Dankwardt et al., Solid-phase synthesis of di- and tripeptidic hydroxamic acids as inhibitors of procollagen C-proteinase. Bioorg Med Chem Lett. Nov. 20, 2000;10(22):2513-6.

Farkas et al., A comparison between the chelating properties of some dihydroxamic acids, desferrrioxamine B and acetohydroxamic acid. Polyhedron. 1999;18(1999):2391-98.

Giacomelli et al., Simple one-flask method for the preparation of hydroxamic acids. Org Lett. Jul. 24, 2003;5(15):2715-7.

Hynes, Hydroxylamine derivatives as potential antimalarial agents. 1. Hydroxamic acids. J Med Chem. Nov. 1970;13(6):1235-7.

Khomutov et al., Directed synthesis of inhibitors of enzymic changes of glutamic acid. Doklady Akademii Nauk SSSR. 1965;161(5):1227-30. Russian.

Menger et al., Chemical Reaction between Colliding Vesicles. Chem Int Ed Engl. Oct. 15, 2001;40(20):3905-3907.

Munegumi et al., Amidation of carboxyl group involved in *N*-protected amino acids using *O*-benzylhydroxylamine. Peptide Chemistry. 1993;31:49-52.

Patani et al., Bioisosterism: A Rational Approach in Drug Design. Chem Rev. Dec. 19, 1996;96(8):3147-3176.

Singh et al., Chemistry and structure-activity relationship of HIV-1 integrase inhibitor integracide B and related natural products. J Nat Prod. Oct. 2003;66(10):1338-44.

Stowell et al., The synthesis of N-hydroxy-N'-phenyloctanediamide and its inhibitory effect on proliferation of AXC rat prostate cancer cells. J Med Chem. Apr. 14, 1995;38(8):1411-3.

U.S. Appl. No. 60/289,850, filed May 9, 2001, Schreiber et al.

U.S. Appl. No. 60/664,470, filed Mar. 22, 2005, Bradner et al.

U.S. Appl. No. 60/773,172, filed Feb. 14, 2006, Bradner et al.

U.S. Appl. No. 60/773,510, filed Feb. 14, 2006, Bradner et al.

International Search Report and Written Opinion for PCT/US2010/002220 mailed Apr. 27, 2011.

Invitation to Pay Additional Fees for PCT/US2007/062145 mailed Oct. 29, 2007.

International Search Report and Written Opinion for PCT/US2007/062145 mailed Jun. 24, 2008.

International Preliminary Report on Patentability for PCT/US2007/062145 mailed Aug. 28, 2008.

Invitation to Pay Additional Fees for PCT/US2007/062152 mailed Dec. 7, 2007.

International Search Report and Written Opinion for PCT/US2007/062152 mailed Oct. 7, 2008.

International Search Report and Written Opinion for PCT/US2007/062152 mailed Oct. 14, 2008.

International Preliminary Report on Patentability for PCT/US2007/062152 mailed Mar. 19, 2009.

International Search Report and Written Opinion for PCT/US2009/004235 mailed Mar. 4, 2010.

International Preliminary Report on Patentability for PCT/US2009/004235 mailed Feb. 3, 2011.

Supplementary European Search Report for EP 06748614.2 mailed Oct. 16, 2009.

International Search Report and Written Opinion for PCT/US2006/010676 mailed Jul. 14, 2008.

International Preliminary Report on Patentability for PCT/US2006/010676 mailed Mar. 19, 2009.
International Search Report and Written Opinion for PCT/US2007/010587 mailed Jan. 29, 2008.
International Preliminary Report on Patentability for PCT/US2007/010587 mailed Nov. 13, 2008.
International Search Report for PCT/US2002/014835 mailed Dec. 20, 2002.
Written Opinion for PCT/US2002/014835 mailed Aug. 8, 2003.
International Preliminary Exam Report for PCT/US2002/014835 mailed Jun. 4, 2004.
Invitation to Pay Additional Fees for PCT/US1997/005275 mailed Nov. 21, 1997.
International Search Report for PCT/US1997/005275 mailed Feb. 16, 1998.
Written Opinion for PCT/US1997/005275 mailed Mar. 5, 1998.
International Preliminary Examination Report for PCT/US1997/005275 mailed Jul. 3, 1998.
Office Communication, mailed Oct. 15, 2008, for U.S. Appl. No. 11/386,959.
Office Communication, mailed Jul. 21, 2009, for U.S. Appl. No. 11/386,959.
Office Communication, mailed Nov. 17, 2009, for U.S. Appl. No. 11/386,959.
Office Communication, mailed Nov. 28, 2005, for U.S. Appl. No. 10/621,276.
Office Communication, mailed Aug. 8, 2006, for U.S. Appl. No. 10/621,276.
Notice of Allowance, mailed Mar. 6, 2007, for U.S. Appl. No. 10/621,276.
Office Communication, mailed Sep. 16, 2009, for U.S. Appl. No. 11/879,466.
Notice of Allowance, mailed Feb. 4, 2010, for U.S. Appl. No. 11/879,466.
Office Communication, mailed Jan. 21, 1998, for U.S. Appl. No. 08/624,735.
Office Communication, mailed Jan. 17, 2001, for U.S. Appl. No. 08/624,735.
Office Communication, mailed Oct. 10, 2001, for U.S. Appl. No. 08/624,735.
Office Communication, mailed Oct. 16, 2002, for U.S. Appl. No. 08/624,735.
Office Communication, mailed Aug. 12, 2003, for U.S. Appl. No. 08/624,735.
Notice of Allowance, mailed Apr. 13, 2004, for U.S. Appl. No. 08/624,735.
Office Communication, mailed May 6, 2009, for U.S. Appl. No. 10/919,217.
Office Communication, mailed Mar. 4, 2010, for U.S. Appl. No. 10/919,217.
Office Communication, mailed Oct. 14, 2010, for U.S. Appl. No. 10/919,217.
Office Communication, mailed Apr. 8, 2010, for U.S. Appl. No. 12/196,878.
Office Communication, mailed Aug. 10, 2010, for U.S. Appl. No. 12/196,878.
Office Communication, mailed Jan. 18, 2011, for U.S. Appl. No. 12/196,878.
Office Communication, mailed Aug. 5, 2010, for U.S. Appl. No. 12/196,946.
Office. Communication, mailed Dec. 28, 2010, for U.S. Appl. No. 12/196,946.
Advisory Action, mailed Apr. 14, 2011, for U.S. Appl. No. 12/196,946.
Office Communication, mailed Jun. 30, 2003, for U.S. Appl. No. 09/800,187.
Office Communication, mailed Apr. 13, 2004, for U.S. Appl. No. 09/800,187.
Notice of Allowance, mailed Apr. 13, 2007, for U.S. Appl. No. 10/964,313.
Office Communication, mailed Sep. 17, 2009, for U.S. Appl. No. 11/831,303.
Office Communication, mailed Apr. 2, 2010, for U.S. Appl. No. 12/370,390.
Office Communication, mailed Oct. 8, 2010, for U.S. Appl. No. 12/370,390.
Office Communication, mailed Apr. 28, 2011, for U.S. Appl. No. 12/370,390.
GenBank Submission: NIH/NCBI, Accession No. AAA68286; GI: 348052, Henkin et al., Jun. 14, 1995.
GenBank Submission: NIH/NCBI, Accession No. AAD29046, Grozinger et al.; May 6, 1999.
GenBank Submission: NIH/NCBI, Accession No. AAF73428, Buggy et al.; Jun. 1, 2000.
GenBank Submission: NIH/NCBI, Accession No. AAP63491; Kieliszewski; Jun. 12, 2003.
GenBank Submission; NIH/NCBI, Accession No. AB006626; GI:2564323, Ohara et al.; Mar. 18, 1998.
GenBank Submission; NIH/NCBI, Accession No. AB006626; GI:6635126, Ohara et al.; Dec. 25, 1999.
GenBank Submission; NIH/NCBI, Accession No. AF039241, Swensen.; Mar. 11, 2009.
GenBank Submission; NIH/NCBI, Accession No. AF132607, Grozinger et al.; May 6, 1999.
GenBank Submission; NIH/NCBI, Accession No. AF230097, Hu et al., May 31, 2000.
GenBank Submission; NIH/NCBI, Accession No. AF245664, Buggy et al.; Jun. 1, 2000.
GenBank Submission; NIH/NCBI, Accession No. AJ011972, Strom et al.; Oct. 19, 1998.
GenBank Submission: NIH/NCBI, Accession No. BAA25526; GI: 3043724, Ohara et al., Apr. 10, 1998.
GenBank Submission: NIH/NCBI, Accession No. BC009676, Strausberg et al.; Jul. 15, 2006.
GenBank Submission: NIH/NCBI, Accession No. BC111735, Strausberg et al.; Jan. 17, 2006.
GenBank Submission; NIH/NCBI, Accession No. CAA09893.1, Strom et al.; Oct. 7, 2008.
GenBank Submission; NIH/NCBI, Accession No. NM_006044.2, Dhakal et al.; Mar. 15, 2009.
GenBank Submission; NIH/NCBI, Accession No. NM_001015053.1, Seo et al.; Mar. 15, 2009.
GenBank Submission; NIH/NCBI, Accession No. NM_006037.3, Chabane et al.; Mar. 29, 2009.
GenBank Submission; NIH/NCBI, Accession No. NM_014707, Muralidhar et al.; Mar. 11, 2011.
GenBank Submission; NIH/NCBI, Accession No. NM_018486, Bailey et al.; Mar. 11, 2011.
GenBank Submission; NIH/NCBI, Accession No. NM_032019, Bailey et al.; Mar. 12, 2011.
GenBank Submission; NIH/NCBI, Accession No. NM_058176, Muralidhar et al.; Feb. 27, 2011.
GenBank Submission; NIH/NCBI, Accession No. NM_058177, Tam et al.; May 7, 2010.
GenBank Submission; NIH/NCBI, Accession No. NM_178423, Muralidhar et al.; Mar. 13, 2011.
Genbank Submission; NIH/NCBI, Accession No. NM_178425, Muralidhar et al.; Feb. 27, 2011.
GenBank Submission; NIH/NCBI, Accession No. NP_001518, Campos et al.; Mar. 13, 2011.
GenBank Submission; NIH/NCBI, Accession No. NP_004955, Dong et al; Mar. 27, 2011.
GenBank Submission; NIH/NCBI, Accession No. NP_005465, Huynh; Mar. 11, 2011.
GenBank Submission; NIH/NCBI, Accession No. NP_006035; Aldana-Masangkay et al.; Mar. 13, 2011.
GenBank Submission; NIH/NCBI, Accession No. O15739, Loomis et al.; Oct. 31, 2006.
GenBank Submission: NIH/NCBI, Accession No. P56524; GI: 3024889, Ohara et al., Dec. 15, 1998.
GenBank Submission: NIH/NCBI, Accession No. Q48935; GI: 3023317, Sakurada et al., Apr. 20, 2010.
GenBank Submission; NIH/NCBI, Accession No. Q9Z2V5, Verdel et al.; Mar. 2, 2010.

GenBank Submission; NIH/NCBI, Accession No. Q9Z2V6, Verdel et al.; Mar. 2, 2010.
GenBank Submission; NIH/NCBI, Accession No. R64669, Wilson; May 26, 1995.
GenBank Submission; NIH/NCBI, Accession No. U31814, Yang et al.; Nov. 13, 1996.
GenBank Submission; NIH/NCBI, Accession No. U31814, Yang et al.; Nov. 14, 1996.
NCBI annotation project, GenBank Accession No. XM_002252, Oct. 16, 2001.
NCBI annotation project, GenBank Accession No. XM_004963, Feb. 9, 2001.
NCBI annotation project, GenBank Accession No. XM_004963.2, Oct. 16, 2001.
NCBI annotation project, GenBank Accession No. XM_007047, Nov. 16, 2000.
NCBI annotation project, GenBank Accession No. XM_008359, Oct. 16, 2001.
NCBI annotation project, GenBank Accession No. XP_002252, Oct. 16, 2001.
NCBI annotation project, GenBank Accession No. $XP_{13}$ 008359.2, Feb. 10, 2001.
[No Author Listed] Targeting the aggresome with an HDAC6 inhibitor in combination with velcade for myeloma therapy. Cancer Biology and Therapy. 2005;4(7):i-iv.
Abremski et al., Bacteriophage P1 site-specific recombination. Purification and properties of the Cre recombinase protein. J Biol Chem. Feb. 10, 1984;259(3):1509-14.
Adams et al., Initial assessment of human gene diversity and expression patterns based upon 83 million nucleotides of cDNA sequence. Nature. Sep. 28, 1998;377(6547 Suppl):3-174.
Adams, The proteasome: A suitable antineoplastic target. Nat Rev Cancer. May 2004;4(5):349-60.
Afshar et al., Characterization of a human gene with sequence homology to *Saccharomyces cerevisiae* SIR2. Gene. Jun. 24, 1999;234(1):161-8.
Aggarwal et al., Trifluoromethanesulfonic Acid, an Efficient Catalyst for the Hetero Diels-Alder Reaction and an Improved Synthesis of Mefrosol. Tetrahedron Letters. 1997;38:2569-72.
Ahringer, NuRD and SIN3 histone deacetylase complexes in development. Trends Genet. Aug. 2000;16(8):351-6.
Alonso et al., A novel yeast histone deacetylase: partial characterization and development of an activity assay. Biochim Biophys Acta. Mar. 26, 1986;866(2-3):161-9.
Anderson et al., Analytical Techniques in Combinatorial Chemistry: MAS CH Correlation in Solvent-Swollen Resin. J Org Chem. 1995;60:2650-51.
Anklesaria et al., Engraftment of a clonal bone marrow stromal cell line in vivo stimulates hematopoietic recovery from total body irradiation. Proc Natl Acad Sci U S A. Nov. 1987;84(21):7681-5.
Antón et al., Intracellular localization of proteasomal degradation of a viral antigen. J Cell Biol. Jul. 12, 1999;146(1):113-24.
Antonjuk et al., Asymmetric Induction in the Additions of Anions of Allylic Sulfoxides to Benzaldehyde. Aust J Chem. 1980;33:2635-51.
Aparicio et al., Modifiers of position effect are shared between telomeric and silent mating-type loci in *S. cerevisiae*. Cell. Sep. 20, 1991;66(6):1279-87.
Arkin et al., An algorithm for protein engineering: simulations of recursive ensemble mutagenesis. Proc Natl Acad Sci U S A. Aug. 15, 1992;89(16):7811-5.
Attal et al., Single versus double autologous stem-cell transplantation for multiple myeloma. N Engl J Med. Dec. 25, 2003;349(26):2495-502.
Auffray et al., [IMAGE: molecular integration of the analysis of the human genome and its expression.] C R Acad Sci III. Feb. 1995;318(2):263-72. French.
Baer et aL, Eukaryotic RNA polymerase II binds to nucleosome cores from transcribed genes. Nature. Feb. 10, 1983;301(5900):482-8.
Ballestar et al., Methyl-CpG-binding proteins. Targeting specific gene repression. Eur J Biochem. Jan. 2001;268(1):1-6.
Barbas et al., Semisynthetic combinatorial antibody libraries: a chemical solution to the diversity problem. Proc Natl Acad Sci U S A. May 15, 1992;89(10):4457-61.
Bartel et al., Elimination of false positives that arise in using the two-hybrid system. Biotechniques. Jun. 1993;14(6):920-4.
Beck-Sickinger et al., Neuropeptide Y: identification of the binding site. Int J Pept Protein Res. Dec. 1990;36(6):522-30.
Beck-Sickinger et al., Semiautomated T-bag peptide synthesis using 9-fluorenyl-methoxycarbonyl strategy and benzotriazol-1-yl-tetramethyl-uronium tetrafluoroborate activation. Pept Res. Mar.-Apr. 1991;4(2):88-94.
Beck-Sickinger et al., Structure/activity relationships of C-terminal neuropeptide Y peptide segments and analogues composed of sequence 1-4 linked to 25-36. Eur J Biochem. Dec. 12, 1990;194(2):449-56.
Ben-Bassat et al., Processing of the initiation methionine from proteins: properties of the *Escherichia coli* methionine aminopeptidase and its gene structure. J Bacteriol. Feb. 1987;169(2):751-7.
Bennett et al., Global impairment of the ubiquitin-proteasome system by nuclear or cytoplasmic protein aggregates precedes inclusion body formation. Mol Cell. Feb. 4, 2005;17(3):351-65.
Berenbaum et al., What is synergy? Pharmacol Rev. Jun. 1989;41(2):93-141.
Berg et al., Long-Chain Polystyrene-Grafted Polyethylene Film Matrix: A New Support for Solid-Phase Peptide Synthesis. J Am Chem Soc. 1989;111:8024-26.
Berge et al., Pharmaceutical salts. J Pharm Sci. Jan. 1977;66(1):1-19.
Bernstein et al., Genomewide studies of histone deacetylase function in yeast. Proc Natl Acad Sci U S A. Dec. 5, 2000;97(25):13708-13.
Blackwell et al., A one-bead, one-stock solution approach to chemical genetics: part 1. Chem Biol. Dec. 2001;8(12):1167-82.
Blankemeyer-Menge et al., Simultaneous Multiple Synthesis of Protected Peptide Fragments on "Allyl"—Functionalized Cellulose Disc Supports. Tetrahedron Lett. 1988;29:5871-74.
Blondelle et al., Soluble combinatorial libraries of organic, peptidomimetic and peptide diversities. Trends Anal Chem. 1995;14:83-92.
Bolden et al., Anticancer activities of histone deacetylase inhibitorsNat Rev Drug Discov. Sep. 2006;5(9):769-84.
Bolger et al., Intracellular trafficking of histone deacetylase 4 regulates neuronal cell death. J Neurosci. Oct. 12, 2005;25(41):9544-53.
Borchardt et al., Synthetic Receptor Binding Elucidated with an Encoded Combinatorial Library. J Am Chem Soc. 1994;116:373-74.
Bottomley et al., Structural and functional analysis of the human HDAC4 catalytic domain reveals a regulatory structural zinc-binding domain. J Biol Chem. Sep. 26, 2008;283(39):26694-704. Epub Jul. 8, 2008.
Bowdish et al., Analysis of RIM11, a yeast protein kinase that phosphorylates the meiotic activator IME1. Mol Cell Biol. Dec. 1994;14(12):7909-19.
Bowdish et al., Bipartite structure of an early meiotic upstream activation sequence from *Saccharomyces cerevisiae*. Mol Cell Biol. Apr. 1993;13(4):2172-81.
Bowers et al., Synthesis and Conformation-Activity Relationships of the Peptide Isosteres of FK228 and Largazole. J Am Chem Soc. 2009;131:2900-05.
Bowers et al., Total synthesis and biological mode of action of largazole: a potent class I histone deacetylase inhibitor. J Am Chem Soc. Aug. 20, 2008;130(33):11219-22. Epub Jul 19, 2008.
Brachman et al., The SIR2 gene family, conserved from bacteria to humans, functions in silencing, cell cycle progression, and chromosome stability. Genes Dev. Dec. 1, 1995;9(23):2888-902.
Bradley et al., Formation of germ-line chimaeras from embryo-derived teratocarcinoma cell lines. Nature. May 17-23, 1984;309(5965):255-6.
Bradner et al., Chemical phylogenetics of histone deacetylases. Nat Chem Biol. Mar. 2010;6(3):238-243. Epub Feb. 7, 2010.
Branden et al., Chapter 16. Prediction, Engineering, and Design of Protein Structures. In: Introduction to Protein Structure. Garland Publishing Inc., New York. 1991:247.
Braunstein et al., Efficient transcriptional silencing in *Saccharomyces cerevisiae* requires a heterochromatin histone acetylation pattern. Mol Cell Biol. Aug. 1996;16(8):4349-56.
Braunstein et al., Transcriptional silencing in yeast is associated with reduced nucleosome acetylation. Genes Dev. Apr. 1993;7(4):592-604.

Bray et al., Gas Phase Cleavage of Peptides from a Solid Support with Ammonia Vapour. Application in Simultaneous Multiple Peptide Synthesis. Tetrahedron Lett. 1991;32:6163-66.
Bray et al., The Simultaneous Multiple Production of Solution Phase Peptides; Assessment of the Geysen Method of Simultaneous Peptide Synthesis. Tetrahedron Lett. 1990;31:5811-14.
Brenner et al., Encoded combinatorial chemistry. Proc Natl Acad Sci U S A. Jun. 15, 1992;89(12):5381-3.
Brinster et al., Factors affecting the efficiency of introducing foreign DNA into mice by microinjecting eggs. Proc Natl Acad Sci U S A. Jul. 1985;82(13):4438-42.
Brownell et al., Tetrahymena histone acetyltransferase A: a homolog to yeast Gcn5p linking histone acetylation to gene activation. Cell. Mar. 22, 1996;84(6):843-51.
Brummel et al., A mass spectrometric solution to the address problem of combinatorial libraries. Science. Apr. 15, 1994;264(5157):399-402.
Brunet et al., Nuclear translocation of p42/p44 mitogen-activated protein kinase is required for growth factor-induced gene expression and cell cycle entry. Embo J. Feb. 1, 1999;18(3):664-74.
Buiting et al., Detection of aberrant DNA methylation in unique Prader-Willi syndrome patients and its diagnostic implications. Hum Mol Genet. Jun. 1994;3(6):893-5.
Burbaum et al., A paradigm for drug discovery employing encoded combinatorial libraries. Proc Natl Acad Sci U S A . Jun. 20, 1995;92(13):6027-31.
Burbelo et al., 14-3-3 proteins. Hot numbers in signal transduction. Curr Biol. Feb. 1, 1995;5(2):95-6.
Byrd et al., Depsipeptide (FR901228): a novel therapeutic agent with selective, in vitro activity against human B-cell chronic lymphocytic leukemia cells. Blood. Aug. 15, 1999;94(4):1401-8.
Cali et al., Nucleotide sequence of a cDNA encoding the human muscle-specific enolase (MSE). Nucleic Acids Res. Apr. 11, 1990;18(7):1893.
Cameron, Recent advances in transgenic technology. Mol Biotechnol. Jun. 1997;7(3):253-65.
Carmen et al., HDA1 and HDA3 are components of a yeast histone deacetylase (HDA) complex. J Biol Chem. Jun. 28, 1996;271(26):15837-44.
Catley et al., NVP-LAQ824 is a potent novel histone deacetylase inhibitor with significant activity against multiple myeloma. Blood. Oct. 1, 2003;102(7):2615-22. Epub Jun. 19, 2003.
Cavenee et al., Expression of recessive alleles by chromosomal mechanisms in retinoblastoma. Nature. Oct. 27-Nov. 2, 1983;305(5937):779-84.
Chauhan et al., Blockade of Hsp27 overcomes Bortezomib/proteasome inhibitor PS-341 resistance in lymphoma cells. Cancer Res. Oct. 1, 2003;63(19):6174-7.
Chauhan et al., HSP27 inhibits release of mitochondrial protein Smac in multiple myeloma cells and confers dexamethasone resistance. Blood. Nov. 1, 2003;102(9):3379-86. Epub Jul. 10, 2003.
Chen et al., "Analogous" Organic Synthesis of Small-Compound Libraries: Validation of Combinatorial Chemistry in Small-Molecule Synthesis. JACS. 1994;116:2661-62.
Chen et al., Gene therapy for brain tumors: regression of experimental gliomas by adenovirus-mediated gene transfer in vivo. Proc Natl Acad Sci U S A. Apr. 12, 1994;91(8):3054-7.
Chu et al., Free Solution Identification of Candidate Peptides from Combinatorial Libraries by Affinity Capillary Electrophoresis/Mass Spectrometry. J Am Chem Soc. 1995;117:5419-20.
Clackson et al., Making antibody fragments using phage display libraries. Nature. Aug. 15, 1991;352(6336):624-8.
Clemons et al., A one-bead, one-stock solution approach to chemical genetics: part 2. Chem Biol. Dec. 2001;8(12):1183-95.
Clipstone et al., Identification of calcineurin as a key signalling enzyme in T-lymphocyte activation. Nature. Jun. 25, 1992;357(6380):695-7.
Cockell et al., Nuclear compartments and gene regulation. Curr Opin Genet Dev. Apr. 1999;9(2):199-205.
Cohen et al., The histone deacetylase HDAC4 connects neural activity to muscle transcriptional reprogramming. J Biol Chem. Nov. 16, 2007;282(46):33752-9. Epub Sep. 16, 2007.
Corcoran et al., A novel action of histone deacetylase inhibitors in a protein aggresome disease model. Curr Biol. Mar. 23, 2004;14(6):488-92.
Cress et al., Histone deacetylases, transcriptional control, and cancer. J Cell Physiol. Jul. 2000;184(1):1-16.
Csordas, On the biological role of histone acetylation. Biochem J. Jan. 1, 1990;265(1):23-38.
Cuperus et al., Locus specificity determinants in the multifunctional yeast silencing protein Sir2. EMBO J. Jun. 1, 2000;19(11):2641-51.
Curtin et al., Succinimide hydroxamic acids as potent inhibitors of histone deacetylase (HDAC). Bioorg Med Chem Lett. Oct. 21, 2002;12(20):2919-23.
Cwirla et al., Peptides on phage: a vast library of peptides for identifying ligands. Proc Natl Acad Sci U S A. Aug. 1990;87(16):6378-82.
Dangond et al., Differential display cloning of a novel human histone deacetylase (HDAC3) cDNA from PHA-activated immune cells. Biochem Biophys Res Commun. Jan. 26, 1998;242(3):648-52.
Dann et al., Human renin: a new class of inhibitors. Biochem Biophys Res Commun. Jan. 14, 1986;134(1):71-7.
David et al., Histone deacetylase associated with mSin3A mediates repression by the acute promyelocytic leukemia-associated PLZF protein. Oncogene. May 14, 1998;16(19):2549-56.
Davie et al., Multiple functions of dynamic histone acetylation. J Cell Biochem. May 1994;55(1):98-105.
De Ruijter et al., Histone deacetylases (HDACs): characterization of the classical HDAC family. Biochem J. Mar. 15, 2003;370(Pt 3):737-49.
Delgrave et al., Recursive ensemble mutagenesis. Protein Engineer. 1993;6(3):327-31.
Denlinger et al., Proteasome inhibition sensitizes non-small cell lung cancer to histone deacetylase inhibitor-induced apoptosis through the generation of reactive oxygen species. J Thorac Cardiovasc Surg. Nov. 2004;128(5):740-8.
Dev et al., Electrochemotherapy—a novel method of cancer treatment. Cancer Treat Rev. Jan. 1994;20(1):105-15.
Devlin et al., Random peptide libraries: a source of specific protein binding molecules. Science. Jul. 27, 1990;249(4967):404-6.
Dower et al., Chapter 28. The Search for Molecular Diversity (II): Recombinant and Synthetic Randomized Peptide Libraries. Annu Rep Med Chem. 1991;26:271-80.
Dul et al., Hsp70 and antifibrillogenic peptides promote degradation and inhibit intracellular aggregation of amyloidogenic light chains. J Cell Biol. Feb. 19, 2001;152(4):705-15.
Egner et al., Solid Phase Chemistry: Direct Monitoring by Matrix-Assisted Laser Desorption/Ionization Time of Flight Mass Spectrometry. A Tool for Combinatorial Chemistry. J Org Chem. 1995;60:2652-53.
Eichler et al., Application of Cellulose Paper as Support Material in Simultaneous Solid Phase Peptide Synthesis. Collect Czech Chem Commun. 1989;54:1746-52.
Eichler et al., Evaluation of cotton as a carrier for solid-phase peptide synthesis. Pept Res. Sep.-Oct. 1991;4(5):296-307.
Ellison et al., Epitope-tagged ubiquitin. A new probe for analyzing ubiquitin function. J Biol Chem. Nov. 5, 1991;266(31):21150-7.
Emiliani et al., Characterization of a human RPD3 ortholog, HDAC3. Proc Natl Acad Sci U S A. Mar. 17, 1998;95(6):2795-800.
Evans et al., An engineered poliovirus chimaera elicits broadly reactive HIV-1 neutralizing antibodies. Nature. Jun. 1, 1989;339(6223):385-8.
Evans et al., Establishment in culture of pluripotential cells from mouse embryos. Nature. Jul. 9, 1981;292(5819):154-6.
Ewenson et al., Ketomethylene pseudopeptide analogues of substance P: synthesis and biological activity. J Med Chem. Feb. 1986;29(2):295-9.
Fabian et al., A small molecule-kinase interaction map for clinical kinase inhibitors. Nat Biotechnol. Mar. 2005;23(3):329-36. Epub Feb. 13, 2005.
Fabunmi et al., Activity and regulation of the centrosome-associated proteasome. J Biol Chem. Jan. 7, 2000;275(1):409-13.

Feling et al., Salinosporamide A: a highly cytotoxic proteasome inhibitor from a novel microbial source, a marine bacterium of the new genus *salinospora*. Angew Chem Int Ed Engl. Jan. 20, 2003;42(3):355-7.
Felsenfeld, Chromatin as an essential part of the transcriptional mechanism. Nature. Jan. 16, 1992;355(6357):219-24.
Feng et al., Progressive sequence alignment as a prerequisite to correct phylogenetic trees. J Mol Evol. 1987;25(4):351-60.
Finnin et al., Structures of a histone deacetylase homologue bound to the TSA and SAHA inhibitors. Nature. Sep. 9, 1999;401(6749):188-93.
Fischle et al., A new family of human histone deacetylases related to *Saccharomyces cerevisiae* HDA1p. J Biol Chem. Apr. 23, 1999;274(17):11713-20.
Fitch, Distinguishing Homologous from Analogous Proteins. Syst Zool 1970;19:99-113.
Fitch et al., High-Resolution $^1$H NMR in Solid-Phase Organic Synthesis. J Org Chem. 1994;59:7955-56.
Fleming et al., The total synthesis of ( )-trichostatin A: Some observations on the acylation and alkylation of silyl enol ethers, silyl dienol ethers and a silyl trienol ether. Tetrahedron. 1983;39:841-46.
Fodor et al., Light-directed, spatially addressable parallel chemical synthesis. Science. Feb. 15, 1991;251(4995):767-73.
Frank et al., Simultaneous Multiple Peptide Synthesis Under Continuous Flow Conditions on Cellulose Paper Discs as Segmental Solid Supports. Tetrahedron. 1988;44:6031-40.
Frank et al., Spot-Synthesis: An Easy Technique for the Positionally Addressable, Parallel Chemical Synthesis on a Membrane Support. Tetrahedron. 1992;48:9217-32.
Frank et al., Strategies and Techniques in Simultaneous Solid Phase Synthesis Based on the Segmentation of Membrane Type Supports. Bioorg Med Chem Lett. 1993;3:425-30.
Friend et al., Deletions of a DNA sequence in retinoblastomas and mesenchymal tumors: organization of the sequence and its encoded protein. Proc Natl Acad Sci U S A. Dec. 1987;84(24):9059-63.
Frye et al., Characterization of Five Human cDNAs with Homology to the Yeast SIR2 Gene: Sir2-like Proteins (Sirtuins) Metabolize NAD and May Have Protein ADP-Ribosyltransferase Activity. Biochem Biophys Res Commun. 1999;260:273-79.
Frye, Phylogenetic classification of prokaryotic and eukaryotic Sir2-like proteins. Biochem Biophys Res Commun. Jul. 5, 2000;273(2):793-8.
Furukawa et al., Isolation and mapping of a human gene (RPD3L1) that is homologous to RPD3, a transcription factor in *Saccharomyces cerevisiae*. Cytogenet Cell Genet. 1996;73(1-2):130-3.
Furumai et al., Potent histone deacetylase inhibitors built from trichostatin A and cyclic tetrapeptide antibiotics including trapoxin. Proc Natl Acad Sci U S A. Jan. 2, 2001;98(1):87-92.
Gallop et al., Applications of combinatorial technologies to drug discovery. 1. Background and peptide combinatorial libraries. J Med Chem. Apr. 29, 1994;37(9):1233-51.
Gammon et al., T cell determinant structure: cores and determinant envelopes in three mouse major histocompatibility complex haplotypes. J Exp Med. Mar. 1, 1991;173(3):609-17.
García-Mata et al., Characterization and dynamics of aggresome formation by a cytosolic GFP-chimera. J Cell Biol. Sep. 20, 1999;146(6):1239-54.
Garcia-Mata et al., Hassles with taking out the garbage: aggravating aggresomes. Traffic. Jun. 2002;3(6):388-96.
Garcia-Ramirez et al., Role of the histone “tails” in the folding of oligonucleosomes depleted of histone H1. J Biol Chem. Sep. 25, 1992;267(27):19587-95.
Gardlik et al., Vectors and delivery systems in gene therapy. Med Sci Monit. Apr. 2005;11(4):RA110-21. Epub Mar. 24, 2005.
Gartenberg, The Sir proteins of *Saccharomyces cerevisiae*: mediators of transcriptional silencing and much more. Curr Opin Microbiol. Apr. 2000;3(2):132-7.
Gelmetti et al., Aberrant recruitment of the nuclear receptor corepressor-histone deacetylase complex by the acute myeloid leukemia fusion partner ETO. Mol Cell Biol. Dec. 1998;18(12):7185-91.
Geysen et al., Use of peptide synthesis to probe viral antigens for epitopes to a resolution of a single amino acid. Proc Natl Acad Sci U S A. Jul. 1984;81(13):3998-4002.
Gordon et al., Applications of combinatorial technologies to drug discovery. 2. Combinatorial organic synthesis, library screening strategies, and future directions. J Med Chem. May 13, 1994;37(10):1385-401.
Gordon et al., Design of peptide derived amino alcohols as transition-state analog inhibitors of angiotensin converting enzyme. Biochem Biophys Res Commun. Jan. 16, 1985;126(1):419-26.
Görlich, Nuclear protein import. Curr Opin Cell Biol. Jun. 1997;9(3):412-9.
Gossler et al., Transgenesis by means of blastocyst-derived embryonic stem cell lines. Proc Natl Acad Sci U S A. Dec. 1986;83(23):9065-9.
Goy et al., Phase II study of proteasome inhibitor bortezomib in relapsed or refractory B-cell non-Hodgkin’s lymphoma. J Clin Oncol. Feb. 1, 2005;23(4):667-75. Epub Dec. 21, 2004.
Gray et al., The human histone deacetylase family. Exp Cell Res. Jan. 15, 2001;262(2):75-83.
Green, When the products of oncogenes and anti-oncogenes meet. Cell. Jan. 13, 1989;56(1):1-3.
Gregoretti et al., Molecular evolution of the histone deacetylase family: functional implications of phylogenetic analysisJ Mol Biol. Apr. 16, 2004;338(1):17-31.
Gregory et al., Combination chemotherapy versus melphalan and prednisolone in the treatment of multiple myeloma: an overview of published trials. J Clin Oncol. Feb. 1992;10(2):334-42.
Griffiths et al., Human anti-self antibodies with high specificity from phage display libraries. Embo J. Feb. 1993;12(2):725-34.
Grignani et al., Fusion proteins of the retinoic acid receptor-alpha recruit histone deacetylase in promyelocytic leukaemia. Nature. Feb. 19, 1998;391(6669):815-8.
Grozinger et al., Deacetylase enzymes: biological functions and the use of small-molecule inhibitors. Chem Biol. Jan. 2002;9(1):3-16.
Grozinger et al., Regulation of histone deacetylase 4 and 5 and transcriptional activity by 14-3-3-dependent cellular localization. Proc Natl Acad Sci U S A. Jul. 5, 2000;97(14):7835-40.
Grozinger et al., Three proteins define a class of human histone deacetylases related to yeast Hadlp. Proc Natl Acad Sci U S A. Apr. 27, 1999;96(9):4868-73.
Grunstein, Histone acetylation in chromatin structure and transcription. Nature. Sep. 25, 1997;389(6649):349-52.
Grunstein, Molecular model for telomeric heterochromatin in yeast. Curr Opin Cell Biol. Jun. 1997;9(3):383-7.
Gu et al., Activation of p53 sequence-specific DNA binding by acetylation of the p53 C-terminal domain. Cell. Aug. 22, 1997;90(4):595-606.
Guarente, Sir2 links chromatin silencing, metabolism, and aging. Genes Dev. May 1, 2000;14(9):1021-6.
Guo et al., Protein tolerance to random amino acid change. Proc Natl Acad Sci U S A. Jun. 22, 2004; 101(25):9205-10. Epub Jun. 14, 2004.
Habig et al., Glutathione S-transferases. The first enzymatic step in mercapturic acid formation. J Biol Chem. Nov. 25, 1974;249(22):7130-9.
Haggarty et al., Dissecting cellular processes using small molecules: identification of colchicine-like, taxol-like and other small molecules that perturb mitosis. Chem Biol. Apr. 2000;7(4):275-86.
Haggarty et al., Domain-selective small-molecule inhibitor of histone deacetylase 6 (HDAC6)—mediated tubulin deacetylation. Proc Natl Acad Sci U S A. Apr. 15, 2003;100(8):4389-94. Epub Apr. 3, 2003.
Haggarty et al., Mapping chemical space using molecular descriptors and chemical genetics: deacetylase inhibitors. Comb Chem High Throughput Screen. Nov. 2004;7(7):669-76.
Haggarty et al., Multidimensional chemical genetic analysis of diversity-oriented synthesis-derived deacetylase inhibitors using cell-based assays. Chem Biol. May 2003;10(5):383-96.
Hansen et al., Retinoblastoma and the progression of tumor genetics. Trends Genet. May 1988;4(5):125-8.
Hardwick et al., Rapamycin-modulated transcription defines the subset of nutrient-sensitive signaling pathways directly controlled by the Tor proteins. Proc Natl Acad Sci U S A. Dec. 21, 1999;96(26):14866-70.

Hassig et al., A role for histone deacetylase activity in HDAC1-mediated transcriptional repression. Proc Natl Acad Sci U S A. Mar. 31, 1998;95(7):3519-24.
Hassig et al., Histone deacetylase activity is required for full transcriptional repression by mSin3A. Cell. May 2, 1997;89(3):341-7.
Hassig et al., Nuclear histone acetylases and deacetylases and transcriptional regulation: HATs off to HDACs. Curr Opin Chem Biol. Oct. 1997;l(3):300-8.
Hathaway et al., Dissecting cell biology with chemical scalpels. Curr Opin Cell Biol. Feb. 2005;17(1):12-9.
Hay et al., Histone deacetylase. Association with a nuclease resistant, high molecular weight fraction of HeLa cell chromatin. J Biol Chem. Mar. 25, 1983;258(6):3726-34.
Hayes et al., Histones H2A/H2B inhibit the interaction of transcription factor IIIA with the *Xenopus borealis* somatic 5S RNA gene in a nucleosome. Proc Natl Acad Sci U S A. Feb. 15, 1992;89(4):1229-33.
He et al., Distinct interactions of PML-RARalpha and PLZF-RARalpha with co-repressors determine differential responses to RA in APL. Nat Genet. Feb. 1998;18(2):126-35.
Hecht et al., Histone H3 and H4 N-termini interact with SIR3 and SIR4 proteins: a molecular model for the formation of heterochromatin in yeast. Cell. Feb. 24, 1995;80(4):583-92.
Hicks et al., Protein import into the nucleus: an integrated view. Annu Rev Cell Dev Biol. 1995;11:155-88.
Hideshima et al., Antitumor activity of lysophosphatidic acid acyltransferase-beta inhibitors, a novel, class of agents, in multiple myeloma. Cancer Res. Dec. 1, 2003;63(23):8428-36.
Hideshima et al., Molecular mechanisms mediating antimyeloma activity of proteasome inhibitor PS-341. Blood. Feb. 15, 2003;101(4):1530-4. Epub Sep. 26, 2002.
Hideshima et al., Molecular mechanisms of novel therapeutic approaches for multiple myeloma. Nat Rev Cancer. Dec. 2002;2(12):927-37.
Hideshima et al., NF-κB as a therapeutic target in multiple myeloma. J Biol Chem. May 10, 2002;277(19):16639-47. Epub Feb. 28, 2002.
Hideshima et al., Novel therapeutic approaches for multiple myeloma. Immunol Rev. Aug. 2003;194:164-76.
Hideshima et al., p38 MAPK inhibition enhances PS-341 (bortezomib)—induced cytotoxicity against multiple myeloma cells. Oncogene. Nov. 18, 2004;23(54):8766-76.
Hideshima et al., Proteasome inhibitor PS-341 abrogates IL-6 triggered signaling cascades via caspase-dependent downregulation of gp130 in multiple myeloma. Oncogene. Nov. 20, 2003;22(52);8386-93.
Hideshima et al., Small-molecule inhibition of proteasome and aggresome function induces synergistic antitumor activity in multiple myeloma. Proc Natl Acad Sci U S A. Jun. 14, 2005;102(24):8567-72. EPUB Jun. 3, 2005.
Hideshima et al., The proteasome inhibitor PS-341 inhibits growth, induces apoptosis, and overcomes drug resistance in human multiple myeloma cells. Cancer Res. Apr. 1, 2001;61(7):3071-6.
Hideshima et al., The role of tumor necrosis factor alpha in the pathophysiology of human multiple myeloma: therapeutic applications. Oncogene. Jul. 27, 2001;20(33):4519-27.
Hochuli et al., New metal chelate adsorbent selective for proteins and peptides containing neighbouring histidine residues. J Chromatogr. Dec. 18, 1987;411:177-84.
Houdebine, The methods to generate transgenic animals and to control transgene expression. J Biotechnol. Sep. 25, 2002;98(2-3):145-60.
Houghten, General method for the rapid solid-phase synthesis of large numbers of peptides: specificity of antigen-antibody interaction at the level of individual amino acids. Proc Natl Acad Sci U S A. Aug. 1985;82(15):5131-5.
Houghten et al., Simplified procedure for carrying out simultaneous multiple hydrogen fluoride cleavages of protected peptide resins. Int J Pept Protein Res. Jun. 1986;27(6):673-8.
Hu et al., Cloning and characterization of a novel human class I histone deacetylase that functions as a transcription repressor. J Biol Chem. May 19, 2000;275(20):15254-64.
Huang et al., Nuclear receptor corepressors partner with class II histone deacetylases in a Sin3-independent repression pathway. Genes Dev. Jan. 1, 2000;14(1):45-54.
Huang et al., Vaccinia virus recombinants expressing an 11-kilodalton beta-galactosidase fusion protein incorporate active beta-galactosidase in virus particles. J Virol. Oct. 1988;62(10):3855-61.
Hubbert et al., HDAC6 is a microtubule-associated deacetylase. Nature. May 23, 2002;417(6887):455-8.
Hunter et al., An Enantioselective Synthesis of Benzylidene-Protected syn-3,5-Dihydroxy Carboxylate Esters via Osmium, Palladium, and Base Catalysis. Org Letter. 2001;3(7):1049-52.
Ike et al., Solid phase synthesis of polynucleotides. VIII. Synthesis of mixed oligodeoxyribonucleotides by the phosphotriester solid phase method. Nucleic Acids Res. Jan. 25, 1983;11(2):477-88.
Imai et al., Transcriptional silencing and longevity protein Sir2 is an NAD-dependent histone deacetylase. Nature. Feb. 17, 2000;403(6771):795-800.
Imamoto et al., Preparation and Synthetic Use of Trimethylsilyl Polyphosphate. A New Stereoselective Aldol-Type Reaction in the Presence of Trimethylsilyl Polyphosphate. J Org Chem. 1984;49:1105-10.
Imamoto et al., The Reaction of Aryl Methyl Ketones with Aromatic Aldehydes in Trimethylsilyl Polyphosphate (PPSE). Formation of MESO-2,4,6-Trisubstituted-5-ACYL-1,3-Dioxl. Tetrahedron Letters. 1982;23(14):1467-70.
Imhof et al., Acetylation of general transcription factors by histone acetyltransferases. Curr Biol. Sep. 1, 1997;7(9):689-92.
Itakura et al., Expression in *Escherichia coli* of a Chemically Synthesized Gene for the Hormone Somatostatin. Science. 1984;198:1056-63.
Itakura et al., Synthesis and use of synthetic oligonucleotides. Annu Rev Biochem. 1984;53:323-56.
Iwabuchi et al., Use of the two-hybrid system to identify the domain of p53 involved in oligomerization. Oncogene. Jun. 1993;8(6):1693-6.
Jacobs et al., Combinatorial chemistry—applications of light-directed chemical synthesis. Trends Biotechnol. Jan. 1994;12(1):19-26.
Jaenisch, Germ line integration and Mendelian transmission of the exogenous Moloney leukemia virus. Proc Natl Acad Sci U S A. Apr. 1976;73(4):1260-4.
Jaenisch, Transgenic animals. Science. Jun. 10, 1988;240(4858):1468-74.
Jähner et al., De novo methylation and expression of retroviral genomes during mouse embryogenesis. Nature. Aug. 12, 1982;298(5875):623-8.
Jähner et al., Insertion of the bacterial gpt gene into the germ line of mice by retroviral infection. Proc Natl Acad Sci U S A. Oct. 1985;82(20):6927-31.
Janknecht et al., Rapid and efficient purification of native histidine-tagged protein expressed by recombinant vaccinia virus. Proc Natl Acad Sci U S A. Oct. 15, 1991;88(20):8972-6.
Jin et al., Transcriptional regulation of the MDR1 gene by histone acetyltransferase and deacetylase is mediated by NF-Y. Mol Cell Biol. Jul. 1998;18(7):4377-84.
Johnson et al., Deacetylase activity associates with topoisomerase II and is necessary for etoposide-induced apoptosis. J Biol Chem. Feb. 16, 2001;276(7):4539-42. Epub Jan. 2, 2001.
Johnson et al., Genetic evidence for an interaction between SIR3 and histone H4 in the repression of the silent mating loci in *Saccharomyces cerevisiae*. Proc Natl Acad Sci U S A. Aug. 1990;87(16):6286-90.
Johnson et al., Molecular cloning of Drosophila melanogaster cDNAs that encode a novel histone deacetylase dHDAC3. Gene. Oct. 9, 1998;221(1):127-34.
Johnston et al., Aggresomes: a cellular response to misfolded proteins. J Cell Biol. Dec. 28, 1998;143(7):1883-98.
Johnstone, Histone-deacetylase inhibitors: novel drugs for the treatment of cancer. Nat Rev Drug Discov. Apr. 2002;1(4):287-99.
Jones et al., Probing the elusive catalytic activity of vertebrate class IIa histone deacetylases. Bioorg Med Chem Lett. Mar. 15, 2008;18(6):1814-9. Epub Feb. 14, 2008.
Jung et al., Amide analogues of trichostatin A as inhibitors of histone deacetylase and inducers of terminal cell differentiation. J Med Chem. Nov. 4, 1999;42(22):4669-79.

Junn et al., Parkin accumulation in aggresomes due to proteasome impairment. J Biol Chem. Dec. 6, 2002;277(49):47870-7. Epub Oct. 2, 2002.
Kao et al., Isolation of a novel histone deacetylase reveals that class I and class II deacetylases promote SMRT-mediated repression. Genes Dev. Jan. 1, 2000;14(1):55-66.
Kappel et al., Regulating gene expression in transgenic animals. Curr Opin Biotechnol. Oct. 1992;3(5):548-53.
Katoh et al., MAFFT: A novel method for rapid multiple sequence alignment based on fast Fourier transform. Nucleic Acids Res. Jul. 15, 2002;30(14):3059-66.
Kawaguchi et al., The deacetylase HDAC6 regulates aggresome formation and cell viability in response to misfolded protein stress. Cell. Dec. 12, 2003;115(6):727-38.
Kennedy et al., Redistribution of silencing proteins from telomeres to the nucleolus is associated with extension of life span in *S. cerevisiae.* Cell. May 2, 1997;89(3):381-91.
Kerr et al., Encoded Combinatorial Peptide Libraries Containing Non-Natural Amino Acids. J Am Chem, Soc. 1993;115:2529-31.
Khockbin et al., Functional significance of histone deacetylase diversity. Curr Opin Genet Dev. Apr. 2001;11(2):162-6.
Kijima et al., Trapoxin, an antitumor cyclic tetrapeptide, is an irreversible inhibitor of mammalian histone deacetylase. J Biol Chem. Oct. 25, 1993;268(30):22429-35.
Kikuchi et al., Multiplicity of histone deacetylase from calf thymus. FEBS Lett. Feb. 1, 1973;29(3):280-282.
Kleff et al., Identification of a gene encoding a yeast histone H4 acetyltransferase. J Biol Chem. Oct. 20, 1995;270(42):24674-7.
Koeller et al., Chemical genetic modifier screens: small molecule trichostatin suppressors as probes of intracellular histone and tubulin acetylation. Chem Biol. May 2003;10(5):397-410.
Kohler et al., Continuous cultures of fused cells secreting antibody of predefined specificity. Nature. Aug. 7, 1975;256(5517):495-7.
Kopito et al., Aggresomes and Russell bodies. Symptoms of cellular indigestion? EMBO Rep. Sep. 2000;1(3):225-31.
Kopito, Aggresomes, inclusion bodies and protein aggregation. Trends Cell Biol. Dec. 2000;10(12):524-30.
Kouzarides, Acetylation: a regulatory modification to rival phosphorylation? EMBO J. Mar. 15, 2000;19(6):1176-9.
Kozbar et al., The production of monoclonal antibodies from human lymphocytes. Immunology Today. 1983;4:72-79.
Krieger et al., Chemical studies of histone acetylation. Substrate specificity of a histone deacetylase from calf thymus nuclei. J Biol Chem. Jan. 10, 1974;249(1):332-4.
Kumar et al., MEGA: A biologist-centric software for evolutionary analysis of DNA and protein sequences. Brief Bioinform. Jul. 2008;9(4):299-306. Epub Apr. 16, 2008.
Kuruvilla et al., Dissecting glucose signaling with diversity-oriented synthesis and small-molecule microarrays. Nature. Apr. 11, 2002;416(6881):653-7.
Kwon et al., Depudecin induces morphological reversion of transformed fibroblasts via the inhibition of histone deacetylase. Proc Natl Acad Sci U S A. Mar. 31, 1998;95(7):3356-61.
Lahm et al., Unraveling the hidden catalytic activity of vertebrate class IIa histone deacetylases. Proc Natl Acad Sci U S A. Oct. 30, 2007;104(44):17335-40. Epub Oct. 23, 2007.
Lam et al., The "One-Bead-One-Compound" Combinatorial Library Method. Chem Rev. Apr. 1, 1997;97(2):411-48.
Landegren et al., A ligase-mediated gene detection technique. Science. Aug. 26, 1988;241(4869):1077-80.
Landry et al., The silencing protein SIR2 and its homologs are NAD-dependent protein deacetylases. Proc Natl Acad Sci U S A. May 23, 2000;97(11):5807-11.
Lasko et al., Targeted oncogene activation by site-specific recombination in transgenic mice. Proc Natl Acad Sci U S A. Jul. 15, 1992;89(14):6232-6.
Lee et al., A positive role for histone acetylation in transcription factor access to nucleosomal DNA. Cell. Jan. 15, 1993;72(1):73-84.
Lee et al., A Strategy for Macrocyclic Ring Closure and Functionalization Aimed toward Split-Pool Syntheses. J Am Chem Soc. 1999;121(45):10648-49.
Lee et al., Histone acetyltransferase complexes: one size doesn't fit all. Nat Rev Mol Cell Biol. Apr. 2007;8(4):284-95.
Lee et al., Proteasome inhibitors disrupt the unfolded protein response in myeloma cells. Proc Natl Acad Sci U S A. Aug. 19, 2003;100(17):9946-51. Epub Aug. 5, 2003.
Lin et al., Generation and Aldol Reaction of Endlate Anion Adjacnet to a η3-Allyl-Mo(Co)$^2$Cp Moiety. A New Approach to the Stereoselctive Synthesis of 1,3,5-Triol and 2-Vinyl-3-Hydroxyl-Tetrahydrofuran. Tetrahedron Letters.1990;31(52):7645-48.
Lin et al., Role of the histone deacetylase complex in acute promyelocytic leukaemia. Nature. Feb. 19, 1998;391(6669):811-4.
Lizcano et al., Cell type-specific roles of histone deacetylase in TR ligand-independent transcriptional repression. Mol Cell Endocrinol. Feb. 14, 2001;172(1-2):13-20.
Look et al., Methods for Combinatorial Organic Synthesis: The Use of Fast $^{13}$C NMR Analysis for Gel Phase Reaction Monitoring. J Org Chem. 1994;59:7588-90.
Lopez-Girona et al., Nuclear localization of Cdc25 is regulated by DNA damage and a 14-3-3 protein. Nature. Jan. 14, 1999;397(6715):172-5.
Luger et al., Crystal structure of the nucleosome core particle at 2.8 A resolution. Nature. Sep. 18, 1997;389(6648):251-60.
Lutterbach et al., ETO, a target of t(8;21) in acute leukemia, interacts with the N-CoR and mSin3 corepressors. Mol Cell Biol. Dec. 1998;18(12):7176-84.
Macbeath et al., Printing proteins as microarrays for high-throughput function determination. Science. Sep. 8, 2000;289(5485):1760-3.
Macherla et al., Structure-activity relationship studies of salinosporamide A (NPI-0052), a novel marine derived proteasome inhibitor. J Med Chem. Jun. 2, 2005;48(11):3684-7.
Maddry et al., Inhibition of the Her2 Tyrosine Kinase and Characterization of a Hydrophobic Site Near the Nucleotide Binding Domain. Bioorganic Med Chem Letter. 1997;7(16):2109-14.
Madura et al., N-recognin/Ubc2 interactions in the N-end rule pathway. J Biol Chem. Jun. 5, 1993;268(16):12046-54.
Maeji et al., Multi-pin peptide synthesis strategy for T cell determinant analysis. J Immunol Methods. Nov. 6, 1990;134(1):23-33.
Magnaghi-Jaulin et al., Retinoblastoma protein represses transcription by recruiting a histone deacetylase. Nature. Feb. 5, 1998;391(6667):601-4.
Mahboobi et al., Design of chimeric histone deacetylase- and tyrosine kinase-inhibitors: a series of imatinib hybrides as potent inhibitors of wild-type and mutant BCR-ABI, PDGF-Rbeta, and histone deacetylases. J Med Chem. Apr. 23, 2009;52(8):2265-79.
Manetto et al., Selective presence of ubiquitin in intracellular inclusions. Am J Pathol. Mar. 1989;134(3):505-13.
Marcand et al., Silencing of genes at nontelomeric sites in yeast is controlled by sequestration of silencing factors at telomeres by Rap 1 protein. Genes Dev. Jun. 1, 1996;10(11):1297-309.
Marks et al., Histone deacetylases and cancer: causes and therapies. Nat Rev Cancer. Dec. 2001;1(3):194-202.
Marks et al., Histone deacetylases. Curr Opin Pharmacol. Aug. 2003;3(4):344-51.
Marks et al., Molecular evolution of proteins on filamentous phage. Mimicking the strategy of the immune system. J Biol Chem. Aug. 15, 1992;267(23):16007-10.
Marmuse et al., "Click chemistry"en route to pseudo-starch. Org Biomol Chem. Jun. 21, 2005;3(12):2225-7. Epub May 11, 2005.
Martinelli et al., Molecular therapy for multiple myeloma. Haematologica. Sep. 2001:86(9):908-17.
Marushige et al., Template properties of liver chromatin. J Mol Biol. Jan. 1996;15(1):160-74.
Marx et al., Bench to bedside: the development of rapamycin and its application to stent restenosis. Circulation. Aug. 21, 2001;104(8):852-5.
Massa et al., Synthesis and antimicrobial and cytotoxic activities of pyrrole-containing analogues of trichostatin A. J Med Chem. Oct. 1990;33(10):2845-9.
McKenzie et al., The centromere and promoter factor, 1, CPF1, of *Saccharomyces cerevisiae* modulates gene activity through a family of factors including SPT21, RPDI (SIN3), RPD3 and CCR4. Mol Gen Genet. Sep. 1993;240(3):374-86.
Megee et al., Genetic analysis of histone H4: essential role of lysines subject to reversible acetylation. Science. Feb. 16, 1990;247(4944):841-5.

Meinke et al., Histone deacetylase: a target for antiproliferative and antiprotozoal agents. Curr Med Chem. Feb. 2001;8(2):211-35.
Meinke et al., Synthesis of apicidin-derived quinolone derivatives: parasite-selective histone deacetylase inhibitors and antiproliferative agents. J Med Chem. Dec. 14, 2000;43(25):4919-22.
Merrifield et al., Solid Phase Peptide Syntheses. I. The Synthesis of a Tetrapeptide. J Am Chem Soc. 1963;85:2149-54.
Metzger et al., Ion-Spray Mass Spectrometry and High-Performance Liquid Chromatography-Mass Spectrometry of Synthetic Peptide Libraries. Angew Chem Int Ed Engl. 1993;32:894-96.
Miano et al., HDAC7 supports vascular integrity. Nat Med. Sep. 2006;12(9):997-8.
Miller et al., Histone deacetylase inhibitors. J Med Chem. Nov. 20, 2003;46(24):5097-116.
Miller et al., N-terminal methionine-specific peptidase in *Salmonella typhimurium*. Proc Natl Acad Sci U S A. May 1987;84(9):2718-22.
Minucci et al., Histone deacetylase inhibitors and the promise of epigenetic (and more) treatments for cancer. Nat Rev Cancer. Jan. 2006;6(1):38-51.
Miska et al., HDAC4 deacetylase associates with and represses the MEF2 transcription factor. Embo J. Sep. 15, 1999;18(18):5099-107.
Mitchison, Towards a pharmacological genetics. Chem Biol. Sep. 1994;1(1):3-6.
Mitsiades et al., Inhibition of the insulin-like growth factor receptor-1 tyrosine kinase activity as a therapeutic strategy for multiple myeloma, other hematologic malignancies, and solid tumors. Cancer Cell. Mar. 2004;5(3):221-30.
Mitsiades et al., Molecular sequelae of histone deacetylase inhibition in human malignant B cells. Blood. May 15, 2003;101(10):4055-62. Epub Jan. 16, 2003.
Mitsiades et al., Molecular sequelae of proteasome inhibition in human multiple myeloma cells. Proc Natl Acad Sci U S A. Oct. 29, 2002;99(22):14374-9. Epub Oct. 21, 2002.
Mitsiades et al., Novel biologically based therapies for Waldenstrom's macroglobulinemia. Semin Oncol. Apr. 2003;30(2):309-12.
Mitsiades et al., The proteasome inhibitor PS-341 potentiates sensitivity of multiple myeloma cells to conventional chemotherapeutic agents: therapeutic applications. Blood. Mar. 15, 2003;101(6):2377-80. Epub Nov. 7, 2002.
Mitsiades et al., Transcriptional signature of histone deacetylase inhibition in multiple myeloma: biological and clinical implications. Proc Natl Acad Sci U S A. Jan. 13, 2004;101(2):540-5. Epub Dec. 26, 2003.
Moazed, Enzymatic activities of Sir2 and chromatin silencing. Curr Opin Cell Biol. Apr. 2001;13(2):232-8.
Mori et al., Synthesis of trichostatin A, a potent differentiation inducer of friend leukemic cells, and its antipode. Tetrahedron. 1988;44:6013-20.
Mottet et al., Histone deacetylase 7 silencing alters endothelial cell migration, a key step in angiogenesis. Circ Res. Dec. 7, 2007;101(12):1237-46. Epub Oct. 18, 2007.
Mowat et al., Rearrangements of the cellular p53 gene in erythroleukaemic cells transformed by Friend virus. Nature. Apr. 18-24, 1985;314(6012):633-6.
Mullins et al., Transgenesis in nonmurine species. Hypertension. Oct. 1993;22(4):630-3.
Munshi et al., Acetylation of HMG I(Y) by CBP turns off IFN beta expression by disrupting the enhanceosome. Mol Cell. Oct. 1998;2(4):457-67.
Mutch et al., Effects of end groups on the stimulatory capacity of minimal length T cell determinant peptides. Pept Res. May-Jun. 1991;4(3):132-7.
Myers et al., Preparation of the Chiral, C-Protected α-Amino Aldehydes of High Optical Purity and Their Use as Condensation Components in a Linear Synthesis Strategy. J Am Chem Soc. 1999;121:8401-02.
Nagai et al., Synthesis of a Bicyclic Dipeptide with the Shape of β-Turn Central Part. Tetrahedron Lett. 1985;26:647-50.
Nagy et al., Nuclear receptor repression mediated by a complex containing SMRT, mSin3A, and histone deacetylase. Cell. May 2, 1997;89(3):373-80.
Nakatsuka et al., Total Synthesis of FK506 and an FKBP Probe Reagent, ($C_8$, $C_9$-$^{13}C_2$)-FK506. J. Am. Chem. Soc. 1990; 112: 5583-5601.
Nakazawa et al., UV and skin cancer: specific p53 gene mutation in normal skin as a biologically relevant exposure measurement. Proc Natl Acad Sci U S A. Jan. 4, 1994;91(1):360-4.
Narang, DNA Synthesis. Tetrahedron. 1983;39:3-22.
Nardelii et al., A chemically defined synthetic vaccine model for HIV-I. J Immunol. Feb. 1, 1992;148(3):914-20.
Nasmyth et al., Both positive and negative regulators of HO transcription are required for mother-cell-specific mating-type switching in yeast. Cell. Feb. 27, 1987;48(4):579-87.
Needleman et al., A general method applicable to the search for similarities in the amino acid sequence of two proteins. J Mol Biol. Mar. 1970;48(3):443-53.
Needles et al., Generation and screening of an oligonucleotide-encoded synthetic peptide library. Proc Natl Acad Sci. 1993;90:10700-04.
Neer et al., The ancient regulatory-protein family of WD-repeat proteins. Nature. Sep. 22, 1994;371(6495):297-300.
Nefzi et al., The Current Status of Heterocyclic Combinatorial Libraries. Chem Rev. Apr. 1, 1997;97(2):449-472.
Nestler et al., A General Method for Molecular Tagging of Encoded Combinatorial Chemistry Libraries. J Org Chem. 1994;59:4723-24.
Newman et al., The influence of natural products upon drug discovery. Nat Prod Rep. Jun. 2000;17(3):215-34.
Ng et al., Histone deacetylases: silencers for hire. Trends Biochem Sci. Mar. 2000;25(3):121-6.
Ngo et al., Computational complexity, protein structure prediction, and the ILeventhal paradox. In: The Protein Folding Problem and Tertiary Structure Prediction. Merz et al., eds, Birhauser, Boston, MA. 1994:433-506.
Nielsen et al., Crystal structure of a bacterial class 2 histone deacetylase homologue. J Mol Biol. Nov. 18, 2005;354(1):107-20. Epub Oct. 7, 2005.
Nielsen et al., Synthetic Methods for the Implementation of Encoded Combinatorial Chemistry. J Am Chem Soc. 1993;115:9812-13.
Nielsen et al., Toward Chemical Implementation of Encoded Combinatorial Libraries. Methods Compan Methods Enzymol. 1994;6:361-71.
Nikolaiev et al., Peptide-encoding for structure determination of nonsequenceable polymers within libraries synthesized and tested on solid-phase supports. Pept Res. May-Jun. 1993;6(3):161-70.
Noll, Characterization of macromolecules by constant velocity sedimentation. Nature. Jul. 22, 1967;215(5099):360-3.
Notterpek et al., PMP22 accumulation in aggresomes: implications for CMT1A pathology. Neurobiol Dis. Oct. 1999;6(5):450-60.
O'Connor, Developing new drugs for the treatment of lymphoma. European Journal of Haematology. 2005;75:150-58.
O'Gorman et al., Recombinase-mediated gene activation and site-specific integration in mammalian cells. Science. Mar. 15, 1991;251(4999):1351-5.
Ohlmeyer et al., Complex synthetic chemical libraries indexed with molecular tags. Proc Natl Acad Sci U S A. Dec. 1, 1993;90(23):10922-6.
Oliva et al., Histone hyperacetylation can induce unfolding of the nucleosome core particle. Nucleic Acids Res. May 11, 1990;18(9):2739-47.
Orban et al., Tissue- and site-specific DNA recombination in transgenic mice. Proc Natl Acad Sci U S A. Aug. 1, 1992;89(15):6861-5.
Park et al., Point mutations in the yeast histone H4 gene prevent silencing of the silent mating type locus HML. Mol Cell Biol. Sep. 1990;10(9):4932-4.
Parra et al., Protein kinase D1 phosphorylates HDAC7 and induces its nuclear export after T-cell receptor activation J Biol Chem. Apr. 8, 2005;280(14):13762-70. Epub Dec. 28, 2004.
Pátek et al., Safety-catch anchoring linkage for synthesis of peptide amides by Boc/Fmoc strategu. Tetrahedron Lett. 1991;32:3891-94.
Patel et al., Identification and characterization of small molecule inhibitors of a class I histone deacetylase from *Plasmodium falciparum*. J Med Chem. Apr. 23, 2009;52(8):2185-7.

Pei et al., Synergistic induction of oxidative injury and apoptosis in human multiple myeloma cells by the proteasome inhibitor bortezomib and histone deacetylase inhibitors. Clin Cancer Res. Jun. 1, 2004;10(11):3839-52.
Perrod et al., A cytosolic NAD-dependent deacetylase, Hst2p, can modulate nucleolar and telomeric silencing in yeast. EMBO J. Jan. 15, 2001;20(1-2):197-209.
Peterson et al., Small molecule developmental screens reveal the logic and timing of vertebrate development. Proc Natl Acad Sci U S A. Nov. 21, 2000;97(24):12965-9.
Phillips, The challenge of gene therapy and DNA delivery. J Pharm Pharmacol. Sep. 2001;53(9):1169-74.
Posnett et al., A novel method for producing anti-peptide antibodies. Production of site-specific antibodies to the T cell antigen receptor beta-chain. J Biol Chem. Feb. 5, 1988;263(4):1719-25.
Presbitero et al., Drug-eluting stents do they make the difference? Minerva Cardioangiol. Oct. 2002;50(5):431-42. Italian.
Probst et al., Human liver arylacetamide deacetylase. Molecular cloning of a novel esterase involved in the metabolic activation of arylamine carcinogens with high sequence similarity to hormone-sensitive lipase. J Biol Chem. Aug. 26, 1994;269(34):21650-6.
Pyne et al., Reactions of Lithiated *N*-Tosyl *S*-Phenyl *S*-2-Propenyl Sulfoximine with Aldehydes. Sulfur Letters. 1997;20(6):255-60.
Qian et al., A retinoblastoma-binding protein related to a negative regulator of Ras in yeast. Nature. Aug. 12, 1993;364(6438):648-52.
Raje et al., Combination of the mTOR inhibitor rapamycin and CC-5013 has synergistic activity in multiple myeloma. Blood. Dec. 15, 2004;104(13):4188-93. Epub Aug. 19, 2004.
Remiszewski, The discovery of NVP-LAQ824: from concept to clinic. Curr Med Chem. Nov. 2003;10(22):2393-402.
Renthal et al., Histone deacetylase 5 epigenetically controls behavioral adaptations to chronic emotional stimuli. Neuron. Nov. 8, 2007;56(3):517-29.
Richardson et al., A phase 2 study of bortezomib in relapsed, refractory myeloma. N Engl J Med. Jun. 26, 2003;348(26):2609-17.
Richon et al., A class of hybrid polar inducers of transformed cell differentiation inhibits histone deacetylases. Proc Natl Acad Sci U S A. Mar. 17, 1998;95(6):3003-7.
Richon et al., Histone deacetylase inhibitor selectively induces p21WAF1 expression and gene-associated histone acetylation. Proc Natl Acad Sci U S A. Aug. 29, 2000;97(18):10014-9.
Richon et al., Second generation hybrid polar compounds are potent inducers of transformed cell differentiation. Proc Natl Acad Sci U S A. Jun. 11, 1996;93(12):5705-8.
Riester et al., Members of the histone deacetylase superfamily differ in substrate specificity towards small synthetic substrates. Biochem Biophys Res Commun. Nov. 19, 2004;324(3):1116-23.
Rine et al., Four genes responsible for a position effect on expression from HML and HMR in *Saccharomyces cerevisiae*. Genetics. May 1987;116(1):9-22.
Rittinger et al., Structural analysis of 14-3-3 phosphopeptide complexes identifies a dual role for the nuclear export signal of 14-3-3 in ligand binding. Mol Cell. Aug. 1999;4(2):153-66.
Roberts et al., Directed evolution of a protein: selection of potent neutrophil elastase inhibitors displayed on M13 fusion phage. Proc Natl Acad Sci U S A. Mar. 15, 1992;89(6):2429-33.
Robertson et al., Germ-line transmission of genes introduced into cultured pluripotential cells by retroviral vector. Nature. Oct. 2-8, 1986;323(6087):445-8.
Rosato et al., Histone deacetylase inhibitors in clinical development. Expert Opin Investig Drugs. Jan. 2004;13(1):21-38.
Rudinger, Characteristics of the amino acids as components of a peptide hormone sequence. In: Peptide Hormones. J.A. Parsons, ed. University Park Press, Baltimore, MD. 1976;1-7.
Rundlett et al., HDA1 and RPD3 are members of distinct yeast histone deacetylase complexes that regulate silencing and transcription. Proc Natl Acad Sci U S A. Dec. 10, 1996;93(25):14503-8.
Ruygrok et al., Rapamycin in cardiovascular medicine. Intern Med J. Mar. 2003;33(3):103-9.
Saitou et al., The neighbor-joining method: a new method for reconstructing phylogenetic trees. Mol Biol Evol. Jul. 1987;4(4):406-25.
Sanchez Del Pino et al., Properties of the yeast nuclear histone deacetylase. Biochem J. Nov. 1, 1994;303 ( Pt 3):723-9.
Sasaki et al., Ligand-induced recruitment of a histone deacetylase in the negative-feedback regulation of the thyrotropin beta gene. Embo J. Oct. 1, 1999;18(19):5389-98.
Sato et al., Synthesis and Antibiotic Activity of a Gramicidin S Analogue containing Bicyclic β-Turn Dipeptides. J Chem Soc Perkin Trans. 1986;1:1231-34.
Sawa et al., Histone deacetylase inhibitors such as sodium butyrate and trichostatin A induce apoptosis through an increase of the bcl-2-related protein Bad. Brain Tumor Pathol. 2001;18(2):109-14.
Schena, Quantitative Monitoring of Gene Expression Patterns with a Complementary DNA Microarray. Science. 1995;270:467-70.
Schlienger et al., Human immunodeficiency virus type 1 major neutralizing determinant exposed on hepatitis B surface antigen particles is highly immunogenic in primates. J Virol. Apr. 1992;66(4):2570-6.
Schmidt et al., Rapid determination of methadone in plasma, cerebrospinal fluid, and urine by gas chromatography and its application to routine drug monitoring. Pharm Res. Mar. 1993;10(3):441-4.
Schreiber, Chemical genetics resulting from a passion for synthetic organic chemistry. Bioorg Med Chem. Aug. 1998;6(8):1127-52.
Schreiber, Target-oriented and diversity-oriented organic synthesis in drug discovery. Science. Mar. 17, 2000;287(5460):1964-9.
Schreiber, Using the Principles of Organic Chemistry to Explore Cell Biology. Chem and Eng News. 1992; 70(43): 22-32.
Schuetz et al., Human HDAC7 harbors a class IIa histone deacetylase-specific zinc binding motif and cryptic deacetylase activity. J Biol Chem. Apr. 25, 2008;283(17):11355-63. Epub Feb. 19, 2008.
Scott et al., Searching for peptide ligands with an epitope library. Science. Jul. 27, 1990;249(4967):386-90.
Secrist et al., HDAC inhibitors for the treatment of cancer. Curr Opin Investig Drugs. Dec. 2003;4(12):1422-7.
Seffernick et al., Melamine deaminase and atrazine chlorohydrolase: 98 percent identical but functionally different. J Bacteriol. Apr. 2001;183(8):2405-10.
Serrador et al., HDAC6 deacetylase activity links the tubulin cytoskeleton with immune synapse organization. Immunity. Apr. 2004;20(4):417-28.
Shpaer, GeneAssist. Smith-Waterman and other database similarity searches and identification of motifs. Methods Mol Biol. 1997;70:173-87.
Sikorski et al., A system of shuttle vectors and yeast host strains designed for efficient manipulation of DNA in *Saccharomyces cerevisiae*. Genetics. May. 1989;122(1):19-27.
Smith et al., A phylogenetically conserved NAD+-dependent protein deacetylase activity in the Sir2-protein family. Proc Natl Acad Sci U S A. Jun. 6, 2000;97(12):6658-63.
Smith et al., Comparison of biosequences. Adv Appl Math. 1981;2:482-89.
Smith et al., Mechanisms and molecular probes of sirtuins. Chem Biol. Oct. 20, 2008;15(10):1002-13.
Somoza et al., Structural snapshots of human HDAC8 provide insights into the class I histone deacetylases. Structure. Jul. 2004;12(7):1325-34.
Stamatakis et al., A rapid bootstrap algorithm for the RAxML Web servers. Syst Biol. Oct. 2008;57(5):758-71.
Sternson et al., Split—pool synthesis of 1,3-dioxanes leading to arrayed stock solutions of single compounds sufficient for multiple phenotypic and protein-binding assays. J. Am Chem Soc. Feb. 28, 2001;123(8):1740-7.
Sternson et al., Synthesis of 7200 small molecules based on a substructural analysis of the histone deacetylase inhibitors trichostatin and trapoxin. Org Lett. Dec. 27, 2001;3(26):4239-42.
Stevanovic et al., Natural and Synthetic Peptide Pools: Characterization by Sequencing and Electrospray Mass Spectrometry. Bioorg Med Chem Lett. 1993;3(3):431-36.
Stewart et al., Expression of retroviral vectors in transgenic mice obtained by embryo infection. Embo J. Feb. 1987;6(2):383-8.
Stillman et al., Epistasis analysis of suppressor mutations that allow HO expression in the absence of the yeast SW15 transcriptional activator. Genetics. Mar. 1994;136(3):781-8.

Strebhardt et al., Additional member of the protein-tyrosine kinase family: the src- and lck-related protooncogene c-tkl. Proc Natl Acad Sci U S A. Dec. 1987;84(24):8778-82.
Sullivan et al., Localization of the BiP molecular chaperone with respect to endoplasmic reticulum foci containing the cystic fibrosis transmembrane conductance regulator in yeast. J Histochem Cytochem. Apr. 2003;51(4):545-8.
Suzuki et al., Synthesis and histone deacetylase inhibitory activity of new benzamide derivatives. J Med Chem. Jul. 29, 1999;42(15):3001-3.
Tallarico et al., An alkylsilyl-tethered, high-capacity solid support amenable to diversity-oriented synthesis for one-bead, one-stock solution chemical genetics. J Comb Chem. May-Jun. 2001;3(3):312-8.
Tan et al., Stereoselective Synthesis of over Two Million Compounds Having Structural Features Both Reminiscent of Natural Products and Compatible with Miniaturized Cell-Based Assays. J. Am. Chem. Soc. 1998; 120: 8565-66.
Tanner et al., Silent information regulator 2 family of NAD-dependent histone/protein deacetylases generates a unique product, I-O-acetyl-ADP-ribose. Proc Natl Acad Sci U S A. Dec. 19, 2000;97(26):14178-82.
Tanny et al., Coupling of histone deacetylation to NAD breakdown by the yeast silencing protein Sir2: Evidence for acetyl transfer from substrate to an NAD breakdown product. Proc Natl Acad Sci U S A. Jan. 16, 2001;98(2):415-20. Epub Dec. 26, 2000.
Tao et al., Deacetylase inhibition promotes the generation and function of regulatory T cells. Nat Med. Nov. 2007;13(11):1299-307. Epub Oct. 7, 2007.
Taunton et al., A mammalian histone deacetylase related to the yeast transcriptional regulator Rpd3p. Science. Apr. 19, 1996;272(5260):408-11.
Taunton et al., Deacetylation. The Scientist. 1999;13:13.
Taunton et al., Synthesis of Natural and Modified Trapoxins, Useful Reagents for Exploring Histone Deacetylase Function. J Am Chem Soc. 1996;118:10412-22.
Thornton et al., Protein Engineering: Editorial Overview. Curr Opin Biotechnol. 1995;6(4):367-69.
Tissenbaum et al., Increased dosage of a sir-2 gene extends lifespan in Caenorhabditis elegans. Nature. Mar. 8, 2001;410(6825):227-30.
Tong et al., Chromatin deacetylation by an ATP-dependent nucleosome remodeling complex. Nature. 1997;395:917-21.
Tsang et al., CobB, a new member of the SIR2 family of eucaryotic regulatory proteins, is required to compensate for the lack of nicotinate mononucleotide:5,6-dimethylbenzimidazole phosphoribosyltransferase activity in cobT mutants during cobalamin biosynthesis in *Salmonella typhimurium* LT2. J Biol Chem. Nov. 27, 1998;273(48):31788-94.
Tsankova et al, Sustained hippocampal chromatin regulation in a mouse model of depression and antidepressant action. Nat Neurosci. Apr. 2006;9(4):519-25. Epub Feb. 26, 2006.
Turner, Decoding the nucleosome. Cell. Oct. 8, 1993;75(1):5-8.
Uchiyama et al., Adhesion of human myeloma-derived cell lines to bone marrow stromal cells stimulates interleukin-6 secretion. Blood. Dec. 15, 1993;82(12):3712-20.
Uong et al., Stereocontrolled Functionalization of Acyclic Molybdenum-$\eta^3$-Allyl Complexes: A New Approach to the Stereoselective Synthesis of 1,3-Diols. J Chem Soc Chem Commun. 1990:1285-87.
Urnov et al., Targeting of N-CoR and histone deacetylase 3 by the oncoprotein v-erbA yields a chromatin infrastructure-dependent transcriptional repression pathway. EMBO J. Aug. 1, 2000;19(15):4074-90.
Valerio et al., Multipin peptide synthesis at the micromole scale using 2-hydroxyethyl methacrylate grafted polyethylene supports. Int J Pept Protein Res. Jul. 1993;42(1):1-9.
Valerio et al., Synthesis of peptide analogues using the multipin peptide synthesis method. Anal Biochem. Aug. 15, 1991;197(1):168-77.
Van Der Krol et al., Modulation of eukaryotic gene expression by complementary RNA or DNA sequences. Biotechniques. Nov.-Dec. 1988;6(10):958-76.
Van Der Putten et al., Efficient insertion of genes into the mouse germ line via retroviral vectors. Proc Natl Acad Sci U S A. Sep. 1985;82(18):6148-52.
Vannini et al., Crystal structure of a eukaryotic zinc-dependent histone deacetylase, human HDAC8, complexed with a hydroxamic acid inhibitor. Proc Natl Acad Sci U S A. Oct. 19, 2004;101(42):15064-9. Epub Oct. 11, 2004.
Varga-Weisz et al., Chromatin-remodeling factors: machines that regulate? Curr Opin Cell Biol. Jun. 1998;10(3):346-53.
Vegas et al., Fluorous-based small-molecule microarrays for the discovery of histone deacetylase inhibitors. Angew Chem Int Ed Engl. 2007;46(42):7960-4.
Venter et al., The sequence of the human genome. Science. Feb. 16, 2001;291(5507):1304-51.
Verdel et al., Identification of a new family of higher eukaryotic histone deacetylases. Coordinate expression of differentiation-dependent chromatin modifiers. J Biol Chem. Jan. 22, 1999;274(4):2440-5.
Vidal et al., RPD3 encodes a second factor required to achieve maximum positive and negative transcriptional states in *Saccharomyces cerevisiae*. Mol Cell Biol. Dec. 1991;11(12):6317-27.
Vong et al., Regio-and Stereocontrolled Functionalization of Acyclic Molybdenum- $\eta^3$-Allyl Complexes. J Am Chem Soc. 1991;113:573-82.
Walker et al., Affinity chromatography of mammalian and yeast nucleosomes. Two modes of binding of transcriptionally active mammalian nucleosomes to organomercurial-agarose columns, and contrasting behavior of the active nucleosomes of yeast. J Biol Chem. Apr. 5, 1990;265(10):5736-46.
Wallace et al., Understanding cytochrome c function: engineering protein structure by semisynthesis. FASEB J. Apr. 1, 1993;7(6):505-15.
Wang et al., ETO, fusion partner in t(8;21) acute myeloid leukemia, represses transcription by interaction with the human N-CoR/mSin3/HDAC1 complex. Proc Natl Acad Sci U S A. Sep. 1, 1998;95(18):10860-5.
Wang et al., HDAC4, a human histone deacetylase related to yeast HDA1, is a transcriptional corepressor. Mol Cell Biol. Nov. 1999;19(11):7816-27.
Wang et al., Isolation of high-affinity peptide antagonists of 14-3-3 proteins by phage display. Biochemistry. Sep. 21, 1999;38(38):12499-504.
Wang et al., Zinc binding in HDAC inhibitors: a DFT study. J Org Chem. Jul. 6, 2007;72(14):5446-9. Epub Jun. 19, 2007.
Warrell et al., Therapeutic targeting of transcription in acute promyelocytic leukemia by use of an inhibitor of histone deacetylase. J Natl Cancer Inst. Nov. 4, 1998;90(21):1621-5.
Wegener et al., A fluorogenic histone deacetylase assay well suited for high-throughput activity screening. Chem Biol. Jan. 2003;10(1):61-8.
Weinberg, Finding the anti-oncogene. Sci Am. Sep. 1988;259(3):44-51.
Wennemers et al., Cyclooligomeric Receptors Based on Trimesic Acid and 1,2-Diamines. Minithal Structure for Sequence-Selective Peptide Binding. J Org Chem. 1995;60:1108-09.
Whelan et al., A general empirical model of protein evolution derived from multiple protein families using a maximum-likelihood approach. Mol Biol Evol. May 2001;18(5):691-9.
Wilen et al., Strategies in Optical Resolution. Tetrahedron. 1977;33:2725-36.
Witkowski et al., Conversion of a beta-ketoacyl synthase to a malonyl decarboxylase by replacement of the active-site cysteine with glutamine. Biochemistry. Sep. 7, 1999;38(36):11643-50.
Wong et al., Modular synthesis and preliminary biological evaluation of stereochemically diverse 1,3-dioxanes. Chem Biol. Sep. 2004;11(9):1279-91.
Wong et al., Structural biasing elements for in-cell histone deacetylase paralog selectivity. J Am Chem Soc. May 14, 2003;125(19):5586-7.
Workman et al., Alteration of nucleosome structure as a mechanism of transcriptional regulation. Annu Rev Biochem. 1998;67:545-79.

Xie et al., Sum1 and Hst1 repress middle sporulation-specific gene expression during mitosis in *Saccharomyces cerevisiae*. Embo J. Nov. 15, 1999;18(22):6448-54.
Xu et al., Coactivator and corepressor complexes in nuclear receptor function. Curr Opin Genet Dev. Apr. 1999;9(2):140-7.
Xue et al., NURD, a novel complex with both ATP-dependent chromatin-remodeling and histone deacetylase activities. Mol Cell. Dec. 1998;2(6):851-61.
Yaffe et al., The structural basis for 14-3-3:phosphopeptide binding specificity. Cell. Dec. 26, 1997;91(7):961-71.
Yang et al., Cloning and characterization of two mouse genes with homology to the yeast Sir2 gerie. Genomics. Nov. 1, 2000;69(3):355-69.
Yang et al., Isolation and characterization of cDNAs corresponding to an additional member of the human histone deacetylase gene family. J Biol Chem. Oct. 31, 1997;272(44):28001-7.
Yang et al., Maintenance of G2 arrest in the *Xenopus oocyte*: a role for 14-3-3-mediated inhibition of Cdc25 nuclear import. EMBO J. Apr. 15, 1999;18(8):2174-83.
Yang et al., Transcriptional repression by YY1 is mediated by interaction with a mammalian homolog of the yeast global regulator RPD3. Proc Natl Acad Sci U S A. Nov. 12, 1996;93(23):12845-50.
Yoon et al., Cyclooligomeric Receptors for the Sequence Selective Binding of Peptides. A Tetrahedral Receptor from the Trimesic Acid and 1,2-Diamines. Tetrahedron Lett. 1994;35:8557-60.
Yoshida et al., A novel tetracyclic peptide, trapoxin, induces phenotypic change from transformed to normal in sis-oncogene-transformed NIH3T3 cells. Jpn J Cancer Res. Apr. 1992;83(4):324-8.
Yoshida et al., Potent and specific inhibition of mammalian histone deacetylase both in vivo and in vitro by trichostatin A. J Biol Chem. Oct. 5, 1990;265(28):17174-9.
Yoshida et al., Trichostatin A and trapoxin: novel chemical probes for the role of histone acetylation in chromatin structure and function. Bioessays. May 1995;17(5):423-28.
Youngquist et al., Matrix-assisted laser desorption ionization for rapid determination of the sequences of biologically active peptides isolated from support-bound combinatorial peptide libraries. Rapid Commun Mass Spectrom. Jan. 1994;8(1):77-81.
Yu et al., The proteasome inhibitor bortezomib interacts synergistically with histone deacetylase inhibitors to induce apoptosis in Bcr/Abl+ cells sensitive and resistant to STI571. Blood. Nov. 15, 2003;102(10):3765-74. Epub Jul. 31, 2003.
Zervos et al., Mxil, a protein that specifically interacts with Max to bind Myc-Max recognition sites. Cell. Jan. 29, 1993;72(2):223-32.
Zhang et al., The dermatomyositis-specific autoantigen Mi2 is a component of a complex containing histone deacetylase and nucleosome remodeling activities. Cell. Oct. 16, 1998;95(2):279-89.
Zhou et al., Cloning and characterization of a histone deacetylase, HDAC9. Proc Natl Acad Sci U S A. Sep. 11, 2001;98(19):10572-7. Epub Sep. 4, 2001.
Zhou et al., Identification of a transcriptional repressor related to the noncatalytic domain of histone deacetylases 4 and 5. Proc Natl Acad Sci U S A. Feb. 1, 2000;97(3):1056-61.
Zimmermann et al., Conformational and epitope mapping of herpes-simplex-virus type-1 thymidine kinase using synthetic peptide segments. Eur J Biochem. Sep. 1, 2000;200(2):519-28.

Figure 1. Efficient Synthesis of an HDAC-Biased Library
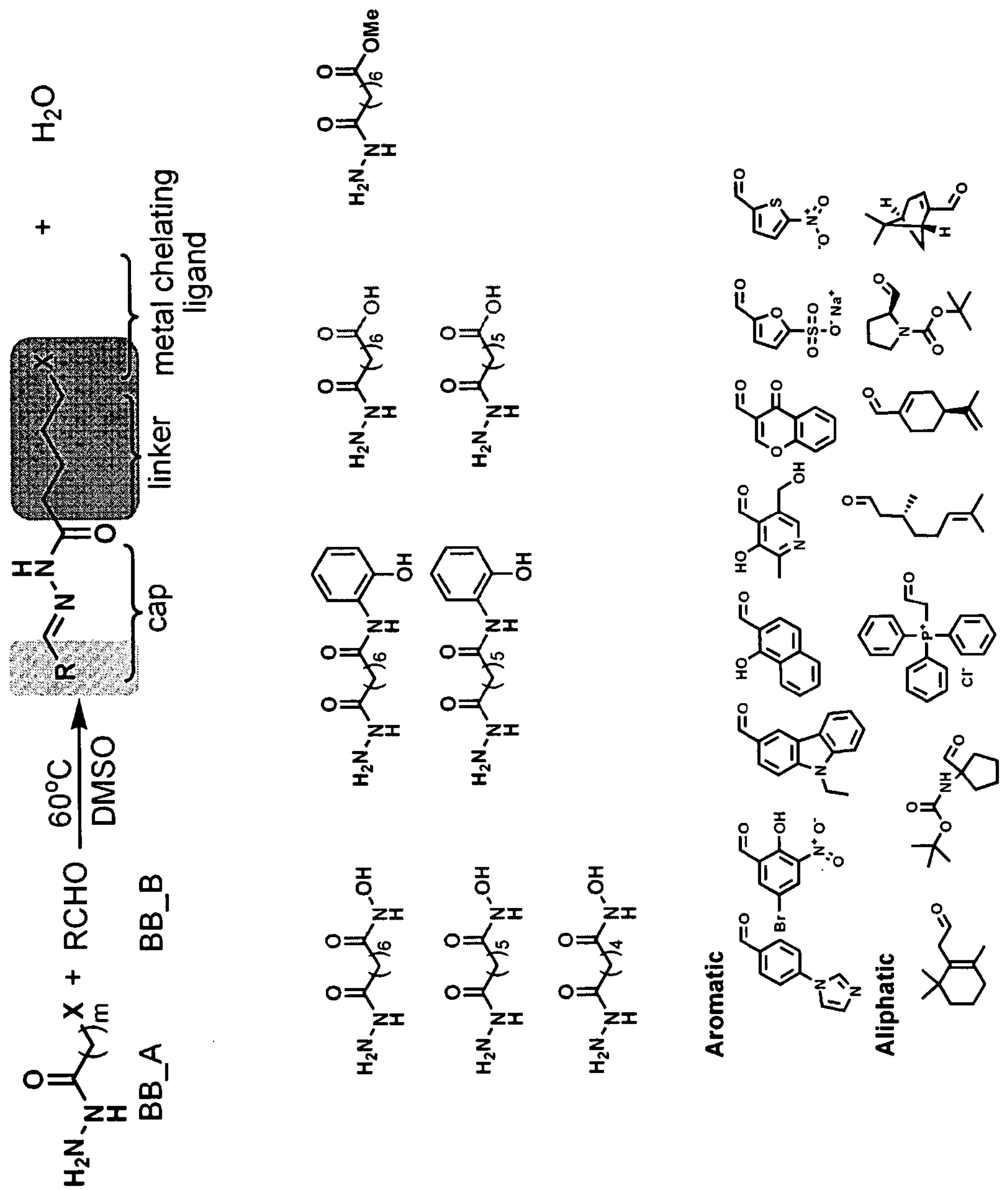
BB_A (8)
BB_B (~150)

Figure 2. High-Throughput, High-Content, Quantitative Detection Method
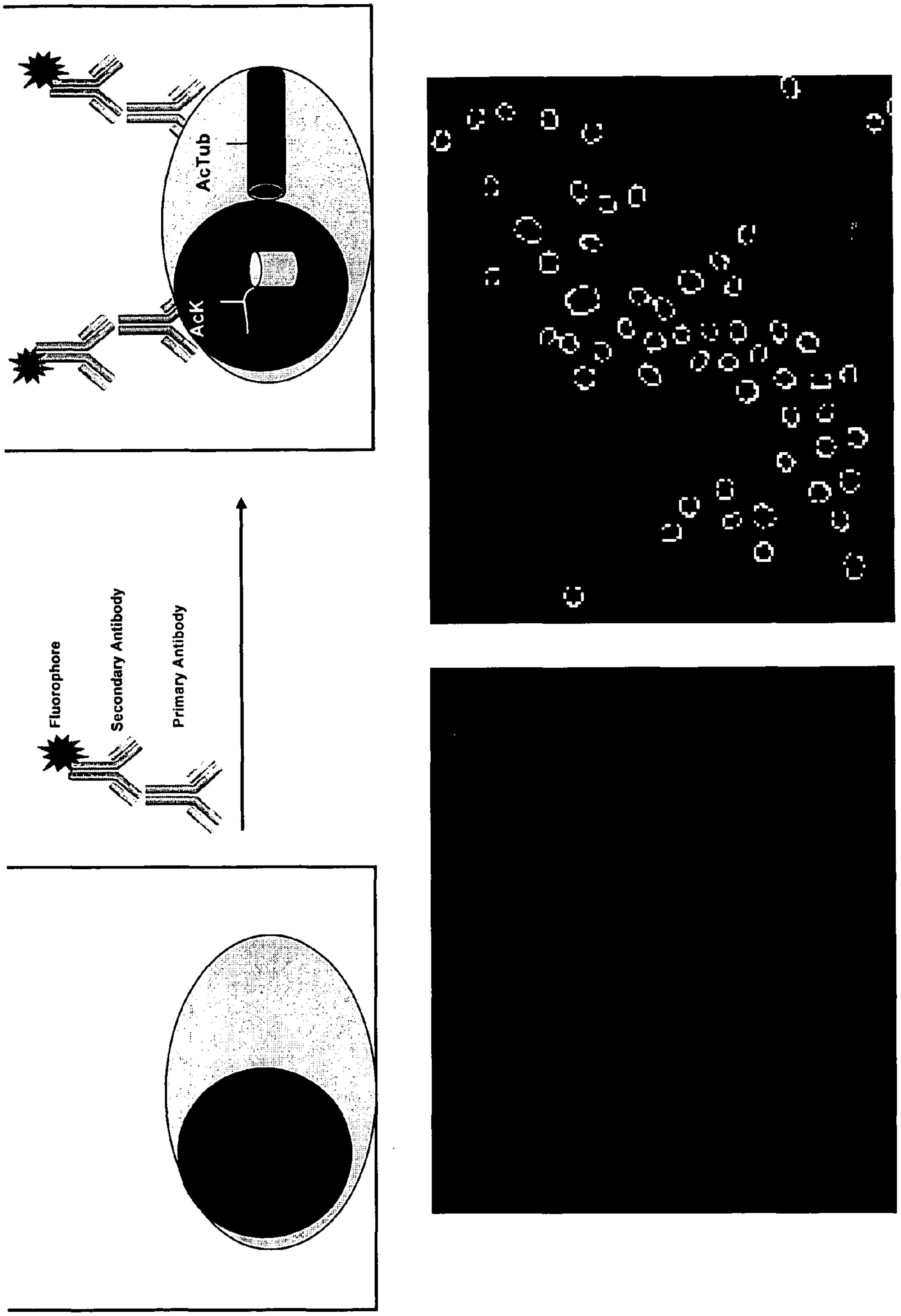

Figure 3. WT-III-161 Induction of AcTubulin (Red) and AcHistone (Blue) by HCS
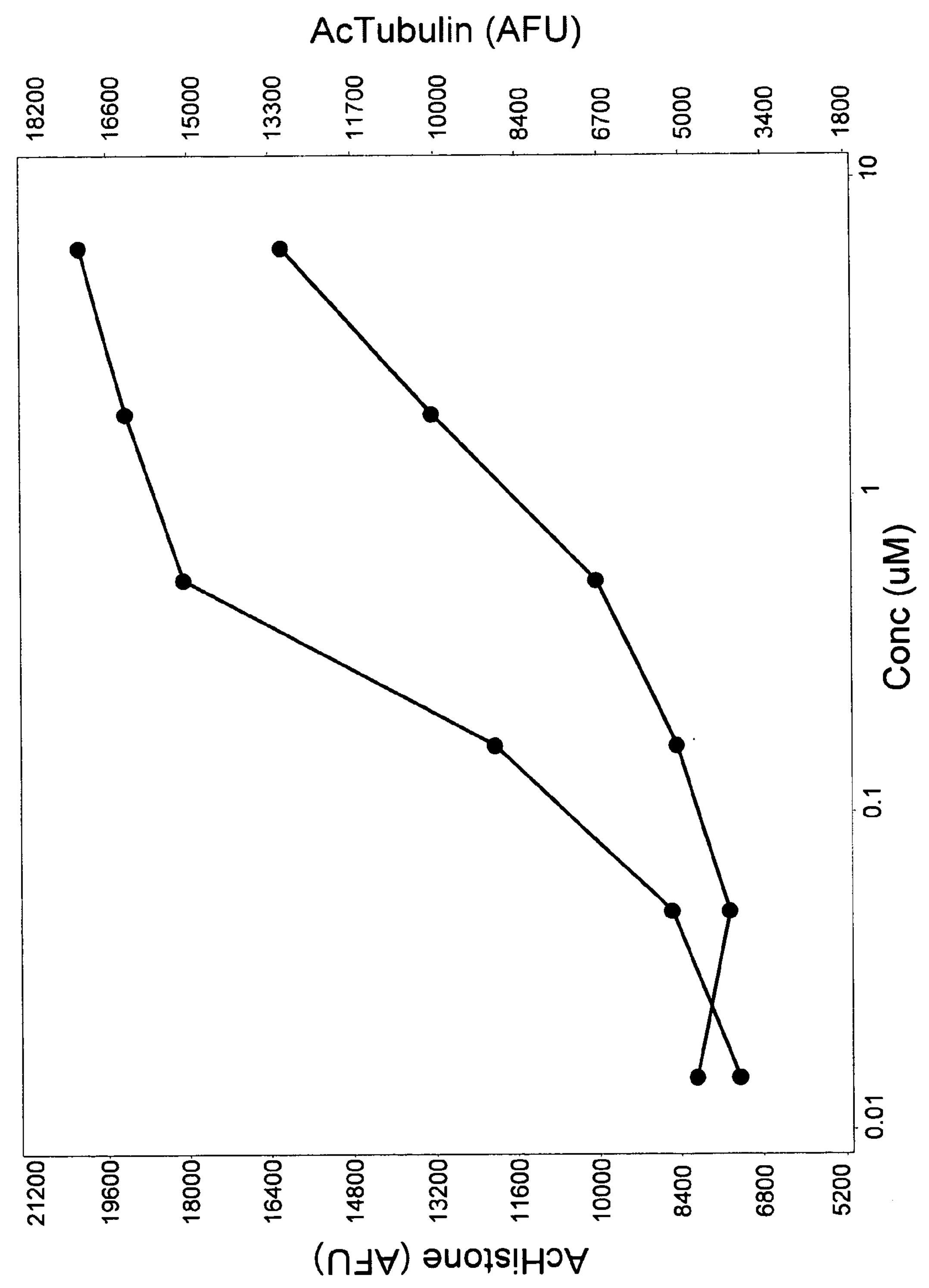

Figure 4. Selective Inhibition of HDAC6 by WT-III-161 in a Cellular Assay

| | TDAC EC-50 (uM) | HDAC EC-50 (uM) | TDAC Specificity |
|---|---|---|---|
| TSA | 0.036 | 0.02 | 0.56 |
| Tubacin | 0.87 | 8.7 | 10 |
| WT_III_161 | 0.35 | 4.3 | 12.3 |

Figure 5. HDAC Biochemical Assay Schema
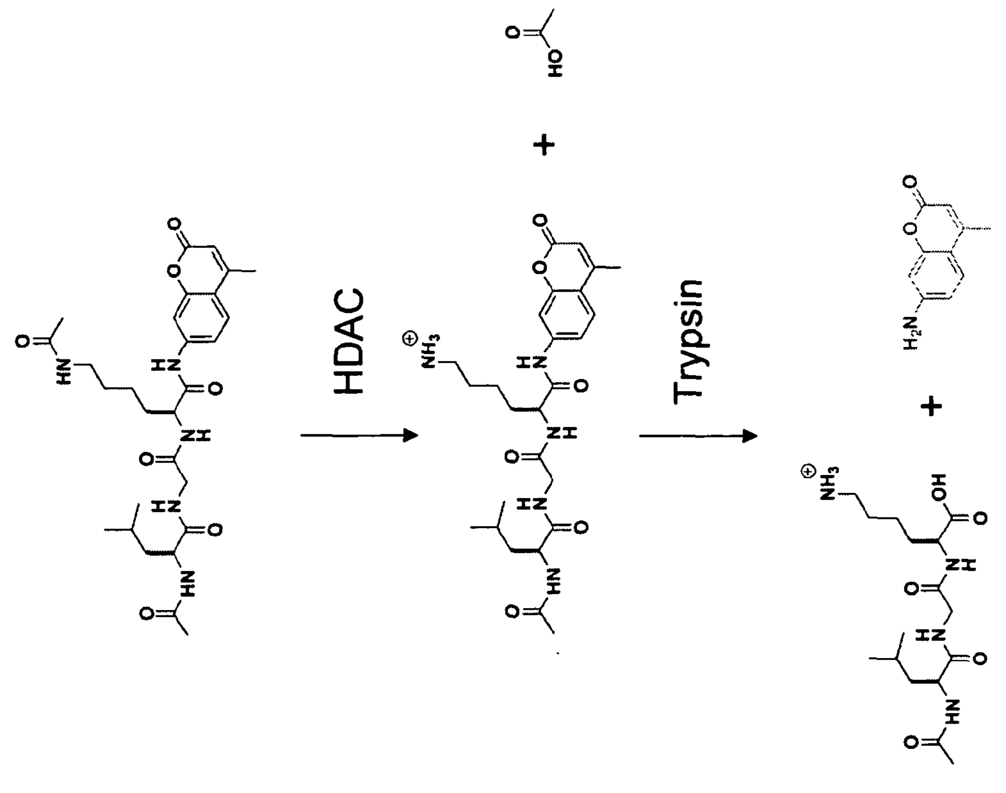
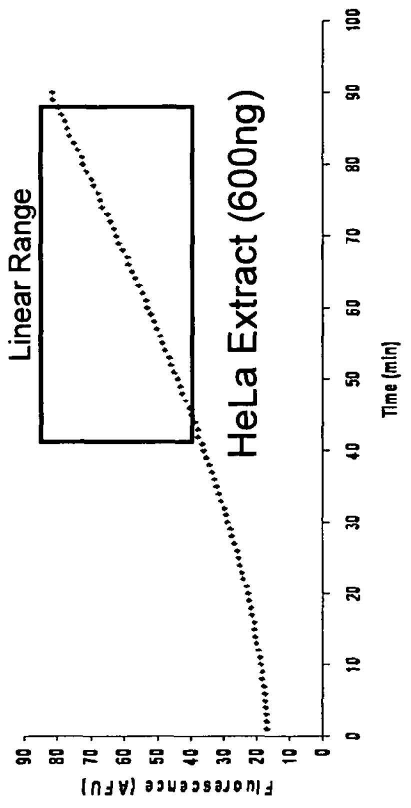

Figure 6. Selective Inhibition of HDAC6 by WT-III-161 in a Homogeneous Assay

| Compound | HDAC1 | HDAC2 | HDAC3 | HDAC6 | HDAC8 |
|---|---|---|---|---|---|
| APHA | 340 | 1030 | 480 | 100 | 3000 |
| Apicidin | | | | 10000 | 100 |
| CG-1521 | 560 | 520 | 880 | 200 | 1000 |
| CI-994 | 560 | 100 | 189 | 20000 | >>40000 |
| CRA-024781 | | 15 | | 25 | 2000 |
| HC-Toxin | | | | 4500 | 200 |
| ITF-2357 | | 10 | | 10 | 400 |
| MCG-D0103 | | 21 | 100 | >>40000 | >>40000 |
| MS-275 | 25 | 15 | 120 | >>40000 | >>40000 |
| Oxamflatin | | 21 | 13 | 50 | 1500 |
| PXD101 | | 21 | 10 | | 400 |
| Pyroxamide | 12 | 52 | 36 | 30 | 2000 |
| SAHA | 11 | 36 | 31 | 15 | 2000 |
| TSA | | | | | 700 |
| Tubacin | 240 | 260 | 610 | 20 | 8000 |
| **WT-III-161** | 240 | 150 | 390 | 45 | 5000 |

Figure 7. Superior Synergy for WT-III-161 and Bortezomib Compared to Other HDACi

| | MM1.S Vel-0 | MM1.S Vel-2.5 | MM1.S Vel-5 | RPMI Vel-0 | RPMI Vel-2.5 | RPMI Vel-5 |
|---|---|---|---|---|---|---|
| APHA | 18 | 11 | 12 | 8.5 | 7.4 | 1.9 |
| Apicidin | 0.47 | 0.32 | 0.17 | 0.63 | 0.51 | 0.086 |
| CI-994 | 6.6 | 8.1 | 4.1 | 1.9 | 2.4 | 0.77 |
| CRA-024781 | 0.48 | 0.48 | 0.20 | 0.60 | 0.44 | 0.14 |
| FK228 | 0.0030 | 0.0036 | 0.0026 | 0.0050 | 0.0040 | 0.0010 |
| HC-Toxin | 0.029 | 0.021 | 0.0098 | 0.014 | 0.016 | 0.0031 |
| ITF-2357 | 0.60 | 0.39 | 0.18 | 0.72 | 0.65 | 0.16 |
| MCG-D0103 | 1.5 | 1.2 | 0.79 | 0.47 | 0.50 | 0.16 |
| MS-275 | 1.9 | 1.3 | 0.61 | 0.20 | 0.23 | 0.092 |
| Pyroxamide | 6.4 | 6.1 | 2.3 | 6.2 | 5.0 | 0.85 |
| SAHA | 2.6 | 1.6 | 0.75 | 3.3 | 1.9 | 0.21 |
| Scriptaid | 1.8 | 1.3 | 0.54 | 1.8 | 1.1 | 0.21 |
| Trichostatin A | 0.047 | 0.037 | 0.031 | 0.051 | 0.046 | 0.0093 |
| Tubacin | 21 | 20 | | 14 | 12 | 1.7 |
| WT-III-161 | 7.5 | 5.1 | | 17 | 8.9 | |

Figure 8. Concentration-Time Curve of WT-III-161 in CD-1 Mice Following Intravenous Administration at 5 mg/kg
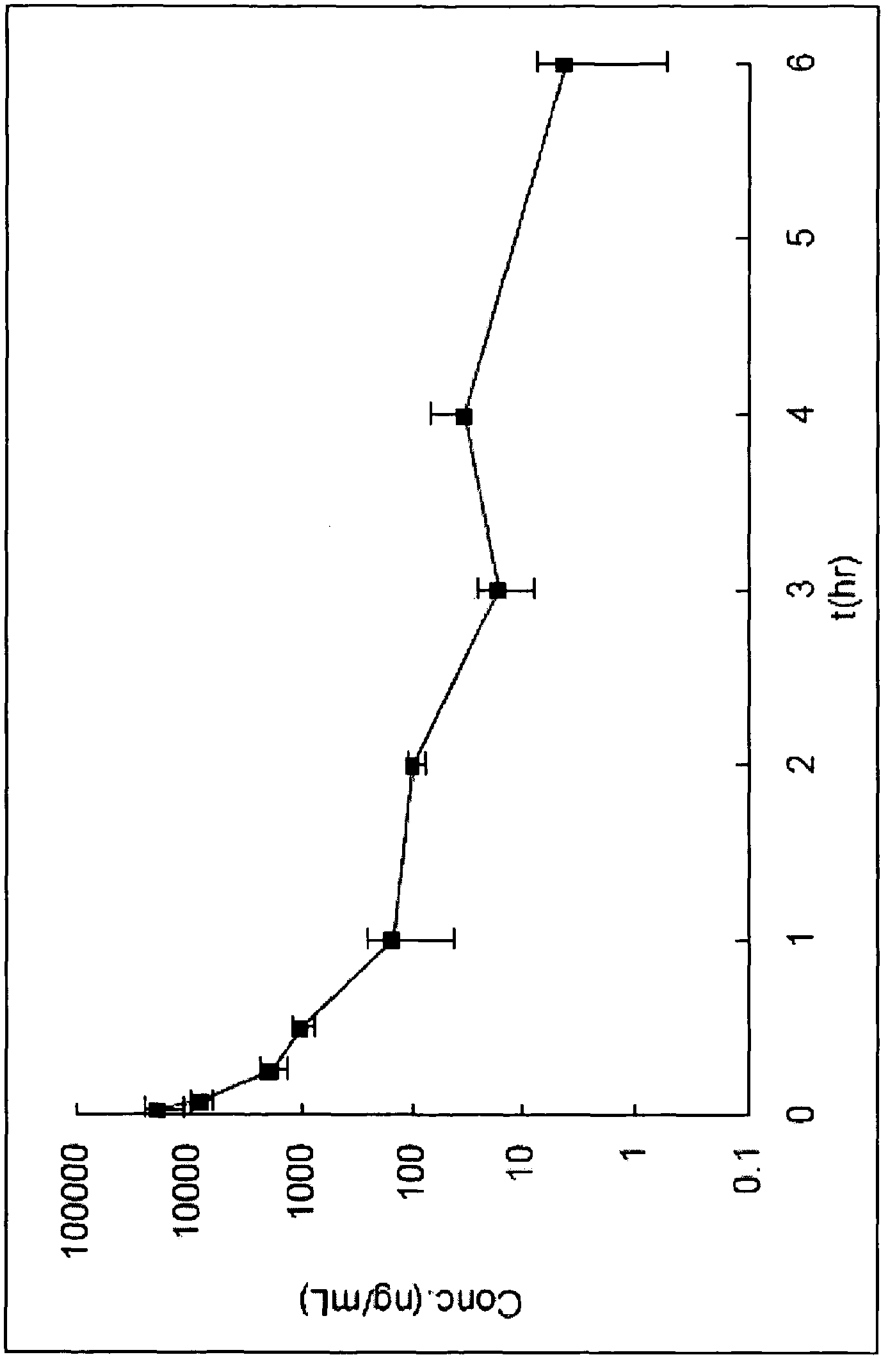

DEACETYLASE INHIBITORS AND USES THEREOF

RELATED APPLICATIONS

The present application is a national stage filing under 35 U.S.C. §371 of international PCT application, PCT/US2009/004235, filed Jul. 22, 2009, which claims priority under 35 U.S.C. §119(e) to U.S. provisional patent application, U.S. Ser. No. 61/082,899, filed Jul. 23, 2008, each of which is incorporated herein by reference.

BACKGROUND OF THE INVENTION

The identification of small organic molecules that affect specific biological functions is an endeavor that impacts both biology and medicine. Such molecules are useful as therapeutic agents and as probes of biological function. In but one example from the emerging field of chemical genetics, in which small molecules are used to alter the function of biological molecules to which they bind, these molecules have been useful at elucidating signal transduction pathways by acting as chemical protein knockouts, thereby causing a loss of protein function (Schreiber et al., *J. Am. Chem. Soc.,* 1990, 112, 5583; Mitchison, *Chem. and Biol.,* 1994, 1, 3). Additionally, due to the interaction of these small molecules with particular biological targets and their ability to affect specific biological function, they may also serve as candidates for the development of therapeutics.

One biological target of particular interest lately is histone deacetylase (see, for example, a discussion of the use of inhibitors of histone deacetylases for the treatment of cancer: Marks et al. *Nature Reviews Cancer* 2001, 1, 194; Johnstone et al. *Nature Reviews Drug Discovery* 2002, 1, 287; see also U.S. Pat. No. 7,250,504; U.S. Pat. No. 6,777,217; U.S. Published Application 2005/0287629; each of which is incorporated herein by reference). Post-translational modification of proteins through acetylation and deacetylation of lysine residues plays a critical role in regulating cellular functions. HDACs are zinc hydrolases that modulate gene expression through deacetylation of the N-acetyl-lysine residues of histone proteins and other transcriptional regulators (Hassig et al. *Curr. Opin. Chem. Biol.* 1997, 1, 300-308). HDACs participate in cellular pathways that control cell shape and differentiation, and at least one HDAC inhibitor has been shown effective in treating an otherwise recalcitrant cancer (Warrell et al. *J. Natl. Cancer Inst.* 1998, 90, 1621-1625). Eleven human HDACs, which use Zn as a cofactor, have been characterized (Taunton et al. *Science* 1996, 272, 408-411; Yang et al. *J. Biol. Chem.* 1997, 272, 28001-28007; Grozinger et al. *Proc. Natl. Acad. Sci. U.S.A.* 1999, 96, 4868-4873; Kao et al. *Genes Dev.* 2000, 14, 55-66; Hu et al. *J. Biol. Chem.* 2000, 275, 15254-15264; Zhou et al. *Proc. Natl. Acad. Sci. U.S.A.* 2001, 98, 10572-10577; Venter et al. *Science* 2001, 291, 1304-1351). These members fall into three related classes (class I, II and III). An additional seven HDACs have been identified which use NAD as a co-factor.

There remains a need for more potent and/or more specific deacetylase inhibitors (e.g., HDAC inhibitors) for treating diseases associated with aberrant deacetylase activity such as cancer.

SUMMARY OF THE INVENTION

The present invention provides novel deacetylase inhibitors and methods of preparing and using these novel compounds. In certain embodiments, the deacetylase inhibitors are histone deacetylase (HDAC) inhibitors. In certain embodiments, the deacetylase inhibitors are tubulin deacetylase (TDAC) inhibitors. The inventive compound may be useful in the treatment of proliferative diseases such as cancer.

For example, in one aspect, the present invention provides novel compounds of formula (I), (I)

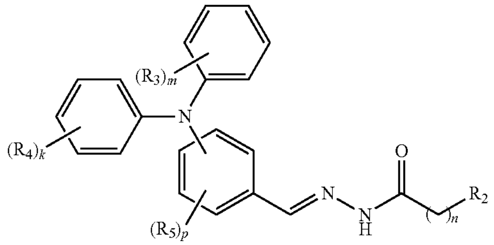

wherein $R_2$, $R_3$, $R_4$, $R_5$, m, n, k, and p are as defined herein. In certain embodiments, m, k, and p are 0. In certain embodiments, n is 3, 4, 5, 6, or 7. In certain embodiments, $R^2$ is a metal chelating moiety. In certain embodiments, $R^2$ is a $Zn^{2+}$ chelating group. In certain embodiments, $R^2$ is an acyl moiety. In certain embodiments, $R^2$ is selected from the group consisting of:

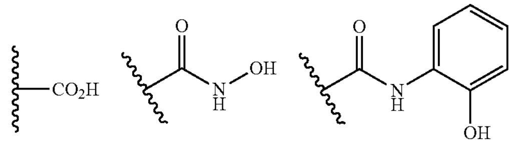

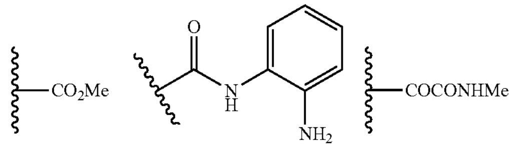

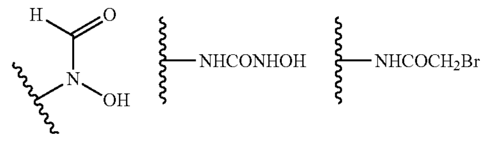

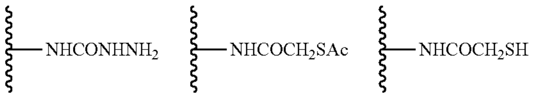

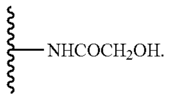

In certain embodiments, the compound is of the formula:

WT-161

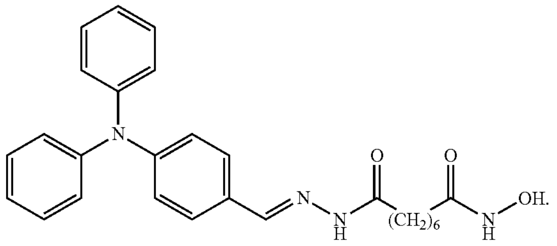

The invention also provides various pharmaceutically acceptable forms of the inventive compounds, for examples, stereoisomers, enantionmers, tautomers, salts, solvates, hydrates, co-crystals, and polymorphs.

In another aspect, the present invention provides pharmaceutical compositions comprising a therapeutically effective amount of a compound of formula (I) and a pharmaceutically acceptable excipient. In certain embodiments, the pharmaceutical composition is useful in the treatment of a proliferative disease such as cancer.

In yet another aspect, the present invention provides methods for inhibiting deacetylase activity in a subject or a biological sample, comprising administering to said subject, or contacting said biological sample, with an amount of a compound of the invention effective to inhibit deacetylase activity in the subject or biological sample. In certain embodiments, the method is used to specifically inhibit histone deacetylase activity in the subject or biological sample. In certain embodiments, the method is used to specifically inhibit a particular histone deacetylase activity in the subject or biological sample. In certain embodiments, the compounds specifically inhibit a particular HDAC (e.g., HDAC1, HDAC2, HDAC3, HDAC4, HDAC5, HDAC6, HDAC7, HDAC8, HDAC9, HDAC10, HDAC11) or class of HDACs (e.g., Class I, II and/or III). In certain embodiments, the inventive compound specifically inhibits HDAC6. In certain embodiments, the method is used to specifically inhibit tubulin deacetylase activity in a subject or a biological sample.

In certain embodiments, the present invention provides a method of treating a proliferative disease (e.g., cancer, benign neoplasm, autoimmune disease, inflammatory disease, diabetic retinopathy) comprising administering a therapeutically effective amount of a compound of formula (I) to a subject with a proliferative disease. In certain embodiments, the present invention provides a method of treating cancer (e.g., such as effecting tumor cell death or inhibiting the growth of tumor cells) by administering a therapeutically effective amount of a compound of formula (I) to a subject in need thereof. Exemplary cancer include, but are not limited to, breast cancer, cervical cancer, colon and rectal cancer, leukemia, lung cancer, melanoma, multiple myeloma, non-Hodgkin's lymphoma, lymphoma, ovarian cancer, pancreatic cancer, prostate cancer, skin cancer, and gastric cancer. In certain embodiments, the inventive compounds are active against leukemia cells and melanoma cells, and thus are useful for the treatment of leukemias (e.g., myeloid, lymphocytic, myelocytic and lymphoblastic leukemias) and malignant melanomas. In certain embodiments, the inventive compounds are useful in the treatment of cutaneous T-cell lymphoma (CTCL). The compounds may be administered by any method known in the art. In certain embodiments, the compounds are administered orally or parenterally (e.g., by intravenous, intrarterial, intramuscular, and/or subcutaneous injection).

The inventive compounds are also useful as tools to probe biological function. The compounds may be used to probe gene expression or to elucidate biological pathways. In certain embodiments, the compounds are used as probes of signal transduction pathways.

In still yet another aspect, the present invention provides methods for preparing compounds of the invention and intermediates thereof. Such methods comprise reacting an aldehyde-containing compound with a hydrazide-containing compound to provide a compound of formula (I).

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, $5^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, $3^{rd}$ Edition, Cambridge University Press, Cambridge, 1987; the entire contents of each of which are incorporated herein by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic, aliphatic and heteroaliphatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative diseases, including, but not limited to cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

Certain compounds of the present invention can comprise one or more asymmetric centers, and thus can exist in various isomeric forms, e.g., stereoisomers and/or diastereomers.

Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds.

Where a particular enantiomer is desired, it may, in some embodiments be provided substantially free of the corresponding enantiomer, and may also be referred to as "optically enriched." "Optically enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 96%, 97%, 98%, or 99% by weight of a desired enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972).

The term "acyl", as used herein, refers to a carbonyl-containing functionality, e.g., —C(═O)R', wherein R' is an aliphatic, alycyclic, heteroaliphatic, heterocyclic, aryl, heteroaryl, (aliphatic)aryl, (heteroaliphatic)aryl, heteroaliphatic (aryl) or heteroaliphatic(heteroaryl) moiety, whereby each of the aliphatic, heteroaliphatic, aryl, or heteroaryl moieties is substituted or unsubstituted, or is a substituted (e.g., hydrogen or aliphatic, heteroaliphatic, aryl, or heteroaryl moieties) oxygen or nitrogen containing functionality (e.g., forming a carboxylic acid, ester, or amide functionality).

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl, cyclohexyl, —$CH_2$-cyclohexyl, cyclohexenylethyl, cyclohexanylethyl, norbornyl moieties and the like, which again, may bear one or more substituents.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure $NH_2R'$—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN;

—$CF_3$; —$CH_2CF_3$; —$CHCl_2$; —$CH_2OH$; —$CH_2CH_2OH$; —$CH_2NH_2$; —$CH_2SO_2CH_3$; —C(O)$R_x$; —$CO_2(R_x)$; —CON$(R_x)_2$; —OC(O)$R_x$; —$OCO_2R_x$; —OCON$(R_x)_2$; —N$(R_x)_2$; —S(O)$_2R_x$; —N$R_x$(CO)$R_x$ wherein each occurrence of $R_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the term "aryl", as used herein, refers to a stable mono- or polycyclic, unsaturated moiety having preferably 3-14 carbon atoms, each of which may be substituted or unsubstituted. In certain embodiments, the term "aryl" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaryl", as used herein, refers to a stable mono- or polycyclic, unsaturated moiety having preferably 3-14 carbon atoms, each of which may be substituted or unsubstituted; and comprising at least one heteroatom selected from O, S, and N within the ring (i.e., in place of a ring carbon atom). In certain embodiments, the term "heteroaryl" refers to a planar ring comprising at least one heteroatom, having p-orbitals perpendicular to the plane of the ring at each ring atom, and satisfying the Huckel rule where the number of pi electrons in the ring is (4n+2) wherein n is an integer.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl) heteroaryl, and -(heteroalkyl)heteroaryl moieties. Thus, as used herein, the phrases "aryl or heteroaryl moieties" and "aryl, heteroaryl, -(alkyl)aryl, -(heteroalkyl) aryl, -(heteroalkyl) heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl", as used herein, does not differ significantly from the common meaning of the term in the art, and refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(O)$R_x$; —$CO_2(R_x)$; —CON$(R_x)_2$; —OC(O)$R_x$; —$OCO_2R_x$; —OCON$(R_x)_2$; —N$(R_x)_2$; —S(O)$R_x$; —S(O)$_2R_x$; —N$R_x$(CO)$R_x$ wherein each occurrence of $R_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(O)$R_x$; —$CO_2(R_x)$; —CON$(R_x)_2$; —OC(O)$R_x$; —$OCO_2R_x$; —OCON$(R_x)_2$; —N$(R_x)_2$; —S(O)$_2R_x$; —N$R_x$(CO)$R_x$ wherein each occurrence of $R_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(O)$R_x$; —$CO_2(R_x)$; —CON$(R_x)_2$; —OC(O)$R_x$; —$OCO_2R_x$; —OCON$(R_x)_2$; —N$(R_x)_2$; —$S(O)_2$ $R_x$; —$NR_x(CO)R_x$ wherein each occurrence of $R_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7-membered ring or a polycyclic group wherein at least one ring atom is a heteroatom selected from O, S, and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with, but are not limited to, aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(O)$R_x$; —$CO_2(R_x)$; —CON$(R_x)_2$; —OC(O)$R_x$; —$OCO_2R_x$; —OCON$(R_x)_2$; —N$(R_x)_2$; —$S(O)_2R_x$; —$NR_x(CO)R_x$ wherein each occurrence of $R_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substitutents described above and herein may be substituted or unsubstituted. Additional examples or generally applicable substituents are illustrated by the specific embodiments described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments described herein. The terms "halo" and "halogen" as used herein refer to an atom selected from fluorine, chlorine, bromine, and iodine.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—$NH_2$), secondary (—$NHR_x$), tertiary (—$NR_xR_y$), or quaternary (—$N^+R_xR_yR_z$) amine, where $R_x$, $R_y$ and $R_z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "alkylidene", as used herein, refers to a substituted or unsubstituted, linear or branched saturated divalent radical consisting solely of carbon and hydrogen atoms, having from one to n carbon atoms, having a free valence "—" at both ends of the radical. In certain embodiments, the alkylidene moiety has 1 to 6 carbon atoms.

The term "alkenylidene", as used herein, refers to a substituted or unsubstituted, linear or branched unsaturated divalent radical consisting solely of carbon and hydrogen atoms, having from two to n carbon atoms, having a free valence "—" at both ends of the radical, and wherein the unsaturation is present only as double bonds and wherein a double bond can exist between the first carbon of the chain and the rest of the molecule. In certain embodiments, the alkenylidene moiety has 2 to 6 carbon atoms.

The term "alkynylidene", as used herein, refers to a substituted or unsubstituted, linear or branched unsaturated divalent radical consisting solely of carbon and hydrogen atoms, having from two to n carbon atoms, having a free valence "—" at both ends of the radical, and wherein the unsaturation is present only as triple or double bonds and wherein a triple or double bond can exist between the first carbon of the chain and the rest of the molecule. In certain embodiments, the alkynylidene moiety has 2 to 6 carbon atoms.

Unless otherwise indicated, as used herein, the terms "alkyl", "alkenyl", "alkynyl", "heteroalkyl", "heteroalkenyl", "heteroalkynyl", "alkylidene", alkenylidene", -(alkyl) aryl, -(heteroalkyl) aryl, -(heteroalkyl)aryl, -(heteroalkyl) heteroaryl, and the like encompass substituted and unsubstituted, and linear and branched groups. Similarly, the terms "aliphatic", "heteroaliphatic", and the like encompass substituted and unsubstituted, saturated and unsaturated, and linear and branched groups. Similarly, the terms "cycloalkyl", "heterocycle", "heterocyclic", and the like encompass substituted and unsubstituted, and saturated and unsaturated groups. Additionally, the terms "cycloalkenyl", "cycloalkynyl", "heterocycloalkenyl", "heterocycloalkynyl", "aromatic", "heteroaromatic, "aryl", "heteroaryl" and the like encompass both substituted and unsubstituted groups.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Pharmaceutically acceptable derivatives also include "reverse pro-drugs." Reverse pro-drugs, rather than being activated, are inactivated upon absorption. For example, as discussed herein, many of the ester-containing compounds of the invention are biologically active but are inactivated upon exposure to certain physiological environments such as a blood, lymph, serum, extracellular fluid, etc. which contain esterase activity. The biological activity of reverse pro-drugs and pro-drugs may also be altered by appending a functionality onto the compound, which may be catalyzed by an enzyme. Also, included are oxidation and reduction reactions, including enzyme-catalyzed oxidation and reduction reactions. Certain exemplary pharmaceutical compositions and pharmaceutically acceptable derivatives will be discussed in more detail herein below.

By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable pro-drugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As used herein, the term "tautomer" includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

"Compound": The term "compound" or "chemical compound" as used herein can include organometallic compounds, organic compounds, metals, transitional metal complexes, and small molecules. In certain preferred embodiments, polynucleotides are excluded from the definition of compounds. In other preferred embodiments, polynucleotides and peptides are excluded from the definition of compounds. In a particularly preferred embodiment, the term compounds refers to small molecules (e.g., preferably, non-peptidic and non-oligomeric) and excludes peptides, polynucleotides, transition metal complexes, metals, and organometallic compounds.

"Small Molecule": As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 2000 g/mol, preferably less than 1500 g/mol, although this characterization is not intended to be limiting for the purposes of the present invention. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" *J. Am. Chem. Soc.* 120:8565, 1998; incorporated herein by reference). In certain other preferred embodiments, natural-product-like small molecules are utilized.

"Metal chelator": As used herein, the term "metal chelator" refers to any molecule or moiety that is is capable of forming a complex (i.e., "chelates") with a metal ion. In certain exemplary embodiments, a metal chelator refers to to any molecule or moiety that "binds" to a metal ion, in solution, making it unavailable for use in chemical/enzymatic reactions. In certain embodiments, the solution comprises aqueous environments under physiological conditions. Examples of metal ions include, but are not limited to, $Ca^{2+}$, $Fe^{3+}$, $Zn^{2+}$, $Na^{+}$, etc. In certain embodiments, the metal chelator binds $Zn^{2+}$. In certain embodiments, molecules of moieties that precipitate metal ions are not considered to be metal chelators.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human subject affected by a condition or disease to be diagnosed or investigated).

The biological sample can be in any form, including a solid material such as a tissue, cells, a cell pellet, a cell extract, cell homogenates, or cell fractions; or a biopsy, or a biological fluid. The biological fluid may be obtained from any site (e.g., blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis).

The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

BRIEF DESCRIPTION OF THE DRAWINGS

FIG. 1. Synthesis of an HDAC-biased library. The compounds of the library were prepared by conjugating an aldehyde-containing compound to a hydrazide-containing compound with a metal chelating moiety.

FIG. 2. High-throughput, high-content, quantitative detection method for identifying HDAC inhibitors. Cells are seeded in 384-well plates (2,000 cells/well) and treated with test compound, fixed, and then stained with Hoechst (nuclei), primary anti-AcTubulin monoclonal antibody and anti-AcHistone polyclonal antibody, then with compatible fluorophore-conjugated secondary antibodies. After automated image acquisition a custom analysis script identifies and masks cells, then derives quantitative fluorescence data from FITC (AcTubulin) and rhodamine (AcHistone) channels (MetaXPress; Molecular Devices).

FIG. 3. WT-161 Induction of AcTubulin (Red) and AcHistone (Blue) by HCS. As described in FIG. 2, the high content acetylation assay was employed to determine the comparative induction of acetylated histones versus acetylated tubulin across a dose-range of WT-161. These data support a selective inhibition of HDAC6 in cultured cells.

FIG. 4. Selective Inhibition of HDAC6 by WT-161 in a cellular assay. Dose-response data from FIG. 3 have been used to generate $EC_{50}$ values of cellular histone and tubulin acetylation effects of WT-161. These data are shown in comparison to experimental data acquired in parallel for control compounds, trichostatin and tubacin. HDAC activity is used to indicate biological activity of proteins mediating histone deacetylation, as this is a cellular assay measuring global effects on acetylation. TDAC activity is a surrogate measurement for HDAC6 inhibition in cultured cells.

FIG. 5. HDAC Biochemical Assay Schema. 7-amino-4-methylcoumarin (7AMC) is linked by an amide bond to acetylated lysine in the context of an isoform-selective substate. Pictured here is a derived substrate for HDACs 1, 2, 3, and 6. HDAC hydrolyzes acetylated lysine, which is then a substrate for rapid trypsin digestion releasing 7AMC (shown in green) which is detected in real time by a fluorescence plate reader. Linear data captured after a pre-incubation phase (30 minutes) provides a kinetic assessment of deacetylase activity.

FIG. 6. Selective Inhibition of HDAC6 by WT-161 in a homogeneous assay. Robust assay for HDACs 1, 2, 3, 5, 6, and 8 have been established. Inhibitory constants ($K_i$) for HDAC inhibitors are presented and color coded by potency (<10 nM=red; 11 nM-100 nM=yellow; 101-1000 nM=green; >1000 nM=blue). Inhibitory constants were determined by the equation $K_i=[I]/(((V_0/V_i)\times(1+[S]/K_m))-([S]/K_m)-1)$, where [I] is the concentration of inhibitor, [S] is the concentration of substrate, $V_0$ is the initial activity of enzyme without inhibitor, $V_i$ is the activity of enzyme with inhibitor, and Km is the Michaelis constant. Potent inhibition of HDAC6 by WT-161 is boxed.

FIG. 7. Superior Synergy for the combination of WT-161 and bortezomib compared to other HDAC inhibitors. Synergistic effects on cell proliferation were determined by varying concentrations of each HDAC inhibitor in the presence of varied concentrations of the proteasome inhibitor, bortezomib. Two cultures of human multiple myeloma cells were used for this study. Data presented are the $IC_{50}$ data for the HDAC inhibitor studied (first column) in the presence of increasing concentrations of bortezomib (0, 2.5 nM, or 5.0 nM). The measurement of cell proliferation used is the Cell TiterGlo assay (Promega),which uses bioluminescence to report on ATP content in cultured cells. Among all HDAC inhibitors studied, the most pronounced synergy was observed with WT-161 and the HDAC6 inhibitor, tubacin, both shown in red (dose reduction indices greatest).

FIG. 8. Concentration-Time Curve of WT-161 in CD-1 mice following intravenous administration at 5 mg/kg. WT-161 was injected into recipient mice by tail vein injection. Triplicate measurements of drug concentration in plasma was determined by LCMS.

DETAILED DESCRIPTION OF THE INVENTION

Figure 9:
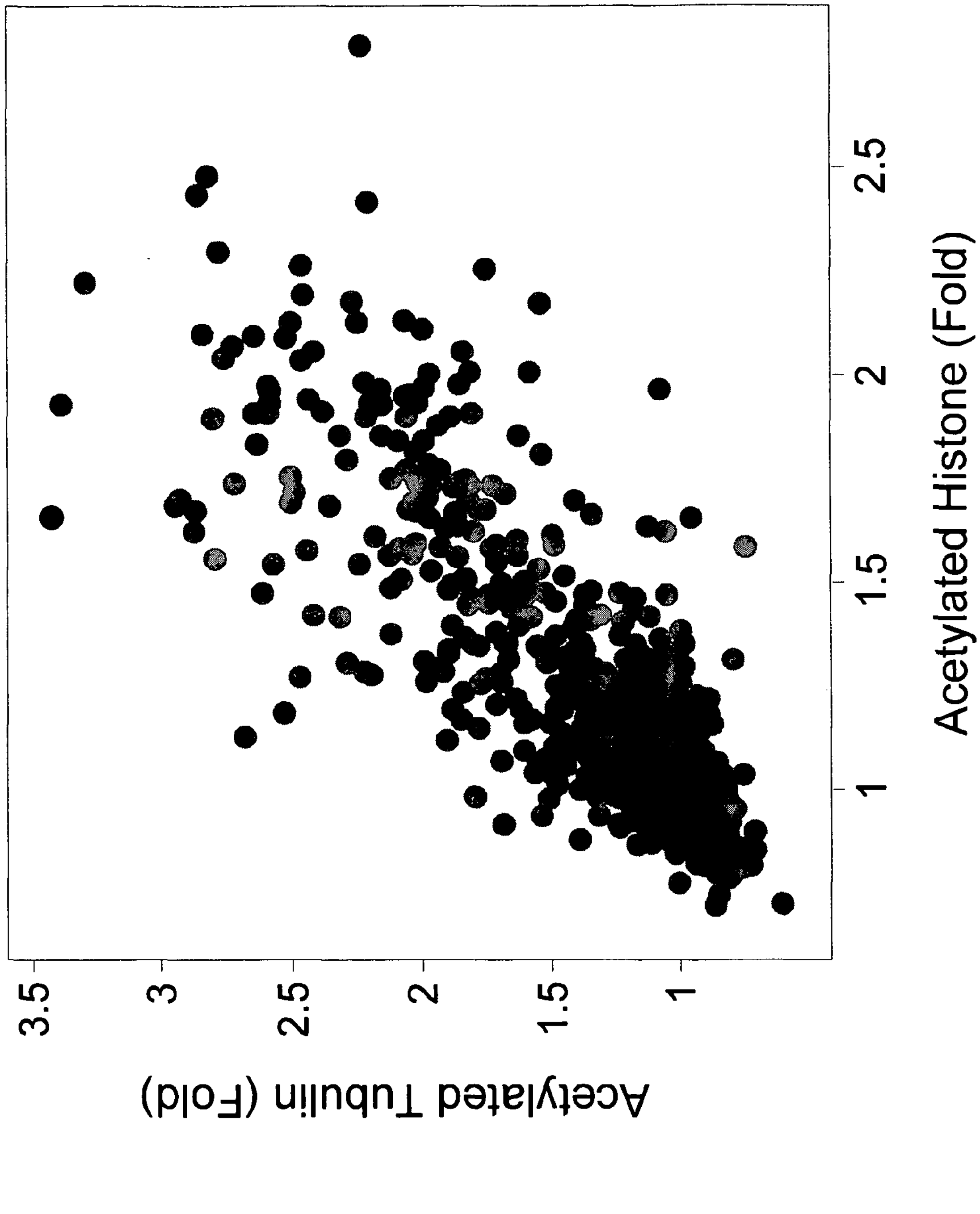
FIG. 9. Identification of WT-161 (shown in red) from primary screening data from large library of HDAC inhibitors based on acetylated tubulin and acetylated histone.

The present invention provides novel compounds of general formula (I) and pharmaceutical compositions thereof. The compounds generally include a metal chelating moiety connected to a cap through a linker. See FIG. 1. In certain embodiments, the deacetylase inhibitor is a histone deacetylase (HDAC) inhibitor. In certain particular embodiments, the deacetylase inhibitor is an HDAC6 inhibitor. In certain embodiments, the deacetylase inhibitor is a tubulin deacetylase (TDAC) inhibitor. The invention also provides methods for the synthesizing and using the inventive compounds. The compounds are useful as deacetylase inhibitors (e.g. HDAC inhibitors) and are useful in the treatment of proliferative diseases, such as cancer.

Compounds of the Invention

In general, the present invention provides compounds of the formula (I):

(I)

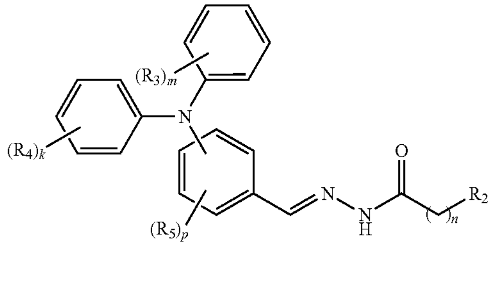

wherein n is an integer between 1 and 10, inclusive;

m is an integer between 0 and 5, inclusive;

k is an integer between 0 and 5, inclusive;

p is an integer between 0 and 5, inclusive;

$R^2$ is an optionally substituted acyl moiety $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —C(═O)$R_C$; —$CO_2R_C$; —CN; —SCN; —$SR_C$; —$SOR_C$; —$SO_2R_C$; —$NO_2$; —$N(R_C)_2$; —NHC(═O)$R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; —C(═O)$R_D$; —$CO_2R_D$; —CN; —SCN; —$SR_D$; —$SOR_D$; —$SO_2R_D$; —$NO_2$; —$N(R_D)_2$; —NHC(═O)$R_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_E$; —C(═O)$R_E$; —$CO_2R_E$; —CN; —SCN; —$SR_E$; —$SOR_E$; —$SO_2R_E$; —$NO_2$; —$N(R_E)_2$; —NHC(═O)$R_E$; or —$C(R_E)_3$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and pharmaceutically acceptable forms thereof.

In certain embodiments, n is an integer between 1 to 8, inclusive. In certain embodiments, n is an integer between 2 to 8, inclusive. In certain embodiments, n is an integer between 4 to 8, inclusive. In certain embodiments, n is an integer between 3 to 6, inclusive. In certain embodiments, n is an integer between 4 to 6, inclusive. In certain embodiments, n is 3. In certain embodiments, n is 4. In certain embodiments, n is 5. In certain embodiments, n is 6. In certain embodiments, n is 7. In certain embodiments, n is 8.

In certain embodiments, m is 0. In certain embodiments, m is 1. In certain embodiments, m is 2. In certain embodiments, m is 3. In certain embodiments, m is 4.

In certain embodiments, k is 0. In certain embodiments, k is 1. In certain embodiments, k is 2. In certain embodiments, k is 3. In certain embodiments, k is 4.

In certain embodiments, p is 0. In certain embodiments, p is 1. In certain embodiments, p is 2. In certain embodiments, p is 3. In certain embodiments, p is 4.

In certain embodiments, all of m, k, and p are 0. In certain embodiments, the sum of m, k, and p is 1. In certain embodiments, the sum of m, k, and p is 2. In certain embodiments, the sum of m, k, and p is 3. In certain embodiments, the sum of m, k, and p is 4. In certain embodiments, the sum of m, k, and p is 5.

In certain embodiments, $R_3$ is hydrogen. In certain embodiments, $R_3$ is halogen. In certain embodiments, $R_3$ is fluorine. In certain embodiments, $R_3$ is chlorine. In certain embodiments, $R_3$ is bromine. In certain embodiments, $R_3$ is iodine. In certain embodiments, cyclic or acyclic, substituted or unsubstituted, branched or unbranched aliphatic. In certain embodiments, $R_3$ is $C_1$-$C_6$alkyl. In certain embodiments, $R_3$ is methyl. In certain embodiments, $R_3$ is ethyl. In certain embodiments, $R_3$ is propyl. In certain embodiments, $R_3$ is butyl. In certain embodiments, $R_3$ is cyclic or acyclic, substituted or unsubstituted, branched or unbranched heteroaliphatic. In certain embodiments, $R_3$ is substituted or unsubstituted, branched or unbranched acyl. In certain embodiments, $R_3$ is substituted or unsubstituted, branched or unbranched aryl. In certain embodiments, $R_3$ is substituted or unsubstituted, branched or unbranched heteroaryl. In certain embodiments, $R_3$ is —$N(R_C)_2$. In certain embodiments, $R_3$ is —$N(R_C)_2$, wherein $R_C$ is hydrogen or $C_1$-$C_6$ alkyl. In certain embodiments, $R_3$ is —$NHR_C$. In certain embodiments, $R_3$ is —$NH_2$. In certain embodiments, $R_3$ is —$OR_C$, wherein $R_C$ is hydrogen or $C_1$-$C_6$ alkyl. In certain particular embodiments, $R_3$ is —OH. In certain particular embodiments, $R_3$ is —OMe. In certain embodiments, $R_3$ is —$SR_C$, wherein $R_C$ is hydrogen or $C_1$-$C_6$ alkyl. In certain particular embodiments, $R_3$ is —SH. In certain particular embodiments, $R_3$ is —SMe. In certain embodiments, $R_3$ is branched or unbranched acyl. In certain embodiments, $R_3$ is —C(═O)$R_C$. In certain embodiments, $R_3$ is —C(═O)$R_C$, wherein $R_C$ is hydrogen or $C_1$-$C_6$ alkyl. In certain embodiments, $R_3$ is —C(═O)$CH_3$. In certain embodiments, $R_3$ is —C(═O)$OR_C$. In certain embodiments, $R_3$ is —C(═O)$OR_C$, wherein $R_C$ is hydrogen or $C_1$-$C_6$ alkyl. In certain embodiments, $R_3$ is —C(═O)$N(R_C)_2$. In certain embodiments, $R_3$ is —C(═O)$NHR_C$. In certain embodiments, $R_3$ is —C(═O)$NH_2$. In certain embodiments, $R_3$ is —NHC(═O)$R_C$. In certain embodiments, $R_3$ is —NHC(═O)$R_C$, wherein $R_C$ is hydrogen or $C_1$-$C_6$alkyl. In certain embodiments, $R_3$ is —$SOR_C$. In certain embodiments, $R_3$ is —$SO_2R_C$. In certain embodiments, $R_3$ is —CN. In certain embodiments, $R_3$ is —SCN. In certain embodiments, $R_3$ is —$NO_2$.

In certain embodiments, $R_4$ is hydrogen. In certain embodiments, $R_4$ is halogen. In certain embodiments, $R_4$ is fluorine. In certain embodiments, $R_4$ is chlorine. In certain embodiments, $R_4$ is bromine. In certain embodiments, $R_4$ is iodine. In certain embodiments, cyclic or acyclic, substituted or unsubstituted, branched or unbranched aliphatic. In certain embodiments, $R_4$ is $C_1$-$C_6$alkyl. In certain embodiments, $R_4$ is methyl. In certain embodiments, $R_4$ is ethyl. In certain embodiments, $R_4$ is propyl. In certain embodiments, $R_4$ is butyl. In certain embodiments, $R_4$ is cyclic or acyclic, substituted or unsubstituted, branched or unbranched heteroaliphatic. In certain embodiments, $R_4$ is substituted or unsubstituted, branched or unbranched acyl. In certain embodiments, $R_4$ is substituted or unsubstituted, branched or unbranched aryl. In certain embodiments, $R_4$ is substituted or unsubstituted, branched or unbranched heteroaryl. In certain embodiments, $R_4$ is —$N(R_D)_2$. In certain embodiments, $R_4$ is —$N(R_D)_2$, wherein $R_D$ is hydrogen or $C_1$-$C_6$ alkyl. In certain embodiments, $R_4$ is —$NHR_D$. In certain embodiments, $R_4$ is —$NH_2$. In certain embodiments, $R_4$ is —$OR_D$, wherein $R_D$ is hydrogen or $C_1$-$C_6$ alkyl. In certain particular embodiments, $R_4$ is —OH. In certain particular embodiments, $R_4$ is —OMe. In certain embodiments, $R_4$ is —$SR_D$, wherein $R_D$ is hydrogen or $C_1$-$C_6$ alkyl. In certain particular embodiments, $R_4$ is —SH. In certain particular embodiments, $R_4$ is —SMe. In certain embodiments, $R_4$ is branched or unbranched acyl. In certain embodiments, $R_4$ is —C(═O)$R_D$. In certain embodiments, $R_4$ is —C(═O)$R_D$, wherein $R_D$ is hydrogen or $C_1$-$C_6$ alkyl. In certain embodiments, $R_4$ is —C(═O)$CH_3$. In certain embodiments, $R_4$ is —C(═O)$OR_D$. In certain embodiments, $R_4$ is —C(═O)$OR_D$, wherein $R_D$ is hydrogen or $C_1$-$C_6$ alkyl. In certain embodiments, $R_4$ is —C(═O)N$(R_D)_2$. In certain embodiments, $R_4$ is —C(═O)$NHR_D$. In certain embodiments, $R_4$ is —C(═O)$NH_2$. In certain embodiments, $R_4$ is —NHC(═O)$R_D$. In certain embodiments, $R_4$ is —NHC(═O)$R_D$, wherein $R_D$ is hydrogen or $C_1$-$C_6$alkyl. In certain embodiments, $R_4$ is —$SOR_D$. In certain embodiments, $R_4$ is —$SO_2R_D$. In certain embodiments, $R_4$ is —CN. In certain embodiments, $R_4$ is —SCN. In certain embodiments, $R_4$ is —$NO_2$.

In certain embodiments, $R_5$ is hydrogen. In certain embodiments, $R_5$ is halogen. In certain embodiments, $R_5$ is fluorine. In certain embodiments, $R_5$ is chlorine. In certain embodiments, $R_5$ is bromine. In certain embodiments, $R_5$ is iodine. In certain embodiments, cyclic or acyclic, substituted or unsubstituted, branched or unbranched aliphatic. In certain embodiments, $R_5$ is $C_1$-$C_6$alkyl. In certain embodiments, $R_5$ is methyl. In certain embodiments, $R_5$ is ethyl. In certain embodiments, $R_5$ is propyl. In certain embodiments, $R_5$ is butyl. In certain embodiments, $R_5$ is cyclic or acyclic, substituted or unsubstituted, branched or unbranched heteroaliphatic. In certain embodiments, $R_5$ is substituted or unsubstituted, branched or unbranched acyl. In certain embodiments, $R_5$ is substituted or unsubstituted, branched or unbranched aryl. In certain embodiments, $R_5$ is substituted or unsubstituted, branched or unbranched heteroaryl. In certain embodiments, $R_5$ is —N$(R_E)_2$. In certain embodiments, $R_5$ is —N$(R_E)_2$, wherein $R_E$ is hydrogen or $C_1$-$C_6$ alkyl. In certain embodiments, $R_5$ is —$NHR_E$. In certain embodiments, $R_5$ is —$NH_2$. In certain embodiments, $R_5$ is —$OR_E$, wherein $R_E$ is hydrogen or $C_1$-$C_6$ alkyl. In certain particular embodiments, $R_5$ is —OH. In certain particular embodiments, $R_5$ is —OMe. In certain embodiments, $R_5$ is —$SR_E$, wherein $R_E$ is hydrogen or $C_1$-$C_6$ alkyl. In certain particular embodiments, $R_5$ is —SH. In certain particular embodiments, $R_5$ is —SMe. In certain embodiments, $R_5$ is branched or unbranched acyl. In certain embodiments, $R_5$ is —C(═O)$R_E$. In certain embodiments, $R_5$ is —C(═O)$R_E$, wherein $R_E$ is hydrogen or $C_1$-$C_6$ alkyl. In certain embodiments, $R_5$ is —C(═O)$CH_3$. In certain embodiments, $R_5$ is —C(═O)$OR_E$. In certain embodiments, $R_5$ is —C(═O)$OR_E$, wherein $R_E$ is hydrogen or $C_1$-$C_6$ alkyl. In certain embodiments, $R_5$ is —C(═O)N$(R_E)_2$. In certain embodiments, $R_5$ is —C(═O)$NHR_E$. In certain embodiments, $R_5$ is —C(═O)$NH_2$. In certain embodiments, $R_5$ is —NHC(═O)$R_E$. In certain embodiments, $R_5$ is —NHC(═O)$R_E$, wherein $R_E$ is hydrogen or $C_1$-$C_6$alkyl. In certain embodiments, $R_5$ is —$SOR_E$. In certain embodiments, $R_5$ is —$SO_2R_E$. In certain embodiments, $R_5$ is —CN. In certain embodiments, $R_5$ is —SCN. In certain embodiments, $R_5$ is —$NO_2$.

As defined generally above, $R^2$ is an optionally substituted acyl moiety. In certain embodiments, $R^2$ is —C(═O)$R^A$, wherein $R^A$ is selected from —$OR^B$ or —N$(R^C)_2$, wherein $R^B$ is hydrogen or an optionally substituted alkyl moiety, and wherein $R^C$ is hydrogen, —OH, an optionally substituted aryl moiety, or an optionally substituted heteroaryl moiety.

In certain embodiments, $R^2$ is the group —C(═O)$R^A$, wherein $R^A$ is —$OR^B$, wherein $R^B$ is selected from hydrogen and optionally substituted alkyl moiety.

In certain embodiments, $R^2$ is —$CO_2H$.

In certain embodiments, $R^2$ is the group —C(═O)$OR^B$, wherein $R^B$ is an optionally substituted alkyl moiety. In certain embodiments, $R^2$ is —$CO_2CH_3$, —$CO_2CH_2CH_3$, —$CO_2CH_2CH_2CH_3$, or —$CO_2CH(CH_3)_2$. In certain embodiments, $R^2$ is —$CO_2CH_3$.

In certain embodiments, $R^2$ is the group —C(═O)$R^A$, wherein $R^A$ is —N$(R^C)_2$, and wherein $R^C$ is hydrogen, —OH, an optionally substituted aryl moiety, or optionally substituted heteroaryl moiety.

In certain embodiments, $R^2$ is the group —C(═O)$R^A$, wherein $R^A$ is —$NHR^C$, and wherein $R^C$ is —OH, an optionally substituted aryl moiety, or optionally substituted heteroaryl moiety.

In certain embodiments, $R^2$ is —C(═O)NHOH.

In certain embodiments, $R^2$ is the group —C(═O)$NHR^c$, wherein $R^c$ is an optionally substituted aryl or optionally substituted heteroaryl. In certain embodiments, $R^2$ is the group —C(═O)$NHR^c$, wherein $R^c$ an optionally substituted aryl moiety.

In certain embodiments, $R^2$ is the group —C(═O)$NHR^C$, wherein $R^C$ an aryl moiety of the structure:

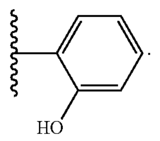 [SMILES: *c1ccccc1O]

In certain embodiments, $R^2$ comprises a metal chelating functional group. For example, $R^2$ comprises a $Zn^{2+}$ chelating group. In certain embodiments, $R^2$ is selected any one one of the following structures:

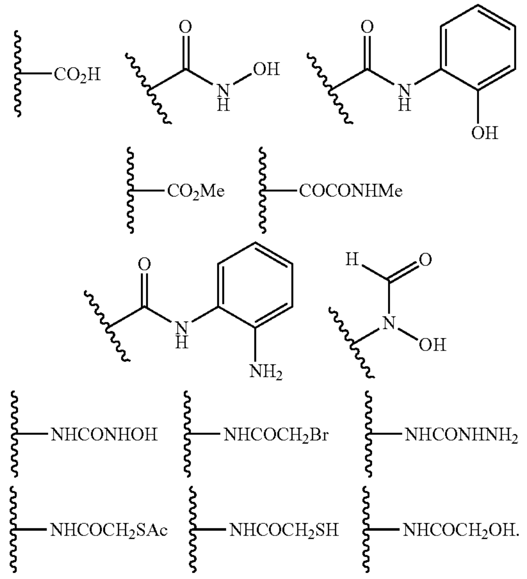

In certain embodiments, $R^2$ is of the formula:

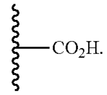

In certain embodiments, $R^2$ is of the formula:

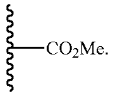

In certain embodiments, $R^2$ is of the formula:

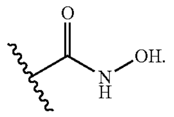 [SMILES: *C(=O)NO]

In certain embodiments, $R^2$ is of the formula:

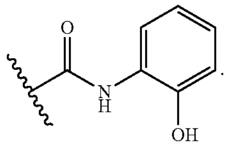 [SMILES: *C(=O)Nc1ccccc1O]

For example, in certain embodiments, a compound of formula (I) is selected from any one of the following compounds, wherein n is 4, 5, 6, or 7:

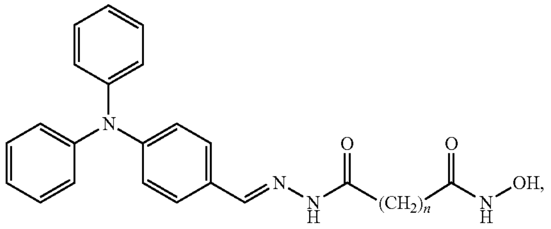

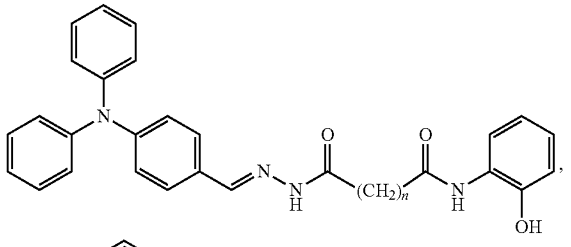

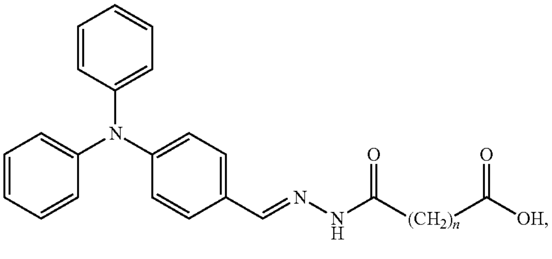

-continued

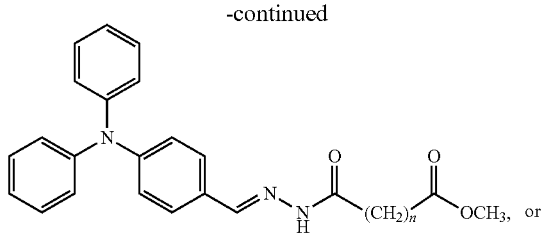

or a pharmaceutically acceptable form thereof. In certain embodiments, n is 4. In certain embodiments, n is 5. In certain embodiments, n is 6. In certain embodiments, n is 7.

In certain embodiments, the inventive compound is:

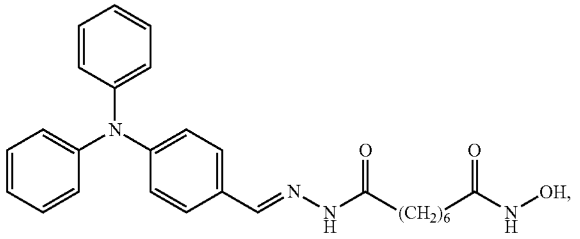

or a pharmaceutically acceptable form thereof.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer, or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of the compound under different conditions and may exist as one or a combination of polymorphs of the compound forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

Synthesis of Inventive Compounds

As would be appreciated by one of skill in the art of organic chemistry, the compounds of the invention may be prepared by any number of synthetic routes. In certain embodiments, a compound of formula (I) is prepared via condensation of a hydrazide compound of formula (II) and an aldehyde compound of formula (III) as shown in Scheme 1 below.

Scheme 1.

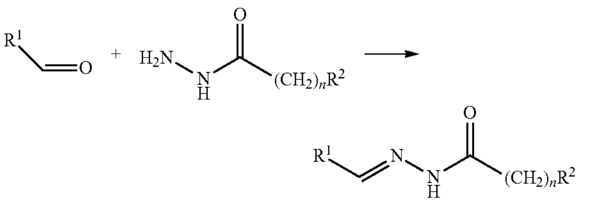

In certain embodiments, the present invention provides a method of preparing a compound of formula:

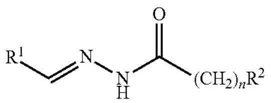

or a pharmaceutically acceptable form thereof;

wherein:

n is an integer between 1 and 10, inclusive;

$R^1$ is

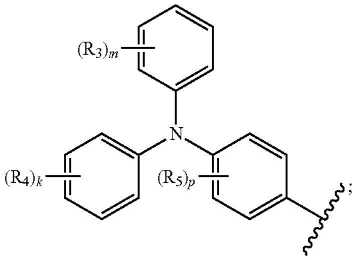

m is an integer between 0 and 5, inclusive;

k is an integer between 0 and 5, inclusive;

p is an integer between 0 and 5, inclusive;

$R^2$ is an optionally substituted acyl moiety $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —C(=O)$R_C$; —$CO_2R_C$; —CN; —SCN; —$SR_C$; —$SOR_C$; —$SO_2R_C$; —$NO_2$; —$N(R_C)_2$; —NHC(=O)$R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; —C(=O)$R_D$; —$CO_2R_D$; —CN; —SCN; —$SR_D$; —$SOR_D$; —$SO_2R_D$; —$NO_2$; —$N(R_D)_2$; —NHC(=O)$R_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and $R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_E$; —C(=O)$R_E$; —$CO_2R_E$; —CN; —SCN; —$SR_E$; —$SOR_E$; —$SO_2R_E$; —$NO_2$; —$N(R_E)_2$; —NHC(=O)$R_E$; or —$C(R_E)_3$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

comprising the steps of:

(i) providing a hydrazide of formula (II):

(II)

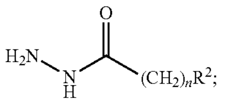

(ii) providing an aldehyde of formula (III):

(III)

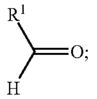

and (iii) reacting a hydrazide of formula (II) with an aldehyde of formula (III) under suitable conditions to provide a compound of formula:

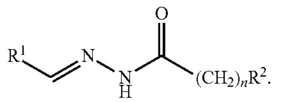

One of ordinary skill in the art will appreciate that a wide variety of reaction conditions may be employed to promote each of the synthetic transformations as depicted in Scheme I; therefore, a wide variety of reaction conditions are envisioned (see generally, *March's Advanced Organic Chemistry: Reactions, Mechanisms, and Structure*, M. B. Smith and J. March, 5th Edition, John Wiley & Sons, 2001; and *Comprehensive Organic Transformations*, R. C. Larock, 2nd Edition, John Wiley & Sons, 1999).

In certain embodiments, the reaction is performed in an organic solvent. In certain embodiments, the organic solvent is a polar aprotic solvent. In certain embodiments, the reaction is performed in dimethylsulfoxide (DMSO). In certain embodiments, the reaction is performed in dimethylformamide (DMF). In certain embodiments, the reaction is performed at a temperature between about 40° C. to about 80° C., or about 50° C. to about 70° C. In certain embodiments, the reaction is performed at a temperature of about 60° C. In certain embodiments, approximately 1 equivalent of each of the aldehyde and the hydrazide is used. In certain embodiments, approximately 1 equivalent of the aldehyde is used, and approximately 2-5 equivalents of the hydrazide is used in the reaction. In certain embodiments, approximately 1 equivalent of the hydrazide is used, and approximately 2-5 equivalents of the aldehyde is used in the reaction. In certain embodiments, approximately 1 equivalent of the more expensive starting material is used, and multiple equivalents of the less expensive starting are used.

In certain embodiments, the synthetic method is amenable to high-throughput techniques or to techniques commonly used in combinatorial chemistry. Therefore, in certain embodiments, a library of inventive compounds is prepared by using a variety of aldehydes and/or hydrazides in multiple reaction vessels. For example, FIG. 1 shows multiple starting materials that were used in the synthesis of a library of inventive compound.

Methods of Treatment

In general, the compounds of the invention are inhibitors of deacetylase activity. The compounds may inhibit histone deacetylase, tubulin deacetylase, or other deacetylase activity. In certain embodiments, the compounds of the invention are inhibitors of histone deacetylases (HDAC) and, as such, are useful in the treatment of disorders modulated by histone deacetylases. For example, in certain embodiments, the present invention provides a method for inhibiting deacetylase activity in a biological sample or a subject, which method comprises administering to the subject, or contacting the biological sample, an effective amount of an inventive compound or a composition thereof.

In certain embodiments, the deacetylase activity is histone deacetylase activity. In certain embodiments, the compounds specifically inhibit a particular histone deacetylase (HDAC) (e.g., HDAC1, HDAC2, HDAC3, HDAC4, HDAC4, HDAC5, HDAC6, HDAC7, HDAC8, HDAC9, HDAC10, HDAC11) or a class of HDACs (e.g., Class I, II and/or III). In certain embodiments, the compound specifically inhibits HDAC1. In certain embodiments, the compound specifically inhibits HDAC2. In certain embodiments, the compound specifically inhibits HDAC6.

In certain embodiments, the deacetylase activity is tubulin deacetylase activity. In certain embodiments, the compound of the invention is an inhibitor of a tubulin deacetylase (TDAC) and, as such, are useful in the treatment of a disorder or disease modulated by a tubulin deacetylase.

In another aspect, the present invention provides a method of treating a proliferative disease comprising administering a therapeutically effective amount of a compound of formula (I) to a subject in need thereof. In certain embodiments, the proliferative disease is associated with aberrant histone deacetylase activity and/or is controlled by modulating histone deacetylase activity. In certain embodiments, the proliferative disease is associated with aberrant tubulin deacetylase activity and/or is controlled by modulating tubulin deacetylase activity.

A subject may be any animal. In certain embodiments, the subject is any mammal (e.g., humans, domestic/veterinary/farm animals such as dogs, cats, cows, sheep, etc.). In certain embodiments, the subject is a human (e.g., child, juvenile, adult, male, female). In certain embodiments, the subject is an experimental animal such as a mouse, rat, dog, or non-human primate.

Exemplary proliferative diseases include, but are not limited to, cancer (e.g., glioblastoma, retinoblastoma, breast cancer, cervical cancer, colon and rectal cancer, leukemias, lymphoma, lung cancer (including, but not limited to small cell lung cancer and non-small cell lung cancer), melanoma and/or other skin cancers, multiple myeloma, non-Hodgkin's lymphoma, cutaneous T-cell lymphoma, and other lymphomas, ovarian cancer, pancreatic cancer, prostate cancer, gastric cancer, bladder cancer, uterine cancer, kidney cancer, testicular cancer, stomach cancer, brain cancer, liver cancer, and esophageal cancer), benign neoplasms, inflammatory disease, and autoimmune diseases.

In certain embodiments, the inventive compounds are also active against leukemia cells (e.g., leukemia cells and melanoma cells) and thus are useful for the treatment of leukemias (e.g., myeloid, lymphocytic, myelocytic and lymphoblastic leukemias). In certain embodiments, the inventive compounds are useful in the treatment of cutaneous T-cell lymphoma (CTCL) and skin cancers (e.g., squamous cell carcinoma, basal cell carcinoma, malignant melanoma, etc.). In certain embodiments, the inventive compounds are useful in the treatment of multiple myeloma. In certain embodiments, the inventive compounds are useful in the treatment of malignant melanoma.

For example, in certain embodiments, the present invention provides a method of treating cancer comprising administering a therapeutically effective amount of a compound of formula (I) to a subject in need thereof. In certain embodiments, the cancer is glioblastoma, retinoblastoma, breast cancer, cervical cancer, colon and rectal cancer, leukemia, lymphoma, lung cancer (including, but not limited to small cell lung cancer and non-small cell lung cancer), melanoma and/or other skin cancers, multiple myeloma, non-Hodgkin's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer.

The inventive compounds are also useful in the treatment of other diseases or condition that benefit from inhibition of deacetylation activity (e.g., HDAC or TDAC inhibition), such as certain skin and/or hair conditions (e.g., psoriasis, dermatitis, hair loss, neurofibromatosis, diseases associated with skin pigmentation).

In certain embodiments, the compounds are useful in treating inflammatory diseases of the skin such as psoriasis or dermatitis.

In certain embodiments, the compounds are useful in the treatment of neurofibromatosis.

A therapeutically effective amount of an inventive compound comprises administering an amounts and for such time as is necessary to achieve a desired result. The exact amount required will vary from subject to subject, depending on the species, age, and general condition of the subject, the severity of the disease, the particular anticancer agent, its mode of administration, the desired outcome, and the like.

In certain embodiments of the present invention a "therapeutically effective amount" of the inventive compound or pharmaceutical composition is that amount effective for inhibiting deacetylase activity (e.g., HDAC and/or TDAC activity) in a subject or a biological sample (e.g., in cells). In certain embodiments, a particular deacetylase activity (e.g., HDAC1, HDAC2, HDAC3, HDAC4, HDAC4, HDAC5, HDAC6, HDAC7, HDAC8, HDAC9, HDAC10, HDAC11) is inhibited by about 10%, about 20%, about 30%, about 40%, about 50%, about 60%, about 70%, about 80%, about 90%, about 95%, or about 99%. In certain embodiments, the inventive compound inhibits HDAC6, and a therapeutically effective amount of the compound inhibits HDAC6 by at least about 25%, at least about 50%, at least about 75%, or at least about 90%.

In certain embodiments of the present invention, a "therapeutically effective amount" refers to an amount of a compound or composition sufficient to inhibit cell proliferation, or refers to a sufficient amount to reduce the effects of the proliferative disease.

In certain embodiments of the present invention a "therapeutically effective amount" of the inventive compound or pharmaceutical composition is that amount effective for reducing or inhibiting the growth of tumor cells and/or killing tumor cells.

For example, in certain embodiments, the compounds are useful in the treatment of baldness based on the discovery that HDAC inhibition (particularly, HDAC6 inhibition) blocks androgen signaling via hsp90. HDAC inhibition has also been shown to inhibit estrogen signaling.

Additionally, in certain embodiments, the present invention provides methods of treating protozoal infections comprising administering a therapeutically effective amount of a compound of formula (I) to a subject in need thereof.

In certain embodiments, the inventive compounds also find use in the prevention of restenosis of blood vessels subject to traumas such as angioplasty and stenting. For example, it is contemplated that the compounds of the invention will be useful as a coating for implanted medical devices, such as tubings, shunts, catheters, artificial implants, pins, electrical implants such as pacemakers, and especially for arterial or venous stents, including balloon-expandable stents. In certain embodiments inventive compounds may be bound to an implantable medical device, or alternatively, may be passively adsorbed to the surface of the implantable device. In certain other embodiments, the inventive compounds may be formulated to be contained within, or, adapted to release by a surgical or medical device or implant, such as, for example, stents, sutures, indwelling catheters, prosthesis, and the like. For example, drugs having antiproliferative and anti-inflammatory activities have been evaluated as stent coatings, and have shown promise in preventing retenosis (See, for example, Presbitero P. et al., "Drug eluting stents do they make the difference?", *Minerva Cardioangiol,* 2002, 50(5): 431-442; Ruygrok P. N. et al., "Rapamycin in cardiovascular medicine", *Intern. Med. J.,* 2003, 33(3):103-109; and Marx S. O. et al., "Bench to bedside: the development of rapamycin and its application to stent restenosis", *Circulation,* 2001, 104(8):852-855, each of these references is incorporated herein by reference in its entirety).

Accordingly, without wishing to be bound to any particular theory, Applicant proposes that inventive compounds having antiproliferative effects can be used as stent coatings and/or in stent drug delivery devices, inter alia for the prevention of restenosis or reduction of restenosis rate. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, poly (lactic-co-glycolic acid), polyglycolic acid, ethylene vinyl acetate, and mixtures thereof. The coatings may optionally be further covered by a suitable topcoat of fluorosilicone, polysaccarides, polyethylene glycol, phospholipids, or combinations thereof to impart controlled release characteristics in the composition. A variety of compositions and methods related to stent coating and/or local stent drug delivery for preventing restenosis are known in the art (see, for example, U.S. Pat. Nos. 6,517,889; 6,273,913; 6,258,121; 6,251,136; 6,248,127; 6,231,600; 6,203,551; 6,153,252; 6,071,305; 5,891,507; 5,837,313; and published U.S. patent application US2001/0027340, each of which is incorporated herein by reference in its entirety). For example, stents may be coated with polymer-drug conjugates by dipping the stent in polymer-drug solution or spraying the stent with such a solution. In certain embodiment, suitable materials for the implantable device include biocompatible and nontoxic materials, and may be chosen from the metals such as nickel-titanium alloys, steel, or biocompatible polymers, hydrogels, polyurethanes, polyethylenes, ethylenevinyl acetate copolymers, etc. In certain embodiments, the inventive compound is coated onto a stent for insertion into an artery or vein following balloon angioplasty.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Within other aspects of the present invention, methods are provided for expanding the lumen of a body passageway, comprising inserting a stent into the passageway, the stent having a generally tubular structure, the surface of the structure being coated with (or otherwise adapted to release) an inventive compound or composition, such that the passageway is expanded. In certain embodiments, the lumen of a body passageway is expanded in order to eliminate a biliary, gastrointestinal, esophageal, tracheal/bronchial, urethral, and/or vascular obstruction.

Methods for eliminating biliary, gastrointestinal, esophageal, tracheal/bronchial, urethral and/or vascular obstructions using stents are known in the art. The skilled practitioner will know how to adapt these methods in practicing the present invention. For example, guidance can be found in U.S. Patent Application Publication 2003/0004209 in paragraphs [0146]-[0155], which paragraphs are hereby incorporated herein by reference.

Pharmaceutical Compositions

In another aspect, the present invention provides pharmaceutical compositions comprising a compound of formula (I), or a pharmaceutically acceptable form thereof, and a pharmaceutically acceptable excipient. In certain embodiments, a therapeutically effective amount of the inventive compound is included in the pharmaceutical composition.

It will also be appreciated that certain of the compounds of present invention can exist in free form for treatment, or where appropriate, as a pharmaceutically acceptable form thereof. According to the present invention, a pharmaceutically acceptable form includes, but is not limited to, pharmaceutically acceptable salts, esters, salts of such esters, or a prodrug or other adduct or derivative of a compound of this invention which upon administration to a subject in need is capable of providing, directly or indirectly, a compound as otherwise described herein, or a metabolite or residue thereof.

As described above, the pharmaceutical compositions of the present invention comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants, and the like, as suited to the particular dosage form desired. *Remington's Pharmaceutical Sciences*, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose, and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, *Remington's Pharmaceutical Sciences,* 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of therapeutic agent appropriate for the subject to be treated. It will be understood, however, that the total daily usage of the compounds and compositions of the present invention will be decided by the attending physician within the scope of sound medical judgment. The specific therapeutically effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts (see, for example, *Goodman and Gilman's The Pharmacological Basis of Therapeutics*, Tenth Edition, A. Gilman, J. Hardman and L. Limbird, eds., McGraw-Hill Press, 155-173, 2001, which is incorporated herein by reference in its entirety).

Furthermore, after formulation with an appropriate pharmaceutically acceptable excipient in a desired dosage, the pharmaceutical compositions of this invention can be administered to humans and other animals orally, rectally, parenterally, intracisternally, intravaginally, intraperitoneally, intravenously, intrarterially, intramuscularly, subcutaneously, topically (as by powders, ointments, creams or drops), bucally, as an oral or nasal spray, or the like, depending on the severity of the infection being treated. In certain embodiments, the inventive compounds is administered orally or intravenously.

In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another immunomodulatory agent, anticancer agent or agent useful for the treatment of psoriasis), or they may achieve different effects (e.g., control of any adverse effects).

For example, other therapies or anticancer agents that may be used in combination with the inventive compounds of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, *The Merck Manual*, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/druglistframe).

In certain embodiments, the pharmaceutical compositions of the present invention further comprise one or more additional therapeutic agents (e.g., chemotherapeutic and/or palliative). For example, additional therapeutic agents for conjoint administration or inclusion in a pharmaceutical composition with a compound of this invention may be an approved chemotherapeutic agent and/or pallative agent, or it may be any one of a number of agents undergoing approval in the Food and Drug Administration. For purposes of the invention, the term "palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

Kits

In certain embodiments, the present invention provides kits for conveniently and effectively carrying out the methods in accordance with the present invention. In general, the pack or kit comprises one or more containers filled with one or more of the ingredients of the pharmaceutical compositions of the invention. Optionally associated with such container(s) can be instructions for administration, including dosage recommendations, and/or a notice in the form prescribed by a governmental agency regulating the manufacture, use or sale of pharmaceutical products, wherein the notice reflects approval by the agency of manufacture, use or sale for human administration. A kit may include multiple dosage units. For example, a kit may include dosage units for multiple days, weeks, or months. In certain embodiments, the kit include a week-supply of the inventive compound or composition thereof. In certain embodiments, the kit include a month-supply of the inventive compound or composition thereof.

Research Uses and Assays

The inventive compounds are also useful as tools to probe biological function. For example, the inventive compounds may be used to probe biological pathways that depend on deacetylase (e.g., HDAC or TDAC) activity. In certain embodiments, the inventive compounds may be used to probe gene expression. In certain embodiments, the inventive compounds may be used to probe autophagy.

For example, according to the present invention, the inventive compounds may be assayed in any of the available assays known in the art for identifying compounds having antiprotozoal, HDAC inhibitory, hair growth, androgen signalling inhibitory, estogen signaling inhibitory, autophagy inhibitory, and/or antiproliferative activity. For example, the assay may be cellular or non-cellular, in vivo or in vitro, high- or low-throughput format, etc.

Thus, in one aspect, compounds of this invention which are of particular interest include those which: exhibit HDAC-inhibitory activity; exhibit HDAC Class I inhibitory activity (e.g., HDAC1, HDAC2, HDAC3, HDAC8); exhibit HDAC Class II inhibitory activity (e.g., HDAC4, HDAC5, HDAC6, HDAC7, HDAC9a, HDAC9b, HDRP/HDAC9c, HDAC10); exhibit HDAC Class III inhibitory activity; exhibit the ability to inhibit HDAC1 (Genbank Accession No. NP_004955, incorporated herein by reference); exhibit the ability to inhibit HDAC2 (Genbank Accession No. NP_001518, incorporated herein by reference); exhibit the ability to inhibit HDAC3 (Genbank Accession No. O15739, incorporated herein by reference); exhibit the ability to inhibit HDAC4 (Genbank Accession No. AAD29046, incorporated herein by reference); exhibit the ability to inhibit HDAC5 (Genbank Accession No. NP_005465, incorporated herein by reference); exhibit the ability to inhibit HDAC6 (Genbank Accession No. NP_006035, incorporated herein by reference); exhibit the ability to inhibit HDAC7 (Genbank Accession No. AAP63491, incorporated herein by reference); exhibit the ability to inhibit HDAC8 (Genbank Accession No. AAF73428, NM_018486, AF245664, AF230097, each of which is incorporated herein by reference); exhibit the ability to inhibit HDAC9 (Genbank Accession No. NM_178425, NM_178423, NM_058176, NM_014707, BC111735, NM_058177, each of which is incorporated herein by reference); exhibit the ability to inhibit HDAC10 (Genbank Accession No. NM_032019, incorporated herein by reference); exhibit the ability to inhibit HDAC11 (Genbank Accession No. BC009676, incorporated herein by reference); exhibit the ability to inhibit tubulin deacetylation (TDAC); exhibit the ability to modulate the glucose-sensitive subset of genes downstream of Ure2p; exhibit cytotoxic or growth inhibitory effect on cancer cell lines maintained in vitro or in animal studies using a scientifically acceptable cancer cell xenograft model; and/or exhibit a therapeutic profile (e.g., optimum safety and curative effect) that is superior to existing chemotherapeutic agents.

As detailed in the exemplification herein, in assays to determine the ability of compounds to inhibit cancer cell growth certain inventive compounds may exhibit $IC_{50}$ values $\leqq 100$ μM. In certain other embodiments, inventive compounds exhibit $IC_{50}$ values $\leqq 50$ μM. In certain other embodiments, inventive compounds exhibit $IC_{50}$ values $\leqq 40$ μM. In certain other embodiments, inventive compounds exhibit $IC_{50}$ values $\leqq 30$ μM. In certain other embodiments, inventive compounds exhibit $IC_{50}$ values $\leqq 20$ μM. In certain other embodiments, inventive compounds exhibit $IC_{50}$ values $\leqq 10$ μM. In certain other embodiments, inventive compounds exhibit $IC_{50}$ values $\leqq 7.5$ μM. In certain embodiments, inventive compounds exhibit $IC_{50}$ values $\leqq 5$ μM. In certain other embodiments, inventive compounds exhibit $IC_{50}$ values $\leqq 2.5$ μM. In certain embodiments, inventive compounds exhibit $IC_{50}$ values $\leqq 1$ μM. In certain embodiments, inventive compounds exhibit $IC_{50}$ values $\leqq 0.75$ μM. In certain embodiments, inventive compounds exhibit $IC_{50}$ values $\leqq 0.5$ μM. In certain embodiments, inventive compounds exhibit $IC_{50}$ values $\leqq 0.25$ μM. In certain embodiments, inventive compounds exhibit $IC_{50}$ values $\leqq 0.1$ μM. In certain other embodiments, inventive compounds exhibit $IC_{50}$ values $\leqq 75$ nM. In certain other embodiments, inventive compounds exhibit $IC_{50}$ values $\leqq 50$ nM. In certain other embodiments, inventive compounds exhibit $IC_{50}$ values $\leqq 25$ nM. In certain other embodiments, inventive compounds exhibit $IC_{50}$ values $\leqq 10$ nM. In other embodiments, exemplary compounds exhibited $IC_{50}$ values $\leqq 7.5$ nM. In other embodiments, exemplary compounds exhibited $IC_{50}$ values $\leqq 5$ nM.

EXAMPLES

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that, unless otherwise indicated, the entire contents of each of the references cited herein are incorporated herein by reference to help illustrate the state of the art. The following examples contain important additional information, exemplification and guidance which can be adapted to the practice of this invention in its various embodiments and the equivalents thereof.

Example 1

Synthesis of Exemplary Compounds for Use as HDAC Inhibitors

General Description of Synthetic Methods

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of a variety combinatorial techniques, parallel synthesis and/or solid phase synthetic methods such as those discussed in detail below may be used. Alternatively or additionally, the inventive compounds may be prepared using any of a variety of solution phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, *Reagents for Organic Synthesis*, vols. 1-17, John Wiley and Sons, New York, N.Y., 1991; Rodd 1989, *Chemistry of Carbon Compounds*, vols. 1-5 and supps, Elsevier Science Publishers, 1989; *Organic Reactions*, vols. 1-40, John Wiley and Sons, New York, N.Y., 1991; March 2001, *Advanced Organic Chemistry*, 5th ed. John Wiley and Sons, New York, N.Y.; and Larock 1990, *Comprehensive Organic Transformations: A Guide to Functional Group Preparations*, $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

Unless otherwise indicated, starting materials are either commercially available or readily accessibly through laboratory synthesis by anyone reasonably familiar with the art. Described generally below, are procedures and general guidance for the synthesis of compounds as described generally and in subclasses and species herein.

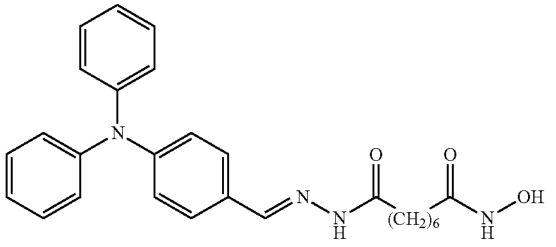

WT-161

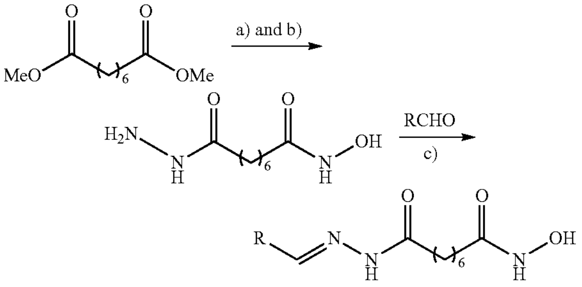

a) $NH_2NH_2$, MeOH, 60° C.;
b) $NH_2OH$/NaOH;
c) DMSO, 60° C.

Representative Procedure for the Synthesis of Biasing Agents

To a solution of dimethyl ester (300 mmol) in methanol (150 mL) was added hydrazine (4.5 mL, 150 mmol) at room temperature. The solution was stirred at 60° C. for 48 hours. The organic solvent was evaporated under vacuum. The resulting white solid was suspended in pet ether (100 mL). The solid was filtrated and washed with pet ether (3×200 mL) to remove excess starting materials. Flash chromatography on a short silica gel column eluting with 5% methanol in methylene chloride afforded the monomethyl ester monohydrazide as white solid.

To a solution of monomethyl ester monohydrazide (91.6 mmol) in methanol (100 mL) was added a solution of sodium hydroxide (14.65 g, 366.3 mmol) in methanol followed by a solution of hydroxylamine hydrochloride (12.73 g, 183.2 mmol) in methanol. The reaction was stirred at room temperature for 24 hours. Another batch of hydroxylamine hydrochloride (12.73 g, 183.2 mmol) in methanol was added to the reaction to quench the excess base. The suspension in methanol was heated to reflux before filtration. The solid was washed with 500 mL of hot ethanol. The combined liquid was evaporated under vacuum. The resulting solid was recrystallized in ethanol twice to afford pure products.

Representative Procedure for the Coupling of Acylhydrazide and Aldehydes

25 μL of aldehyde solution (0.2 M in DMSO) was added into 25 μL of hydrazide solution (0.2 M in DMSO). (25 mol % of HOAc is necessary when the aldehydes is basic.) The mixture was diluted with 450 μL DMSO after heating at 75° C. for 12 hours. The resulting solution (10 mM) was heated again at 75° C. for 12 hours. The purity of the acylhydrazone was analyzed by LCMS and predominantly one peak was observed for almost all compounds.

Example 2

Pharmacokinetics of WT-161

WT-III-161 (Wt: 458.55 for free base) was dissolved in 25% DMSO, 25% Cremophor EL, and 50% saline to yield final concentration at 2 mg/mL for intravenous administration (pH=6-7). The solution was clear and light yellow, and the concentration of WT-III-161 in it was confirmed by HPLC method with an accuracy of 116.92% (Table I).

TABLE I

| Experimental Design | | | | | |
|---|---|---|---|---|---|
| No. of Male Mice | Test Article Formulation | Dose Route | Target Dose Level* (mg/kg) | Target Dose Concentration* (mg/mL) | Target Dose Volume (mL/kg) |
| 36 | DMSO/Cremophor/ Saline | IV | 5 | 2 | 2.5 |

*The mice were fasted overnight for oral administration.

Study Design. Study design, animal selection, handling and treatment were in accordance with the Shanghai Medicilon Inc. study protocol (Shanghai Medicilon Inc Study No. BRD0701). Male CD0-1 mice (body weight 23 g to 27 g) were used in this study. Before the pharmacokinetic studies, animals were randomly assigned to the treatment groups (3 animals per timepoint). The treatment schedule is shown in Table 1. Ten additional mice were used to collect plasma for calibration curves.

Blood samples were collected by retro-orbital puncture at pre-dose and 0.033, 0.083, 0.25, 0.5, 1, 2, 3, 4, 6, 7, and 24 hours post-dose, and immediately after which the heart spleen, liver and brain tissues were harvested. All the samples and the dose formulation were stored at −20° C. until bioanalysis or transportation to sponsor.

The concentrations of WT-161 in plasma were determined using a high pressure liquid chromatography/mass spectrometry (LC-MS/MS) method.

LC-MS/NIS Apparatus. The LC system comprised an Aligent liquid chromatograph equipped with an isocratic pump (1100 series), an autosampler (1100 series) and a degasser (1100 series). Mass spectrometric analysis was performed using an API3000 (triple quadrupole) instrument from AB Inc (Canada) with an ESI interface. The data acquisition and control system were created using Analyst 1.4 software from ABI Inc. Acetonitrile and methanol were HPLC grade. All other solvents and chemicals were analytical grade or better.

Pharmacokinetic software DAS 2.0 (Gaosi Data Analysis Inc., Wuhn, China) was used.

LC-MS/NIS Conditions.

Chromatographic conditions: ColumnL Synergi Fusion-RP, 4 μm (150 mm×2.0 mm); Mobile phase: 0.1% formic acid:methanol:acetonitrile (5:90:5); Elution rate: 350 μL/min; Column temperature: 25° C.; Injection volume: 2 μL.

Mass Spectrometry Conditions.

Scan type: positive MRM; Ion Source: Turbo spray; Ionization mode: ESI; Nebulize gas: 8 L/min; Curtain gas: 8 L/min; Collision gas: 4 L/min; Ionspray voltage: 5000 V; Temperature: 500° C.

Other Parameters.

| Drug name | Q1 | Q3 | Dell time | DP (v) | FP (v) | EP (v) | CE (v) | CXP (v) |
|---|---|---|---|---|---|---|---|---|
| WT-161 | 459.2 | 271.2 | 200 ms | 80 | 200 | 10 | 36.3 | 15 |
| Quetiapine | 384.2 | 253.2 | 200 ms | 50 | 200 | 10 | 31.0 | 15 |

Preparation of standard stock solution: A stock solution of WT-161 was prepared by dissolving the drug in methanol to yield a final concentration of 200 μg/mL. An aliquot of this solution was diluted using methanol to prepare a series of working solutions of 5, 2.5, 0.5, 0.25, 0.05, and 0.025 μg/mL. Six calibration standard samples containing 1000, 500, 100, 50, 10, and 5 ng/mL were obtained by adding 20 μL working solution prepared above into six Eppendorff tubes containing 100 μL blank plasma. QC samples were prepared by spiking 100 uL blank plasma with 20 μL working solutions of 4, 1, and 0.04 μg/mL to yield final concentration of 800, 200 and 8 ng/mL (see Table II).

TABLE II

Preparation of Calibration Standard Solution and QC Samples

| Sample | Blank plasma (μL) | Amount (ng) of test article added (dissolved in 20 μL methanol)* | Working solution conc. (ng/mL) | Final volume of plasma (μL) | Final Conc. (ng · mL) in plasma* |
|---|---|---|---|---|---|
| Calibration solutions | | | | | |
| C-1 | 100 | 100 | 5,000 | 100 | 1,000 |
| C-2 | 100 | 50 | 2,500 | 100 | 500 |
| C-3 | 100 | 10 | 500 | 100 | 100 |
| C-4 | 100 | 5 | 250 | 100 | 50 |
| C-5 | 100 | 1 | 50 | 100 | 10 |
| C-6 | 100 | 0.5 | 25 | 100 | 5 |
| QC Samples | | | | | |
| QCH | 100 | 80 | 4,000 | 100 | 800 |
| QCM | 100 | 20 | 1,000 | 100 | 200 |
| QCL | 100 | 0.8 | 40 | 100 | 8 |
| Plasma samples from treated mice | | | | | |
| From mouse | 100 | 20 μL methanol* | | 100 | To be determined from calibration curve |

*20 μL, was counted as extraction solvent, not as plasma.

Note:

The QC samples were prepared in duplicate.

Stock solutions of Quetiapine (internal standard, IS) were prepared by dissolving the drug in methanol to a final concentration of 200 μg/mL. This solution was diluted with methanol to yield a final concentration of 50 ng/mL.

Plasma Sample Process. Plasma samples (0.1 mL) were transferred to Eppendorff tubes, then 20 μL of methanol, 500 μL IS solutions (50 ng/mL) were added to it. After vortexing for 1 minute and centrifuging for 5 min at 15,000 rpm, 2 μL of supernatant was injected onto the LC-MS/MS.

Method Validation Results. The chromatographic conditions showed that the blank plasma had no interference to the WT-161 and IS determination.

Calibration Curve. The analytical curves were constructed using six nonzero standards ranging from 5 to 1000 ng/mL. A blank sample (matrix sample processed without internal standard) was used to exclude contamination. The linear regression analysis of WT-161 was performed by plotting the peak area ratio (y) against the WT-161 concentration (x) in ng/mL. The linearity of the relationship between peak area ratio and concentration was demonstrated by the correlation coefficients (R) obtained for the linear regression of WT-161.

The intra-assay accuracy result (ranged from 99.86% to 121.96%) showed that the method is reliable (Tables 1-2 below).

TABLE 1

Dose Solution Analysis Result by HPLC

| Dose level | Nominal Conc. (mg/mL) | Cacul. Conc. (mg/mL) | Accuracy % |
|---|---|---|---|
| IV-2 mg/mL | 2 | 2.34 | 116.92 |

TABLE 2

Intra-assay Precision and Accuracy

| Replicates | Conc. (ng/mL) & Accuracy (%) 8 | 200 | 800 |
|---|---|---|---|
| 1 | 9.76 (121.96) | 199.73 (99.86) | 888.73 (111.09) |
| 2 | 8.97 (112.13) | 231.80 (115.90) | 928.21 (116.03) |
| Mean | 9.36 (117.04) | 215.76 (107.88) | 908.47 (113.56) |

Pharmacokinetic Data Analysis. The concentration in plasma below the limit of quantitation (LOQ=5 ng/mL) were designated as zero. The pharmacokinetic data analysis was performed using noncompartmental analysis modules in DAS 2.0.

Results and Discussion.

Pharmacokinetic after Intravenous Injection. The individual and average concentration-time data for intravenously dosed group are listed in Table 3 and graphically represented in FIG. 8. Selected noncompartmental pharmacokinetic parameters following an IV dose are listed in Table 4.

Following an IV bolus injection of WT-161 at 5 mg/kg, the value of systemic clearance was 1.64 L/hr/kg, which corresponded to 30.37% of mouse hepatic blood flow (5.40 L/hr/kg). The value of half-life ($T_{1/2}$) for WT-161 was 1.41 hr.

The value of $C_{max}$ (at 2 minutes after dosing) following IV administration at a nominal dose of 5 mg/kg was 1866.3 μg/mL. The value of AUC ($_{0-\infty}$) for WT-161 was 3049.28 hr*ug/L.

WT-161 distributes well in tissues. The volume of distribution at terminal phase was 3.33 L/kg, which corresponded to 4.56 fold of the total body water (0.73 L/kg) in the mice.

TABLE 3

Plasma Concentration of WT-161 in CD-1 Mice Following Intravenous Administration at 5 mg/kg

| Time (hr) | Concentration in plasma (ng/mL) | | | | |
|---|---|---|---|---|---|
| | 1 | 2 | 3 | Mean | S.D |
| 0 | BLQ | BLQ | BLQ | NA | NA |
| 0.033 | 13606.91 | 27492.70 | 14890.74 | 18663.45 | 7673.25 |
| 0.083 | 9326.17 | 6082.36 | 8591.87 | 8000.13 | 1700.94 |
| 0.25 | 2193.58 | 1762.06 | 1336.63 | 1764.09 | 428.48 |
| 0.5 | 933.82 | 780.44 | 1152.36 | 955.54 | 186.91 |
| 1 | 122.63 | 57.74 | 263.97 | 148.11 | 105.45 |
| 2 | 83.62 | 87.92 | 114.00 | 95.18 | 16.44 |
| 3 | 25.12 | 9.38 | 14.37 | 16.29 | 8.05 |
| 4 | 74.08 | 20.79 | 7.37 | 34.08 | 35.28 |
| 6 | 5.87 | BLQ | 6.57 | 4.15 | 3.61 |
| 8 | BLQ | BLQ | BLQ | NA | NA |
| 24 | BLQ | BLQ | BLQ | NA | NA |

BLQ: Below the limit of quantitation
SD: Standard deviation
NA: Not applicable, or fail to collect samples

TABLE 4

Selected Pharmacokinetics Parameters of WT-III-161 in CD-1 Mice Following Intravenous Administration at 5 mg/kg

| $AUC_{(0-t)}$ μg/L*hr | $AUC_{(0-\infty)}$ μg/L*hr | $MRT_{(0-\infty)}$ hr | $T_{1/2z}$ hr | $T_{max}$ hr | $V_Z$ L/kg | $CL_Z$ L/hr/kg | $C_{max}$ μg/L |
|---|---|---|---|---|---|---|---|
| 3023.25 | 3049.28 | 0.33 | 1.41 | 0.03 | 3.33 | 1.64 | 18663.45 |

NA: Not applicable

Example 3

General Method of Determining of in vivo Activity against Tumors

Although a variety of methods can be utilized, one exemplary method by which the in vivo activity of the inventive compounds is determined is by subcutaneously transplanting a desired tumor mass in mice. Drug treatment is then initiated when tumor mass reaches approximately 100 $mm^3$ after transplantation of the tumor mass. A suitable composition is then administered to the mice, preferably in saline and also preferably administered once a day at doses of 5, 10, and 25 mg/kg, although it will be appreciated that other doses can also be administered. Body weight and tumor size are then measured daily and changes in percent ratio to initial values are plotted. In cases where the transplanted tumor ulcerates, the weight loss exceeds 25-30% of control weight loss, the tumor weight reaches 10% of the body weight of the cancer-bearing mouse, or the cancer-bearing mouse is dying, the animal is sacrificed in accordance with guidelines for animal welfare.

Example 4

General Biological Assay Procedures

Cell culture and Transfections. TAg-Jurkat cells were transfected by electroporation with 5 μg of FLAG-epitope-tagged pBJ5 constructs for expression of recombinant proteins. Cells were harvested 48 h posttransfection.

HDAC assays. [$^3$H]Acetate-incorporated histones were isolated from butyrate-treated HeLa cells by hydroxyapatite chromatography (as described in Tong, et al. *Nature* 1997, 395, 917-921). Immunoprecipitates were incubated with 1.4 μg (10,000 dpm) histones for 3 h at 37° C. HDAC activity was determined by scintillation counting of the ethyl acetate-soluble [$^3$H]-acetic acid (as described in Taunton, et al., *Science* 1996, 272, 408-411). Compounds were added in DMSO such that final assay concentrations were 1% DMSO. $IC_{50}$s were calculated using Prism 3.0 software. Curve fitting was done without constraints using the program's Sigmoidal-Dose Response parameters. All data points were acquired in duplicate and IC50s are calculated from the composite results of at least two separate experiments.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A compound of the formula (I):

(I)

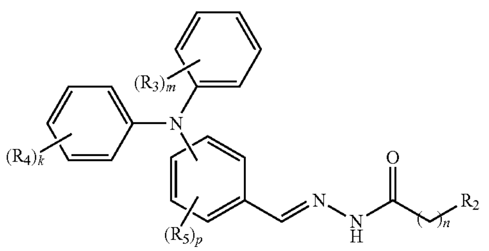

wherein n is an integer between 1 and 10, inclusive;

m is an integer between 0 and 5, inclusive;

k is an integer between 0 and 5, inclusive;

p is an integer between 0 and 5, inclusive;

$R_2$ is an optionally substituted acyl moiety $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR_C$; $-C(=O)R_C$; $-CO_2R_C$; —CN; —SCN;

—$SR_C$; —$SOR_C$; —$SO_2R_C$; —$NO_2$; —$N(R_C)_2$; —$NHC(=O)R_C$; or —$C(R_C)_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; —$C(=O)R_D$; —$CO_2R_D$; —CN; —SCN; —$SR_D$; —$SOR_D$; —$SO_2R_D$; —$NO_2$; —$N(R_D)_2$; —$NHC(=O)R_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_E$; —$C(=O)R_E$; —$CO_2R_E$; —CN; —SCN; —$SR_E$; —$SOR_E$; —$SO_2R_E$; —$NO_2$; —$N(R_E)_2$; —$NHC(=O)R_E$; or —$C(R_E)_3$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and pharmaceutically acceptable forms thereof.

2. The compound according to claim 1, wherein n is 4 to 7, inclusive.

3. The compound according to claim 2, wherein n is 6.

4. The compound according to claim 1, wherein m is 0, 1, or 2.

5. The compound according to claim 1, wherein p is 0, 1, or 2.

6. The compound according to claim 1, wherein k is 0, 1, or 2.

7. The compound of claim 1, wherein the sum of m, p, and k is 0.

8. The compound according to claim 1, wherein $R_2$ is —$C(=O)R_B$, wherein $R_B$ is selected from —OR' or —N(R")$_2$, wherein R' is hydrogen or an optionally substituted alkyl moiety, and wherein R" is hydrogen, —OH, an optionally substituted aryl moiety, or an optionally substituted heteroaryl moiety.

9. The compound of claim 8, wherein $R_2$ is —$CO_2H$.

10. The compound of claim 8, wherein $R_B$ is —OR'; and R' is an optionally substituted alkyl.

11. The compound of claim 10, wherein R' is —$CH_3$, —$CH_2CH_3$, —$CH_2CH_2CH_3$, or —$CH(CH_3)_2$.

12. The compound of claim 8, wherein $R^B$ is selected from —NHR", and wherein R" is selected from —OH, optionally substituted aryl, or optionally substituted heteroaryl.

13. The compound of claim 12, wherein R" is —OH.

14. The compound of claim 12, wherein R" is an optionally substituted aryl moiety.

15. The compound of claim 14, wherein the aryl moiety is of the structure:

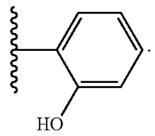 [SMILES: *c1ccccc1O]

16. The compound of claim 1, wherein the compound is selected from the group consisting of:

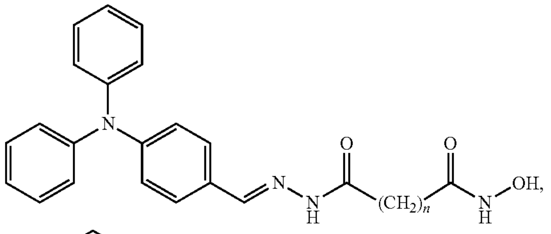

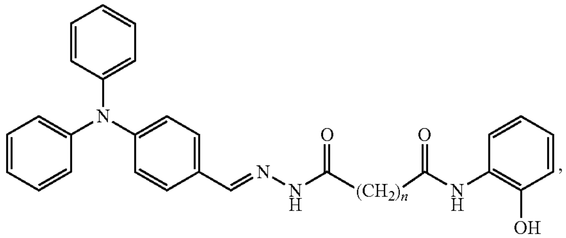

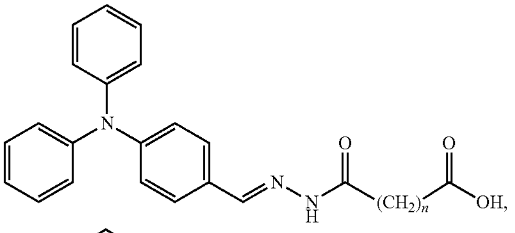

and

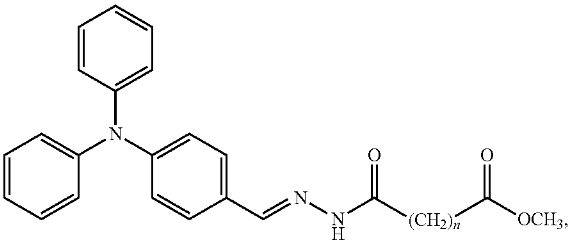

wherein n is 4, 5, 6, or 7; and pharmaceutically acceptable forms thereof.

17. The compound of claim 1, wherein the compound is:

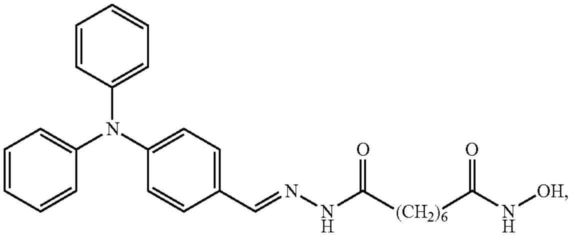

or a pharmaceutically acceptable form thereof.

18. A pharmaceutical composition comprising a therapeutically effective amount of a compound of claim 1, and a pharmaceutically acceptable excipient.

19. A method of inhibiting a deacetylase activity, the method comprising steps of contacting a deacetylase with a compound of claim 1.

* * * * *